(12) United States Patent
Burden et al.

(10) Patent No.: US 9,574,015 B2
(45) Date of Patent: Feb. 21, 2017

(54) METHODS FOR TREATING MUSCLE SPECIFIC RECEPTOR KINASE (MUSK) MYASTHENIA GRAVIS WITH THE IG1 DOMAIN OF MUSK

(71) Applicants: Steven J. Burden, Sharon, CT (US); Wei Zhang, New York, NY (US); Maartje Huijbers, Leiden (NL); Johannes J. Verschuuren, Oegstgeest (NL); Silvère M. van der Maarel, Oegstgeest (NL)

(72) Inventors: Steven J. Burden, Sharon, CT (US); Wei Zhang, New York, NY (US); Maartje Huijbers, Leiden (NL); Johannes J. Verschuuren, Oegstgeest (NL); Silvère M. van der Maarel, Oegstgeest (NL)

(73) Assignees: New York University, New York, NY (US); Leiden University Medical Center, Leiden (NL)

( * ) Notice: Subject to any disclaimer, the term of this patent is extended or adjusted under 35 U.S.C. 154(b) by 0 days.

(21) Appl. No.: 14/486,400

(22) Filed: Sep. 15, 2014

(65) Prior Publication Data
US 2015/0125442 A1 May 7, 2015

Related U.S. Application Data

(60) Provisional application No. 61/877,557, filed on Sep. 13, 2013.

(51) Int. Cl.
*A61K 38/17* (2006.01)
*A61P 21/04* (2006.01)
*C07K 14/705* (2006.01)
*C07K 16/42* (2006.01)
*A61K 35/16* (2015.01)
*C07K 14/47* (2006.01)

(52) U.S. Cl.
CPC .......... *C07K 16/4258* (2013.01); *A61K 35/16* (2013.01); *A61K 38/1774* (2013.01); *C07K 14/4713* (2013.01); *C07K 14/705* (2013.01); *C07K 14/70503* (2013.01)

(58) Field of Classification Search
None
See application file for complete search history.

(56) References Cited

U.S. PATENT DOCUMENTS 6,852,838 B2   2/2005   Valenzuela et al.
2002/0164702 A1  11/2002   Valenzuela et al.

OTHER PUBLICATIONS

Klooster et al, 2012. Brain. 135: 1081-1101.*
Sheng et al, 2010. Exp Neurol. 225(2): 320-327.*
Burden et al., "The role of MuSK in synapse formation and neuromuscular disease", Cold Spring Harb Perspect Biol, 2013, 5:a009167, 1-11.
DeChiara et al., "The receptor tyrosine kinase MuSK is required for neuromuscular junction formation in vivo", Cell, 1996,85:501-512.
Hoch et al., "Auto-antibodies to the receptor tyrosine kinase MuSK in patients with myasthenia gravis without acetylcholine receptor antibodies", Nat Med, 2001, 7:365-368.
Klooster et al., "Muscle-specific kinase myasthenia gravis IgG4 autoantibodies cause severe neuromuscular junction dysfunction in mice", Brain, 2012,135:1081-1101.
McConville et al., "Detection and characterization of MuSK antibodies in seronegative myasthenia gravis", Ann Neurol, 2004,55:580-584.
Niks et al., "Clinical fluctuations in MuSK myasthenia gravis are related to antigen-specific IgG4 instead of IgG1", J Neuroimmunol, 2008,195:151-156.
van der Neut Kolfschoten et al., "Anti-inflammatory activity of human IgG4 antibodies by dynamic Fab arm exchange", Science, 2007, 317:1554-1557.
Mori et al., "Antibodies against muscle-specific kinase impair both presynaptic and postsynaptic functions in a murine model of myasthenia gravis", Am J Pathol, 2012, 180:798-810.
Zhang et al., "Agrin binds to the N-terminal region of Lrp4 protein and stimulates association between Lrp4 and the first immunoglobulin-like domain in muscle-specific kinase (MuSK)", J Biol Chem, 2011, 286:40624-40630.
Stiegler et al., "Crystal structure of the agrin-responsive immunoglobulin-like domains 1 and 2 of the receptor tyrosine kinase MuSK", J Mol Biol, 2006, 364:424-433.
Huijbers et al., "MuSK IgG4 autoantibodies cause myasthenia gravis by inhibiting binding between MuSK and Lrp4", Proc Natl Acad Sci, 2013, 110:20783-20788.
Yumoto et al., "Lrp4 is a retrograde signal for presynaptic differentiation at neuromuscular synapses", Nature, 2012, 489:438-442.
Hesser et al., "Synapse disassembly and formation of new synapses in postnatal muscle upon conditional inactivation of MuSK", Mol Cell Neurosci, 2006, 31:470-480.
Kong et al., "Inhibition of synapse assembly in mammalian muscle in vivo by RNA interference", EMBO Reports, 2004, 5:183-188.
Till et al. "Crystal structure of the MuSK tyrosine kinase: insights into receptor autoregulation", Structure, 2002, 10:1187-1196.
Kawakami et al., "Anti-MuSK autoantibodies block binding of collagen Q to MuSK", Neurology, 2011, 77:1819-1826.

(Continued)

*Primary Examiner* — Zachary Howard
(74) *Attorney, Agent, or Firm* — Klauber & Jackson LLC

(57) ABSTRACT

Agents, compositions, and medicaments that reduce interactions between muscle specific kinase receptor (MuSK) and pathogenic immunoglobulin G4 (IgG4) antibodies specific for the first Ig-like domain of MuSK and methods and uses thereof to reduce such interactions are encompassed herein. Also encompassed are screening assays to identify inhibitors of these pathogenic antibodies, particularly those that reduce binding to MuSK. Agents identified using the screening assays described herein are envisioned for use as therapeutics, alone or in compositions or in medicaments, to improve motor function in subjects afflicted MuSK-MG.

11 Claims, 22 Drawing Sheets

(56) References Cited

OTHER PUBLICATIONS

Takamori et al,. Antibodies against Wnt receptor of muscle-specific tyrosine kinase in myasthenia gravis, J Neuroimmunol, 2013, 254:183-186.
Cole et al., "Patient autoantibodies deplete postsynaptic muscle-specific kinase leading to disassembly of the ACh receptor scaffold and myasthenia gravis in mice", J Physiol, 2010, 588:3217-3229.
Viegas et al., Passive and active immunization models of MuSK-Ab positive myasthenia: electrophysiological evidence for pre and postsynaptic defects, Exp Neurol, 2012, 234:506-512.
Herbst et al., "The juxtamembrane region of MuSK has a critical role in agrin-mediated signaling", The EMBO Journal, 2000, 19:67-77.
Hubbard et al., "Structure and activation of MuSK, a receptor tyrosine kinase central to neuromuscular junction formation", Biochimica et Biophysica Acta, 2013, 1834:2166-2169.
Sallenmuller et al., "Salbutamol-responsive limb-girdle congenital myasthenic syndrome due to a novel missense mutation and heteroallelic deletion in MuSK", Neuromuscular Disorders, 2014, 24:31-35.

\* cited by examiner

Figure 1 (cont)
b
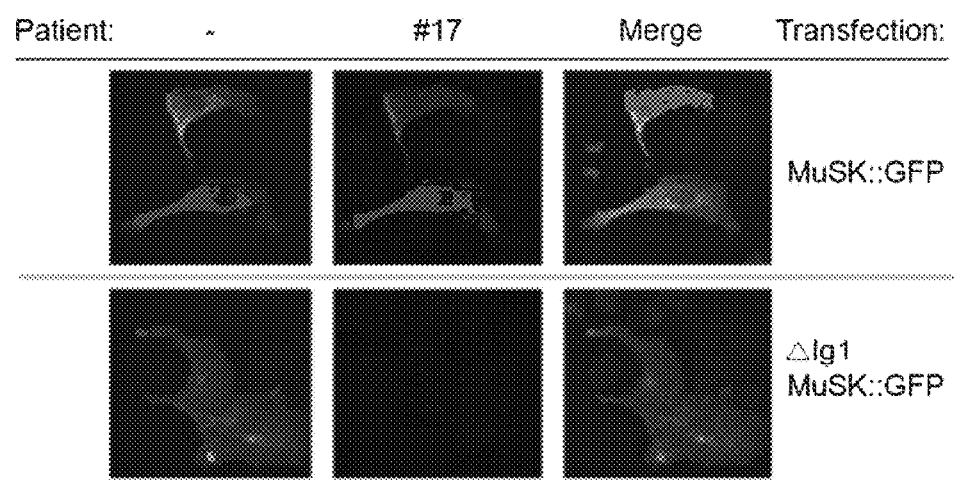
c
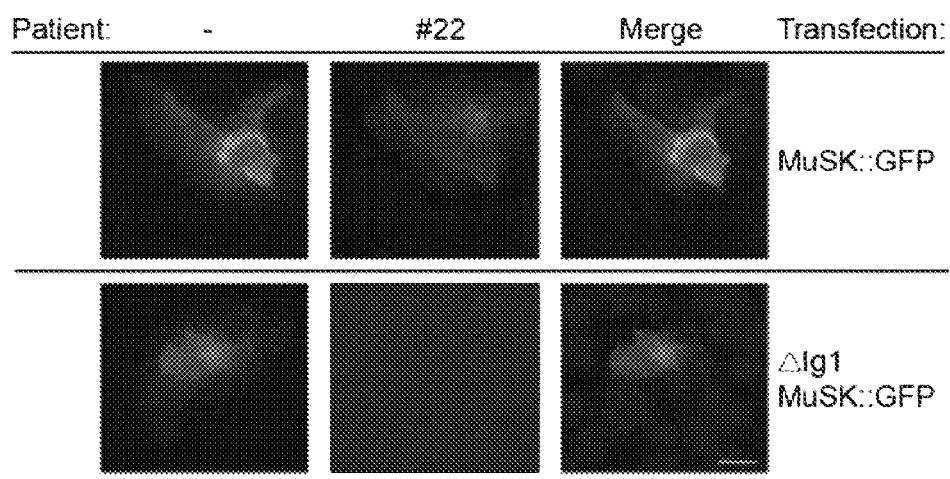

Figure 2
a
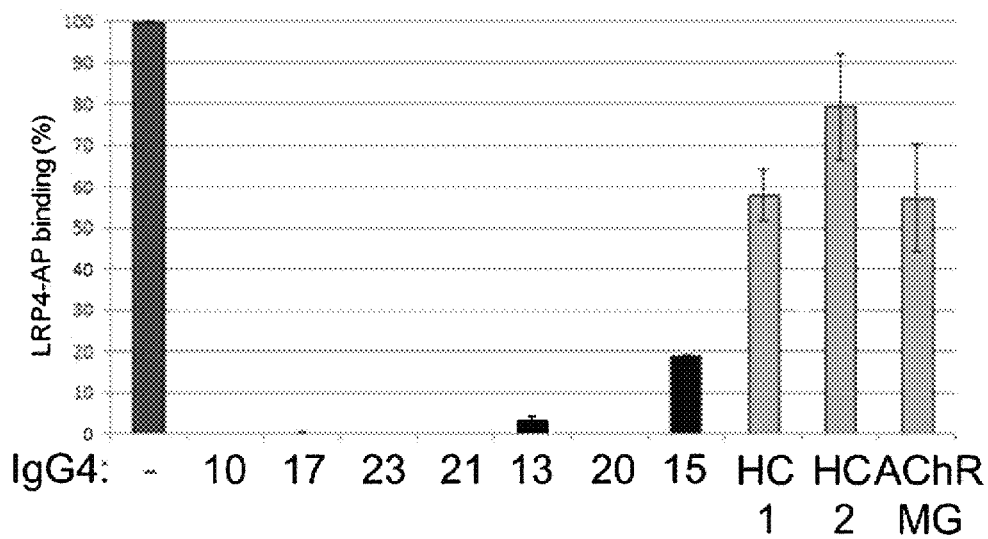
b
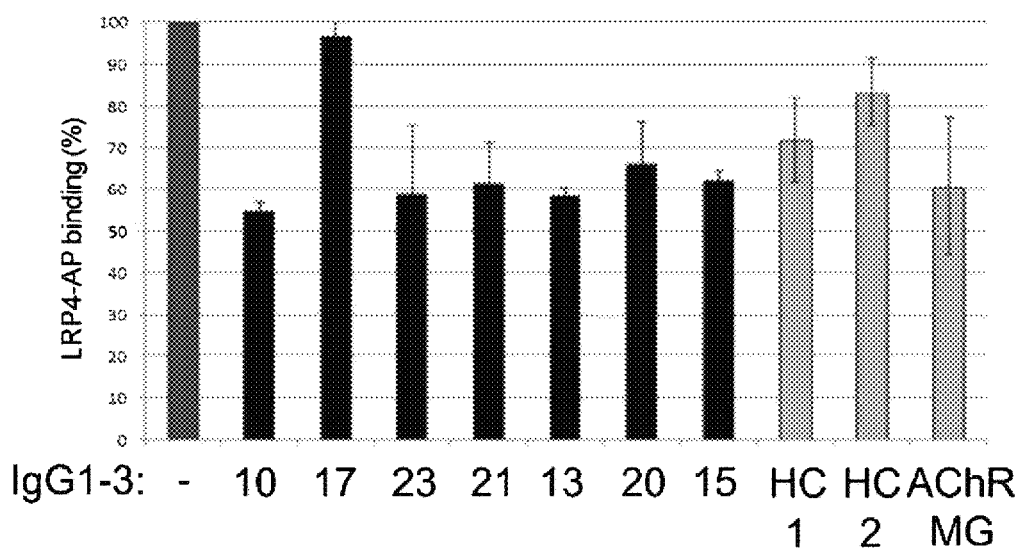

Figure 2 (cont)
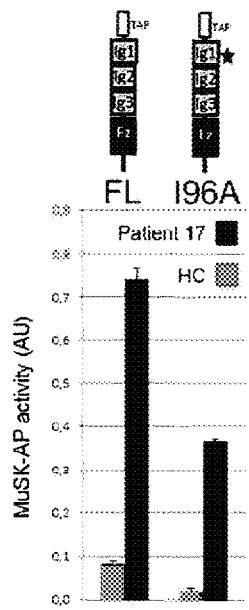
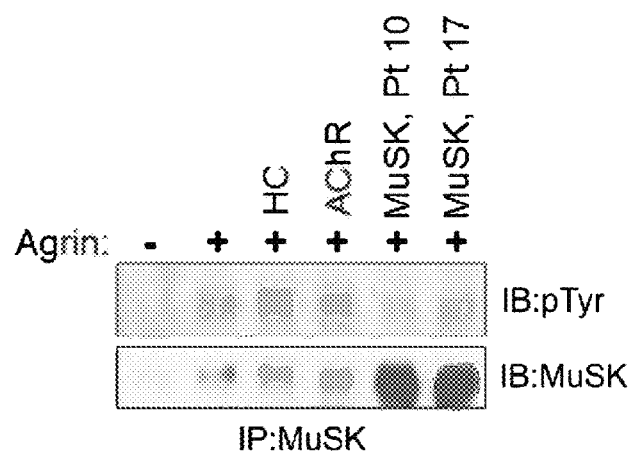
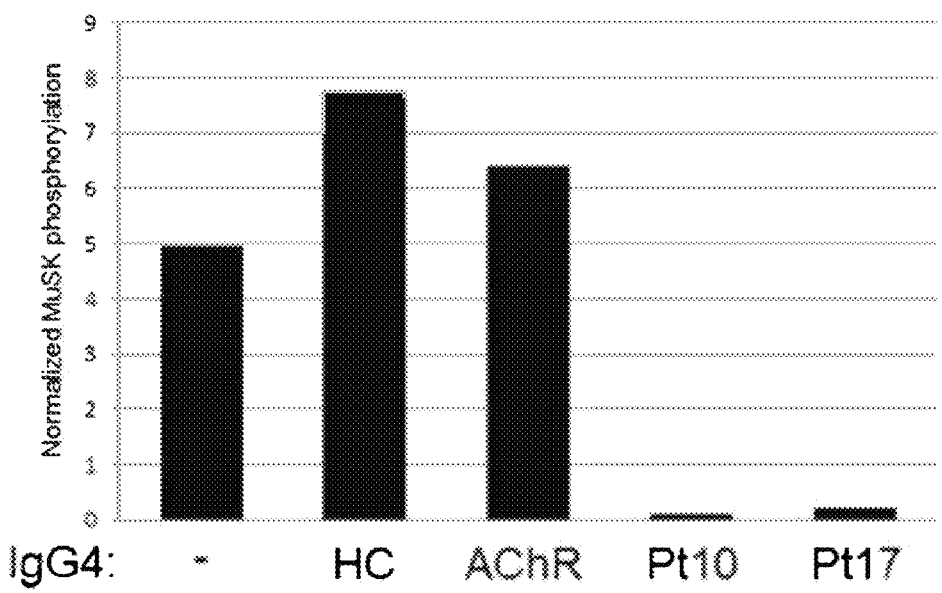

Figure 3 (cont)
e
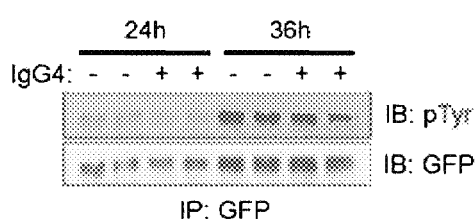
f
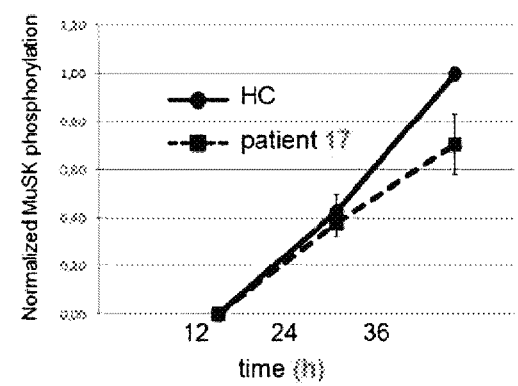
g
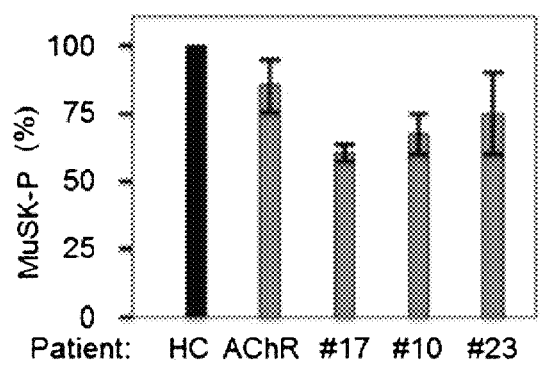

Figure 5A

Homo sapiens muscle specific tyrosine kinase receptor (MUSK) mRNA, complete cds

GenBank: AF006464.1

FASTA Graphics

---

Go to:

```
LOCUS       AF006464                2666 bp    mRNA    linear   PRI 15-JUL-1997
DEFINITION  Homo sapiens muscle specific tyrosine kinase receptor (MUSK) mRNA,
            complete cds.
ACCESSION   AF006464
VERSION     AF006464.1  GI:2253311
KEYWORDS    .
SOURCE      Homo sapiens (human)
  ORGANISM  Homo sapiens
            Eukaryota; Metazoa; Chordata; Craniata; Vertebrata; Euteleostomi;
            Mammalia; Eutheria; Euarchontoglires; Primates; Haplorrhini;
            Catarrhini; Hominidae; Homo.
REFERENCE   1  (bases 1 to 2666)
  AUTHORS   Valenzuela,D.M., Stitt,T.N., DiStefano,P.S., Rojas,E., Mattsson,K.,
            Compton,D.L., Nunez,L., Park,J.S., Stark,J.L., Gies,D.R.,
            Thomas,S., LeBeau,M.M., Fernald,A.A., Copeland,N.G., Jenkins,N.A.,
            Burden,S.J., Glass,D.J. and Yancopoulos,G.D.
  TITLE     Receptor tyrosine kinase specific for the skeletal muscle lineage:
            expression in embryonic muscle, at the neuromuscular junction, and
            after injury
  JOURNAL   Neuron 15 (3), 573-584 (1995)
  PUBMED    7546737
REFERENCE   2  (bases 1 to 2666)
  AUTHORS   Valenzuela,D.M., Rojas,E. and Yancopoulos,G.D.
  TITLE     Direct Submission
  JOURNAL   Submitted (30-MAY-1997) Discovery Group, Regeneron Pharmaceuticals,
            Inc., 777 Old Saw Mill River Rd., Tarrytown, NY 10591, USA
FEATURES             Location/Qualifiers
     source          1..2666
                     /organism="Homo sapiens"
                     /mol_type="mRNA"
                     /db_xref="taxon:9606"
                     /chromosome="9"
                     /map="9q31.3-32"
     gene            1..2666
                     /gene="MUSK"
     CDS             47..2656
                     /gene="MUSK"
                     /codon_start=1
                     /product="muscle specific tyrosine kinase receptor"
                     /protein_id="AAB63044.1"
                     /db_xref="GI:2253312"
                     /translation="MRELVNIPLVHILTLVAFSGTEKLPKAPVTITIPLETVDALVEEV
                     ATFMCAVESYPQPEISWTRNKILIKLFDTRYSIRENGQLLTILSVEDSDDGIYCCTAN
                     NGVGGAVESCGALQVEMKPKITRPPINVKIIEGLKAVLPCTTMGNPKPSVSWIKGDSP
                     LRENSRIAVLESGSLRIHNVQKEDAGQYRCVAKNSLGTAYSKVVKLEVEVFARJLRAP
                     ESHHVTPGSFVTLHCTATGIPVPTITWIENGNAVSSGSIQSSVKDRVIDSRLQLFITK
                     PGLYTCIATEKHGEKFSTAKAAATISIAERSKFQKDKNKGYCAQYRGEVCNAVLAKDAL
                     VFLNTSYADPEEAQELLVHTAWRELKVVSFVCRPAAEALLCNHIFQECSPGVVPTFIP
                     ICREYCIAVKELFCAKEWLVMEEKTHSGLYRSEMHLLSVPECSKLPSMHWDPTACARL
                     PHLDYNKENLKCFPPMTSSKFSVDYPHLPSSESSSFSVSPTYSMTVIISIMSSFAIEV
                     LLTITTLYCCRRRKQWKDKKREGAAVTLTTLPSELLLDRLRPNPMYQRMPLLLNPKLL
                     SLEYPRNNIEYVRDIGEGAFGRVFQARAPGLLPYEPFTMVAVKMLKEEASADMQADFQ
                     REAALMAEFDNPNIVKLLGVCAVGKPMCLLFEYMAYGDLNSFLRSMSPHTVCSLSHSD
                     LSMRAQVSSPGFPPLSCAEQLCTARQVAAGMAYLSERKFVHRDLATRNCLVGENMVVK
                     IADPGLSRNYYSADYYKANEMDAIPIRWMPPESIFYNRYTTESPVWAYGVVLWEIFSY
                     GLQPYYGMAMEEVIYYVRDGNILSCPENCPVELYNLMRLCWSKLPADRPSFTSIHRIL
                     ERMCERAESGTVSV"
ORIGIN      
        1 tgcgttgtcc agaaggaact tcgtcctgcg tgagcctgga ttaatcatga gagagctcgt
       61 caacatccca ctggtacata ttcttactct ggttgccttc agcggaactg agaaacttcc
      121 aaaagctcct gtcatcacca ctcctcttga aacagtggat gcccttgttg aagaagtggc
      181 tacttttatg tgtgcagtgg aatcctaccc ccagcctgag atttcctgga ctagaaataa
      241 aatcctcatt aaactctttg acaccaggta cagcatccgg gagaatggcc agctcctcac
      301 catcctgagt gtggaagaca gtgatgatgg catttactgc tgcacggcca acaatggtgt
      361 gggaggagct gtggagagtt gtggagccct gcaagtgaag atgaaaccta aaataactcg
      421 ccctcccata aatgtgaaaa taatagaggg attaaaagca gtcctaccat gtactacaat
```

Figure 5B

```
 481 gggtaatccc aaaccatcag tgtcttggat aaagggagac agccctctca gggaaaattc
 541 ccgaattgca gttcttgaat ctgggagctt gaggattcat aacgtacaaa aggaagatgc
 601 aggacagtat cgatgtgtgg caaaaacag cctcgggaca gcatattcca aagtggtgaa
 661 gctggaagtt gaggtttttg ccaggatcct gcgggctcct gaatcccaca atgtcacctt
 721 tggctccttt gtgaccctgc actgtacagc aacaggcatt cctgtcccca ccatcacctg
 781 gattgaaaac ggaaatgctg tttcttctgg gtccattcaa gagagtgtga aagaccgagt
 841 gattgactca agactgcagc tgtttatcac caagccagga ctctacacat gcatagctac
 901 caataagcat ggggagaagt tcagtactgc caaggctgca gccaccatca gcatagcaga
 961 atggagtaaa ccacagaaag ataacaaagg ctactgcgcc cagtacagag gggaggtgtg
1021 taatgcagtc ctggcaaaag atgctcttgt tttctcaac acctcctatg cggaccctga
1081 gcaggcccaa gagctactgg tccacacggc ctggaatgaa ctgaaagtag tgagtccagt
1141 ctgccggcca gctgctgagg cttcgttgtg taaccacatc ttccaggagt gcagtcctgg
1201 agtagtgcct actcctattc ccatttgcag agagtactgc ttggcagtaa aggagctctt
1261 ctgcgcaaaa gaatggctgg taatggaaca gaagacccac agaggactct acagatccga
1321 gatgcatttg ctgtccgtgc cagaatgcag caagcttccc agcatgcatt gggacccgac
1381 ggcctgtgcc agactgccac atctagatta taacaaagaa aacctaaaaa cattcccacc
1441 aatgacgtcc tcaagccaa gtgtggacat tccaaatctg ccttcctcct cctcttcttc
1501 cttctctgtc tcacctacat actccatgac tgtaataatc tccatcatgt ccagctttgc
1561 aacatttgtg cttcttacca taactactct ctattgctgc cgaagaagaa aacaatggaa
1621 aaataagaaa agagaatcag cagcagtaac cctcaccaca ctgcctctg agctcttact
1681 agatagactt catcccaacc ccatgtacca gaggatgccg ctccttctga acccccaaatt
1741 gctcagcctg gagtatccaa ggaataacat tgaatatgtg agagacatcg gagagggagc
1801 gtttggaagg gcgttcaag caaggcacc aggcttactt cccatgaac cttcactat
1861 ggtggcagta aagatgctca aagaagaagc ctcggcagat atgcaagcgg actttcagag
1921 ggaggcagcc ctcatggcag aatttgacaa cctaacatt gtgaagctat taggagtgtg
1981 tgtcgtcggg aagccaatgt gcctgctctt tgaatacatg gcctatggtg acctcaatga
2041 gttcctccgc agcatgtccc ctcaccgt gtgcagcctc agtcacagtg acttgtctat
2101 gagggtcag gtctccagcc ctgggcccc aacccctctcc tgtgctgagc agctttgcat
2161 tgccaggcag gtggcagctg gcatggctta cctctcagaa cgtaagtttg ttcaccgaga
2221 tttagccacc aggaactgcc tggtgggcga gaacatggtg gtgaaaattg ccgactttgg
2281 cctctccagg aacatctact cagcagacta ctacaaagct aatgaaaacg acgctatccc
2341 tatccgttgg atgccaccag agtccatttt ttataaccgc tacactacag agtctgatgt
2401 gtgggcctat ggcgtggtcc tctgggagat cttctcctat ggcctgcagc cctactatgg
2461 gatggcccat gaggaggtca tttactacgt gcgagatggc aacatcctct cctgccctga
2521 gaactgcccc gtggagctgt acaatctcat gcgtctatgt tggagcaagc tgcctgcaga
2581 cagacccagt ttcaccagta ttcaccgaat tctggaacgc atgtgtgaga gggcagagcg
2641 aactgtgagt gtctaaggtt gaagac
```

Figure 6A

Eukaryotic mutant MuSK expression vectors

Based on human MuSK

1. Ig-1 deleted        P28-V117 (exclude)
2. Ig-1 and Ig-2 deleted   P28-V208 (exclude)
3. Ig-1 only           P25-K122 (include)
4. Fz-only             Q310-M466 (include)

Full length MuSK, size 869 aa

MRELVNIPLVHILTLVAFSGTEKLPKA...KMK......EVF...QKDNKGYCAQYRGEVCNAVLAKDALVFLNTSYADPEEAQELVSHTAWNELKVVSPVCRPAAEALLCN
HIFQKCSPGVVPTEIPICREYCLAVKELFCAKEWLVMEEKTHRGLYRSEMHLLSVPECSKLPSMHWDETACARLPHLDYNKENLKTFPPMTSSK
PSVDIPNLFSSSSSSFSVSPTYSMTVIISIMSSFAIFVLLTITTLYCCRRRKQWKNKKRESAAVTLTTLPSELLLDRLHPNPMYQRMPLLLNPK
LLSLEYPRKNIEYVRDIGEGAFGRVFQARAPGLLPYEPFTMVAVKMLKEEASADMQADFQREAALMAEFDNPNIVKLLGVCAVGKPMCLLFEYM
AYGDLNEFLRSMSPHTVCSLSHSDLSMRAQVSSPGPPPLSCAEQLCIARQVAAGMAYLSERKFVHRDLATRNCLVGENMVVKIADFGLSRNIYS
ADYYKANENDAIPIRWMPPESIFYNRYTTESDVWAYGVVLWEIFSYGLQPYYGMAHEEVIYYVRDGNILSCPENCPVELYNLMRLCWSKLPADR
PSFTSIHRILERMCERAEGTV3V (SEQ ID NO: 2)

```
gtggagctgctgacacaaacagtcattagcagacaaccttttgcaacaaagtatgctttaa
 G  A  D  T  N  S  H  -  Q  T  T  L  Q  Q  S  M  L  -
aatgtaaactgtggagccatttttccttgcgttgtccagaaggaacttcgtcctgctgag
 N  V  N  C  G  A  I  F  L  A  L  S  R  R  N  F  V  L  R  E
cctggattaatc...
 P  G  L  I  ...
...
 A  ... L  P  K  A ...
...
 aagatgaaa...
 K  M  K  ...
...
 ...gaggtttt...
         E  V  F
...
                                                         cag
                                                          Q
aaagatgacaaaggctactgc...ccagtacaagggg...
 K  D  N  K  G  Y  C  A  Q  Y  P  G  E  V  C  N  A  V  L  A
aaagatgccttgtttttctcaacacctctatgcagac...
 K  D  A  L  V  F  L  K  T  S  Y  A  D  P  E  E  A  Q  E
ctgtccacacggctggaatgaactgaaagtagtgagccagtctgcggccagctgt
 L  V  H  T  A  W  N  E  L  K  V  V  S  P  V  C  R  P  A  A
aagcttgttgttgtaaccaaatcttccaggcatgcagtcctgaagtagtgcctactgt
 E  A  L  L  C  N  H  I  F  Q  K  C  S  P  V  V  P  T
attccaatttgcagagagtactgctgcagtaaagagctttctgcgcaaaagaatgg
 I  P  I  C  R  E  Y  C  L  A  V  K  E  L  F  C  A  K  E  W
ctgtaatgaagaaaaccgacagg...
 L  V  M  E  E  K  T  R  R  ... L  Y  R  S  E  M  H  L  L  S
gtcccagaatgcagcaagcttccagcatgcattggaccacaggctgtgccagactg
 V  P  E  C  S  K  L  P  S  M  H  W  D  E  T  A  C  A  R  L
ccaatctagattataaacaaagaaacctaaaaacattccaccaatgacgtcctcaaag
 P  H  L  D  Y  N  K  E  N  L  K  T  F  P  P  M  T  S  S  K
```

Figure 6B

```
ccaagtgtggacattccaaatctgcttcctcctcctcttcttccttctctgtctcacct
 P  S  V  D  I  P  N  L  P  S  S  S  S  S  F  S  V  S  P
acatactccatgactgtaataatctccatcatgtccagctttgcaatatttgtgcttctt
 T  Y  S  M  T  V  I  I  S  I  M  S  S  F  A  I  F  V  L  L
accataactactctctattgctgccgaagaagaaaacaatggaaaaataagaaaagagaa
 T  I  T  T  L  Y  C  C  R  R  R  K  Q  W  K  N  K  K  R  E
tcagcagcagtaaccctcaccacactgcttctgagctcttactagatagacttcatccc
 S  A  A  V  T  L  T  T  L  P  S  E  L  L  L  D  R  L  H  P
aaccccatgtaccagaggatgcctcctcctgaacccaaattgctcagcctggagtat
 N  P  M  Y  Q  R  M  P  L  L  L  N  P  K  L  L  S  L  E  Y
ccaaggaataacattgaatatgtgagagacatcggagagggagcgtttggaagggtgttt
 P  R  N  N  I  E  Y  V  R  D  I  G  E  G  A  F  G  R  V  F
caagcaagggcaccaggcttacttccctatgaacctttcactatggtggcagtaaagatg
 Q  A  R  A  P  G  L  L  P  Y  E  P  F  T  M  V  A  V  K  M
ctcaaagaagaagcctcggcagatatgcaagcggactttcagaggggaggcagccctcatg
 L  K  E  E  A  S  A  D  M  Q  A  D  F  Q  R  E  A  A  L  M
gcagaatttgacaaccctaacattgtgaagctattaggagtgtgtgctgtcgggaagcca
 A  E  F  D  N  P  N  I  V  K  L  L  G  V  C  A  V  G  K  P
atgtgcctgctctttgaatacatggcctatggtgacctcaatgagttcctccgcagcatg
 M  C  L  L  F  E  Y  M  A  Y  G  D  L  N  E  F  L  R  S  M
tcccctcacaccgtgtgcagcctcagtcacagtgacttgtctatgagggctcaggtctcc
 S  P  H  T  V  C  S  L  S  H  S  D  L  S  M  R  Q  V  S
agcctgggccccaccctctcctgtgctgagcagctttgcattgccaggcaggtggca
 S  P  G  P  P  P  L  S  C  A  E  Q  L  C  I  A  R  Q  V  A
gctggcatggcttacctctcagaacgtaagtttgttcaccgagatttagccaccaggaac
 A  S  M  A  Y  L  S  E  R  K  F  V  H  R  D  L  A  T  R  N
tgcctggtgggcgagaacatggtggtgaaaattgccgacttttggcctctccaggaacatc
 C  L  V  G  E  N  M  V  V  K  I  A  D  F  G  L  S  R  N  I
tactcagcagactactacaaagctaatgaaaacgacgctatccctatccgttggatgcca
 Y  S  A  D  Y  Y  K  A  N  E  N  D  A  I  P  I  R  W  M  P
ccagagtccatttttataacgctacactacagagtctgatgtgtgggcctatggcgtg
 P  E  S  I  F  Y  N  R  Y  T  T  E  S  D  V  W  A  Y  G  V
gtcctctgggagatctctcctatggcctgcagccctactatgggatggcccatgaggag
 V  L  W  E  I  P  S  Y  G  L  Q  P  Y  Y  G  M  A  H  E  E
gtcatttactacgtgcgagatggcaacatcctcctgccctgagaactgcccgtggag
 V  I  Y  Y  V  R  D  G  N  I  L  S  C  P  E  N  C  P  V  E
ctgtacaatctcatgcgtctatgttggagcaagctgcctgcagacagacccagtttcacc
 L  Y  N  L  M  R  L  C  W  S  K  L  P  A  D  R  P  S  F  T
agtattcaccgaattctggaacgcatgtgtgagagggcagagggaactgtgagtgtctaa
 S  I  H  R  I  L  E  R  M  C  E  R  A  E  G  T  V  S  V  -
ggttgaagac (SEQ ID NO: 3)
 G  -  R  (SEQ ID NO: 4)
```

Figure 7

| Construct | Vector | Insert | Insert sequence (aa) |
|---|---|---|---|
| pET28-hMuSK FL | pET28b | hMuSK extracellular domain (aa 21-493) | TEKLPKAPVITTPLETVDALVEEVATFMCAVESYPQPEISWTRNKILIKLFDTRYSIRENGQLLTILSVEDSDDGIYCCT ANNGVGGAVESCGALQVKMKPKITRPPINVKIIEGLKAVLPCTTMGNPKPSVSWIKGDSPLRENSRIAVLESGSLRIHNV QKEDAGQYRCVAKNSLGTAYSKVVKLEVEVFARILRAPESHNVTFGSFVTLHCTATGIPVPTITWIENGNAVSSGSIQES VKDRVIDSRLQLFITKPGLYTCIATNKHGEKFSTAKAAATISIAEWSKPQKDNKGYCAQYRGEVCNAVLAKDALVFLNTS YADPEEAQELLVHTAWNELKVVSPVCRPAAEALLCNHIFQECSPGVVPTPIPICREYCLAVKELFCAKEWLVMEEKTHRG LYRSEMHLLSVPECSKLPSMHWDPTACARLPHLDYNKENLKTFPMTSSKPSVDIPNLPSSSSSFSVSPTYS (SEQ ID NO: 5) |
| pET28-hMuSK Δ1-50 | pET28a | hMuSK extracellular domain (aa 74-493) | RYSIRENGQLLTILSVEDSDDGIYCCTANNGVGGAVESCGALQVKMKPKITRPPINVKIIEGLKAVLPCTTMGNPKPSVS WIKGDSPLRENSRIAVLESGSLRIHNVQKEDAGQYRCVAKNSLGTAYSKVVKLEVEVFARILRAPESHNVTFGSFVTLHC TATGIPVPTITWIENGNAVSSGSIQESVKDRVIDSRLQLFITKPGLYTCIATNKHGEKFSTAKAAATISIAEWSKPQKDN KGYCAQYRGEVCNAVLAKDALVFLNTSYADPEEAQELLVHTAWNELKVVSPVCRPAAEALLCNHIFQECSPGVVPTPIPI CREYCLAVKELFCAKEWLVMEEKTHRGLYRSEMHLLSVPECSKLPSMHWDPTACARLPHLDYNKENLKTFPMTSSKPSV DIPNLPSSSSSFSVSPTYS (SEQ ID NO: 6) |
| pET28-hMuSK Δ1-200 | pET28b | hMuSK extracellular domain (aa 213-493) | RILRAPESHNVTFGSFVTLHCTATGIPVPTITWIENGNAVSSGSIQESVKDRVIDSRLQLFITKPGLYTCIATNKHGEKF STAKAAATISIAEWSKPQKDNKGYCAQYRGEVCNAVLAKDALVFLNTSYADPEEAQELLVHTAWNELKVVSPVCRPAAEA LLCNHIFQECSPGVVPTPIPICREYCLAVKELFCAKEWLVMEEKTHRGLYRSEMHLLSVPECSKLPSMHWDPTACARLPH LDYNKENLKTFPMTSSKPSVDIPNLPSSSSSFSVSPTYS (SEQ ID NO: 7) |
| pET28-hMuSK FZ | pET28a | hMuSK FZ domain (313-450) | NKGYCAQYRGEVCNAVLAKDALVFLNTSYADPEEAQELLVHTAWNELKVVSPVCRPAAEALLCNHIFQECSPGVVPTPIP ICREYCLAVKELFCAKEWLVMEEKTHRGLYRSEMHLLSVPECSKLPSMHWDPTACARL (SEQ ID NO: 8) |
| pET28-hMuSK part A | pET28a | hMuSK extracellular domain (aa 21-125) | TEKLPKAPVITTPLETVDALVEEVATFMCAVESYPQPEISWTRNKILIKLFDTRYSIRENGQLLTILSVEDSDDGIYCCT ANNGVGGAVESCGALQVKMKPKITR (SEQ ID NO: 9) |

Figure 8 (cont)
In vivo tests:
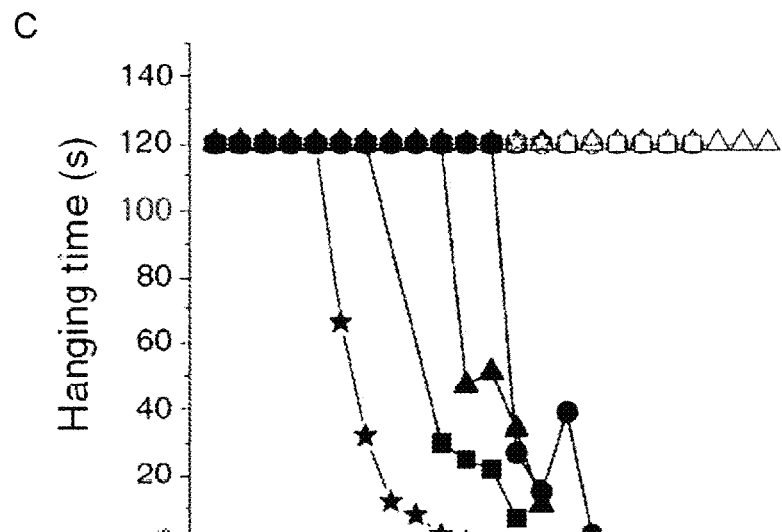
Inverted mesh hang test
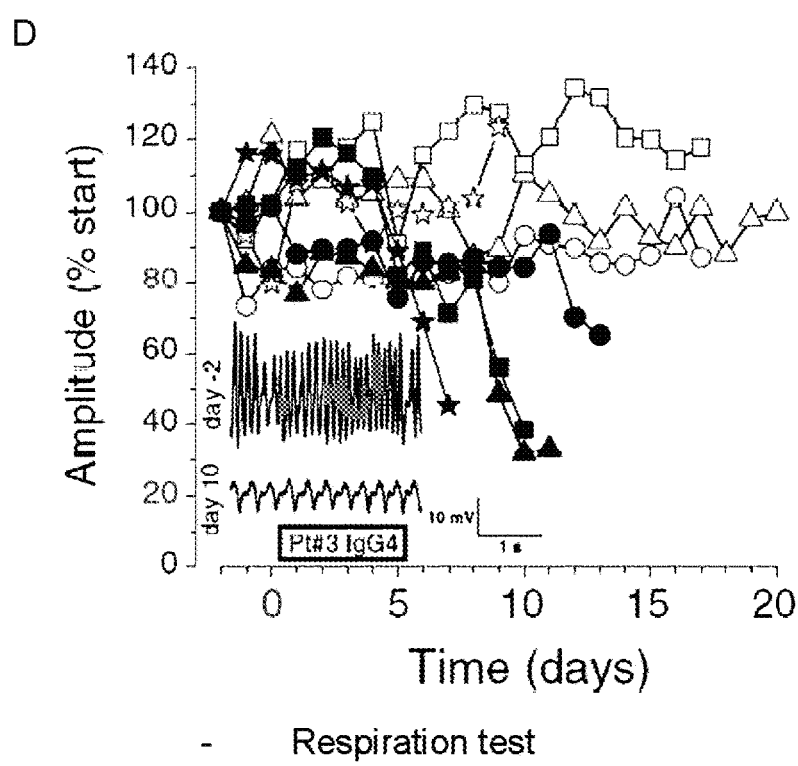
Respiration test

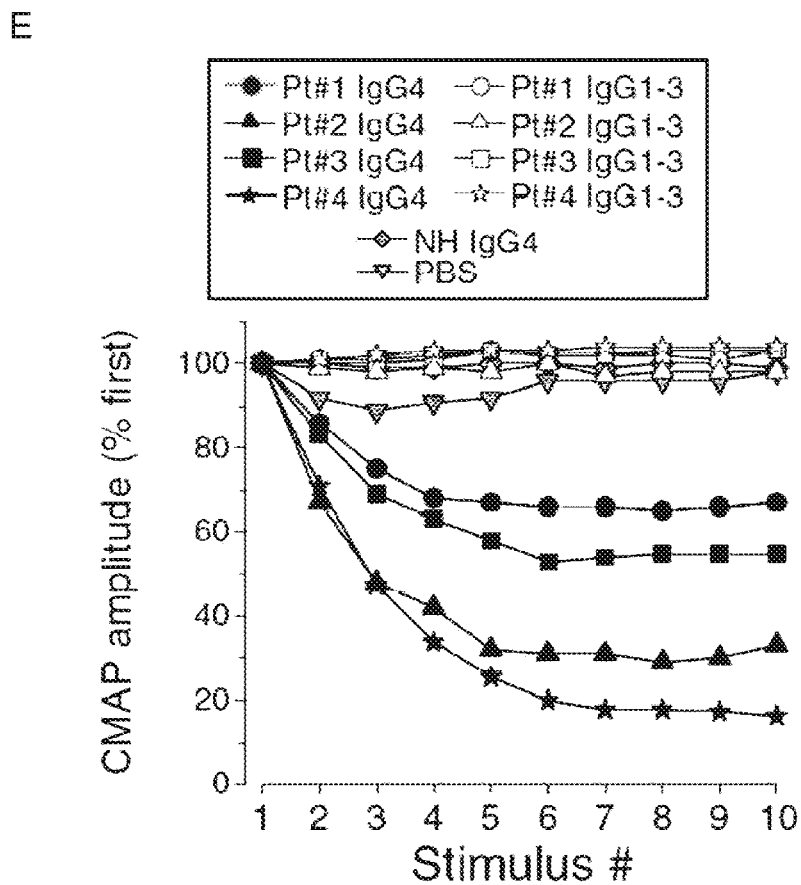

Figure 8 (cont)
End-of-experiment test:
G
Pt#1 IgG4
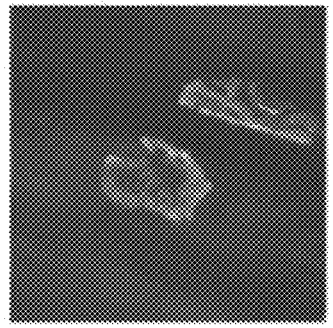
Pt#1 IgG1-3
Dissected muscle:
- Neuromuscular junction morphology

Figure 10A

```
MuSK001    MRELVNIPLVHILTLVAFSGTEKLPKAPVITTPLETVDALVEEVATFMCA
MuSK002    MRELVNIPLVHILTLVAFSGTEKLPKAPVITTPLETVDALVEEVATFMCA
MuSK003    --------------------------------------------------
MuSK004    M--------------AGNGRED----------------------------
MuSK202    MRELVNIPLVHILTLVAFSGTEKLPKAPVITTPLETVDALVEEVATFMCA
musk2.01   MRELVNIPLVHILTLVAFSGTEKLPKAPVITTPLETVDALVEEVATFMCA MuSK001    VESYPQPEISWTRNKILIKLFDTRYSIRENGQLLTILSVEDSDDGIYCCT
MuSK002    VESYPQPEISWTRNKILIKLFDTRYSIRENGQLLTILSVEDSDDGIYCCT
MuSK003    --------------------------------------------------
MuSK004    --------------------------------------------------
MuSK202    VESYPQPEISWTRNKILIKLFDTRYSIRENGQLLTILSVEDSDDGIYCCT
musk2.01   VESYPQPEISWTRNKILIKLFDTRYSIRENGQLLTILSVEDSDDGIYCCT MuSK001    ANNGVGGAVESCGALQVKMKPKITRPPINVKIIEGLKAVLPCTTMGNPKP
MuSK002    ANNGVGGAVESCGALQVKMKPKITRPPINVKIIEGLKAVLPCTTMGNPKP
MuSK003    ---------------------KPKITRPPINVKIIEGLKAVLPCTTMGNPKP
MuSK004    ---------------------PQRT-------------------------
MuSK202    ANNGVGGAVESCGALQVKMKPKITRPPINVKIIEGLKAVLPCTTMGNPKP
musk2.01   ANNGVGGAVESCGALQVKMKPKITRPPINVKIIEGLKAVLPCTTMGNPKP
                                *:  *

MuSK001    SVSWIKGDSPLRENSRIAVLESGSLRIHNVQKEDAGQYRCVAKNSLGTAY
MuSK002    SVSWIKGDSPLRENSRIAVLESGSLRIHNVQKEDAGQYRCVAKNSLGTAY
MuSK003    SVSWIKGDSPLRENSRIAVLESGSLRIHNVQKEDAGQYRCVAKNSLGTAY
MuSK004    ------------------------------LQIRDAF-------------
MuSK202    SVSWIKGDSPLRENSRIAVLESGSLRIHNVQKEDAGQYRCVAKNSLGTAY
musk2.01   SVSWIKGDSPLRENSRIAVLESGSLRIHNVQKEDAGQYRCVAKNSLGTAY
                                         :*  .**

MuSK001    SKVVKLEVE----------VFARILRAPESHNVTFGSFVTLHCTATGIPV
MuSK002    SKVVKLEVE----------VFARILRAPESHNVTFGSFVTLHCTATGIPV
MuSK003    SKVVKLEVE----------GA---------------------KG------
MuSK004    -----------------AVRARMQQASQ---H------------------
MuSK202    SKVVKLEVEEESEPEQDTKVFARILRAPESHNVTFGSFVTLHCTATGIPV
musk2.01   SKVVKLEVEEESEPEQDTKVFARILRAPESHNVTFGSFVTLHCTATGIPV MuSK001    PTITWIENGNAVSSGSIQESVKDRVIDSRLQLFITKPGLYTCIATNKHGE
MuSK002    PTITWIENGNAVSSGSIQESVKDRVIDSRLQLFITKPGLYTCIATNKHGE
MuSK003    --------------------------------------------------
MuSK004    --------------------------------------------------
MuSK202    PTITWIENGNAVSSGSIQESVKDRVIDSRLQLFITKPGLYTCIATNKHGE
musk2.01   PTITWIENGNAVSSGSIQESVKDRVIDSRLQLFITKPGLYTCIATNKHGE MuSK001    KFSTAKAAATISIAEWSKPQKDNKGYCAQYRGEVCNAVLAKDALVFLNTS
MuSK002    KFSTAKAAATISIAEWSKPQKDNKGYCAQYRGEVCNAVLAKDALVFLNTS
MuSK003    --------------------------------------------------
MuSK004    --------------------------------------------------
```

Figure 10B

```
MuSK202     KFSTAKAAATISIADF------------------------------------
musk2.01    KFSTAKAAATISIAEW------------------------------------

MuSK001     YADPEEAQELLVHTAWNELKVVSPVCRPAAEALLCNHIFQECSPGVVPTP
MuSK002     YADPEEAQELLVHTAWNELKVVSPVCRPAAEALLCNHIFQECSPGVVPTP
MuSK003     -------------------------------------------------
MuSK004     -------------------------------------------------
MuSK202     -------------------------------------------------
musk2.01    -------------------------------------------------

MuSK001     IPICREYCLAVKELFCAKEWLVMEEKTHRGLYRSEMHLLSVPECSKLPSM
MuSK002     IPICREYCLAVKELFCAKEWLVMEEKTHRGLYRSEMHLLSVPECSKLPSM
MuSK003     -------------------------------------------------
MuSK004     -------------------------------------------------
MuSK202     ----REYCLAVKELFCAKEWLVMEEKTHRGLYRSEMHLLSVPECSKLPSM
musk2.01    ----REYCLAVKELFCAKEWLVMEEKTHRGLYRSEMHLLSVPECSKLPSM MuSK001     HWDPTACARLPHLDYNKENLKTFPPMTSSKPSVDIPNLPSSSSSSFSVSP
MuSK002     HWDPTACARLPHL--------AFPPMTSSKPSVDIPNLPSSSSSSFSVSP
MuSK003     -------------------------------------------------
MuSK004     -------ALGPHGLC----------------------------------
MuSK202     HWDPTACARLPHL--------AFPPMTSSKPSVDIPNLPSSSSSSFSVSP
musk2.01    HWDPTACARLPHL--------AFPPMTSSKPSVDIPNLPSSSSSSFSVSP MuSK001     TYSMTVIISIMSSFAIFVLLTITTLYCCRRRKQWKNKKRESAAVTLTTLP
MuSK002     TYSMTVIISIMSSFAIFVLLTITTLYCCRRRKQWKNKKRESAAVTLTTLP
MuSK003     -------------------------------------------------
MuSK004     ---------------------------------QTATSRESAAVTLTTLP
MuSK202     TYSMTVIISIMSSFAIFVLLTITTLYCCRRRKQWKNKKRESAAVTLTTLP
musk2.01    TYSMTVIISIMSSFAIFVLLTITTLYCCRRRKQWKNKKRESAAVTLTTLP MuSK001     SELLLDRLHPNPMYQRMPLLLNPKLLSLEYPRNNIEYVRDIGEGAFGRVF
MuSK002     SELLLDRLHPNPMYQRMPLLLNPKLLSLEYPRNNIEYVRDIGEGAFGRVF
MuSK003     -------------------------------------------------
MuSK004     SELLLDRLHPNPMYQRMPLLLNPKLLSLEYPRNNIEYVRDIGEGAFGRVF
MuSK202     SELLLDRLHPNPMYQRMPLLLNPKLLSLEYPRNNIEYVRDIGEGAFGRVF
musk2.01    SELLLDRLHPNPMYQRMPLLLNPKLLSLEYPRNNIEYVRDIGEGAFGRVF MuSK001     QARAPGLLPYEPFTMVAVKMLKEEASADMQADFQREAALMAEFDNPNIVK
MuSK002     QARAPGLLPYEPFTMVAVKMLKEEASADMQADFQREAALMAEFDNPNIVK
MuSK003     ------------------------------IHTQFVASA----------
MuSK004     QARAPGLLPYEPFTMVAVKMLKEEASADMQADFQREAALMAEFDNPNIVK
MuSK202     QARAPGLLPYEPFTMVAVKMLKEEASADMQADFQREAALMAEFDNPNIVK
musk2.01    QARAPGLLPYEPFTMVAVKMLKEEASADMQADFQREAALMAEFDNPNIVK
                                          ::::*  .*

MuSK001     LLGVCAVGKPMCLLFEYMAYGDLNEFLRSMSPHTVCSLSHSDLSMRAQVS
MuSK002     LLGVCAVGKPMCLLFEYMAYGDLNEFLRSMSPHTVCSLSHSDLSMRAQVS
MuSK003     ---------------------------------------L---------
MuSK004     LLGMKI-------------------------------------------
MuSK202     LLGVCAVGKPMCLLFEYMAYGDLNEFLRSMSPHTVCSLSHSDLSMRAQVS
```

Figure 10C

```
musk2.01      LLGVCAVGKPMCLLFEYMAYGDLNEFLRSMSPHTVCSLSHSDLSMRAQVS

MuSK001       SPGPPPLSCAEQLCIARQVAAGMAYLSERKFVHRDLATRNCLVGENMVVK
MuSK002       SPGPPPLSCAEQLCIARQVAAGMAYLSERKFVHRDLATRNCLVGENMVVK
MuSK003       --------------------------------------------------
MuSK004       --------------------------------------------------
MuSK202       SPGPPPLSCAEQLCIARQVAAGMAYLSERKFVHRDLATRNCLVGENMVVK
musk2.01      SPGPPPLSCAEQLCIARQVAAGMAYLSERKFVHRDLATRNCLVGENMVVK MuSK001       IADFGLSRNIYSADYYKANENDAIPIRWMPPESIFYNRYTTESDVWAYGV
MuSK002       IADFGLSRNIYSADYYKANENDAIPIRWMPPESIFYNRYTTESDVWAYGV
MuSK003       --------------------------------------------------
MuSK004       --------------------------------------------------
MuSK202       IADFGLSRNIYSADYYKANENDAIPIRWMPPESIFYNRYTTESDVWAYGV
musk2.01      IADFGLSRNIYSADYYKANENDAIPIRWMPPESIFYNRYTTESDVWAYGV MuSK001       VLWEIFSYGLQPYYGMAHEEVIYYVRDGNILSCPENCPVELYNLMRLCWS
MuSK002       VLWEIFSYGLQPYYGMAHEEVIYYVRDGNILSCPENCPVELYNLMRLCWS
MuSK003       ----------------------QLRSFLSCPQ------------------
MuSK004       ---------------------------------------QVRICIS
MuSK202       VLWEIFSYGLQPYYGMAHEEVIYYVRDGNILSCPENCPVELYNLMRLCWS
musk2.01      VLWEIFSYGLQPYYGMAHEEVIYYVRDGNILSCPENCPVELYNLMRLCWS MuSK001       KLPADRPSFTSIHRILERMCERAEGTVSV
MuSK002       KLPADRPSFTSIHRILERMCERAEGTVSV
MuSK003       -----------------------------I
MuSK004       SENRGFPSFSPLVRAF---------SFSP
MuSK202       KLPADRPSFTSIHRILERMCERAEGTVSV
musk2.01      KLPADRPSFTSIHRILERMCERAEGTVSV
```

METHODS FOR TREATING MUSCLE SPECIFIC RECEPTOR KINASE (MUSK) MYASTHENIA GRAVIS WITH THE IG1 DOMAIN OF MUSK

CROSS REFERENCE TO RELATED APPLICATIONS

This application claims priority under 35 USC §119(e) from U.S. Provisional Application Ser. No. 61/877,557, filed Sep. 13, 2013, which application is herein specifically incorporated by reference in its entirety.

GOVERNMENTAL SUPPORT

The research leading to the present invention was funded in part by Grant No. RO1 NS36193 awarded by the National Institutes of Health. The United States government has certain rights in the invention.

FIELD OF INVENTION

Compositions and methods described herein relate to muscle specific kinase (MuSK) and modulation thereof. Agents described herein are envisioned for use as therapeutics to alleviate or delay motor dysfunction in subjects afflicted with a disorder associated with nerve terminal loss or fragmentation. In a particular aspect, the disorder is myasthenia gravis with antibodies to MuSK.

BACKGROUND OF INVENTION

Myasthenia gravis (MG) is an autoimmune disease, caused by auto-antibodies to proteins in the postsynaptic membrane at neuromuscular synapses. Most MG patients carry antibodies to acetylcholine receptors (AChRs), the neurotransmitter receptor at vertebrate neuromuscular synapses (1,2,3). Auto-antibodies to AChRs are largely of the IgG1 and IgG3 subclass (4), which cause muscle weakness by three mechanisms: complement-mediated membrane lysis (5); crosslinking and depletion of cell surface AChRs (6); and to a lesser extent, functional blocking of the ACh-binding site (7). The ability of antibodies to AChRs to recruit complement, dimerize and modulate AChR expression is an important component of their pathogenic mechanism, since animals with experimental autoimmune MG (EAMG) can be rescued from disease with monovalent Fab fragments generated from AChR IgG antibodies and complement-deficient mice are protected against EAMG (8,6,9).

Approximately 20% of patients with MG lack antibodies to AChRs, and approximately 40% of these AChR-negative patients carry auto-antibodies to Muscle specific kinase (MuSK), a receptor tyrosine kinase that is essential for all aspects of synaptic differentiation and maintenance (10,11, 12). The synaptic defects in MuSK MG overlap with those in AChR MG, including a reduction in the number of functional AChRs at synapses and unreliable synaptic transmission, resulting in muscle fatigue and weakness. In contrast to AChR MG, MuSK MG is caused in large part by IgG4 antibodies (13,14,15) that fail to engage complement and are considered functionally monovalent (13,14,15,16). Consequently, the accumulation of complement and muscle membrane damage, hallmark pathological features of AChR MG, appear insignificant in MuSK MG (13,17). Despite the paucity or absence of complement and cell damage in MuSK MG, the structural and functional deficits of synapses are extensive in MuSK MG, which highlights the key role that MuSK plays in organizing all aspects of synaptic differentiation (10,18).

AChR clustering and synapse formation are orchestrated by neuronally released Agrin, which binds to Lrp4, a member of the low density lipoprotein-related protein family, causing Lrp4 to bind and activate MuSK (19,20,21). Once tyrosine-phosphorylated, MuSK recruits Dok-7, an adaptor protein that becomes phosphorylated and recruits additional signaling molecules essential for synapse formation (22,23, 24).

The extracellular region of MuSK contains three Ig-like domains and a Frizzled-like domain (10). The first Ig-like domain in MuSK is required for MuSK to bind Lrp4. Mutation of a single residue, I96, on a solvent exposed surface of the first Ig-like domain, prevents MuSK from binding Lrp4 and responding to Agrin (25,21). A hydrophobic surface on the opposite side of the first Ig-like domain mediates MuSK homodimerization, essential for MuSK trans-phosphorylation (25). Although MuSK is expressed by muscle and not by motor neurons, MuSK is essential for presynaptic as well as postsynaptic differentiation (10). In mice lacking MuSK, motor axons fail to stop and differentiate and instead wander aimlessly throughout the muscle (11). MuSK regulates presynaptic differentiation by clustering Lrp4 in muscle, which functions bi-directionally by serving not only as a receptor for Agrin and a ligand for MuSK, but also as a direct retrograde signal for presynaptic differentiation (26). In addition to its role during synapse formation, MuSK is also required to maintain adult synapses, as inhibition of MuSK expression in adult muscle leads to profound defects in presynaptic and postsynaptic differentiation (27,28).

In view of the above, a better understanding of MuSK activity and its role in the neuromuscular synapse in healthy and pathological states is an objective that serves a profound need. The need is underscored by the fact that MuSK MG is a debilitating autoimmune disease and one third of MuSK MG patients experience a life-threatening respiratory crisis. Long-term immunosuppression is the only current treatment option and the side effects of such an approach are considerable.

The citation of references herein shall not be construed as an admission that such is prior art to the present invention.

SUMMARY OF THE INVENTION

Myasthenia gravis (MG) is a severely debilitating autoimmune disease that is due to a decrease in the efficiency of synaptic transmission at neuromuscular synapses. MG is caused by antibodies against postsynaptic proteins, including (1) acetylcholine receptors (AChRs), the neurotransmitter receptor, (2) muscle specific kinase (MuSK), a receptor tyrosine kinase essential for the formation and maintenance of neuromuscular synapses, and (3) lipoprotein-related protein 4 (Lrp4), which responds to neural Agrin by binding and stimulating MuSK. Passive transfer studies in mice have shown that IgG4 antibodies from MuSK MG patients cause disease without requiring complement or other immune components, suggesting that these MuSK antibodies cause disease by directly interfering with MuSK function. The present inventors have discovered that pathogenic IgG4 antibodies to MuSK bind to a structural epitope in the first Ig-like domain of MuSK, prevent binding between MuSK and Lrp4 and inhibit Agrin-stimulated MuSK phosphorylation. In contrast, these IgG4 antibodies have little or no direct effect on MuSK dimerization or MuSK internalization. Accordingly, these results provide insight into the unique pathogenesis of MuSK MG and provide clues toward development of specific treatment options.

In a first aspect, a method for improving motor function in a subject afflicted with muscle specific receptor kinase myasthenia gravis (MuSK-MG) is presented, the method comprising: administering a muscle specific receptor kinase (MuSK) first immunoglobulin-like domain 1 (Ig1) domain decoy that binds to IgG4 antibodies specific for the Ig1 domain of MuSK to the subject in a therapeutically effective amount sufficient to increase MuSK activity in the subject and thereby improve motor function in the subject with MuSK-MG.

In a second aspect, a method for preserving neuromuscular synapses in a subject afflicted with muscle specific receptor kinase myasthenia gravis (MuSK-MG) is presented, the method comprising: administering a muscle specific receptor kinase (MuSK) first immunoglobulin-like domain 1 (Ig1) domain decoy that binds to IgG4 antibodies specific for the Ig1 domain of MuSK to the subject in a therapeutically effective amount sufficient to increase MuSK activity in the subject and thereby preserve neuromuscular synapses in the subject.

In a third aspect, a method for treating a subject afflicted with muscle specific receptor kinase myasthenia gravis (MuSK-MG) is presented, the method comprising: administering a muscle specific receptor kinase (MuSK) first immunoglobulin-like domain 1 (Ig1) domain decoy that binds to IgG4 antibodies specific for the Ig1 domain of MuSK to the subject in a therapeutically effective amount sufficient increase MuSK activity in the subject and thereby treat the subject with MuSK-MG.

In a particular embodiment of the aforementioned methods, the MuSK Ig1 domain decoy is a polypeptide, an antibody or antibody fragment, a chemical compound, or a small molecule. In a particular embodiment, the polypeptide comprises the Ig1 domain of MuSK.

In a more particular embodiment, the polypeptide is the Ig1 domain of MuSK. In an even more particular embodiment, the polypeptide is a mutated Ig1 domain of MuSK comprising at least one mutation that reduces ability of the mutated Ig1 domain to bind Lrp4. More particularly still, the mutated Ig1 domain of MuSK comprises a mutation whereby alanine (A) replaces isoleucine (I) at amino acid position 96 of MuSK. In another particular embodiment, the mutated Ig1 domain of MuSK comprises a mutation whereby alanine (A) or asparagine (N) replaces threonine (T) at amino acid position 36 of MuSK and/or a mutation whereby lysine (K) replaces alanine (A) at amino acid position 114 of MuSK. In a further embodiment, the mutated Ig1 domain of MuSK comprises at least one of the mutations described herein.

In a particular embodiment, the Ig1 domain decoy comprises, consists essentially of, or consists of the amino acid sequence of PVITTPLETVDALVEEVATFMCAVESYPQPEIS WTRNKILIKLFDTRYSIRENGQLLTILSVED SDD GIYCCTANNGVGGAVESCGALQV (SEQ ID NO: 19). An Ig1 domain decoy comprising, consisting essentially of, or consisting of SEQ ID NO: 19 may, moreover, comprise at least one of the aforementioned mutations.

In an another embodiment, the Ig1 domain decoy comprises, consists essentially of, or consists of the amino acid sequence from leucine at amino acid position 24 to methionine at amino acid position 119 of SEQ ID NO: 2. An Ig1 domain decoy comprising, consisting essentially of, or consisting of amino acids spanning positions 24-119 of SEQ ID NO: 2 may, moreover, comprise at least one of the aforementioned mutations. See also Stiegler et al. (2006, J Mol Biol 364:424-433).

In an another embodiment, the Ig1 domain decoy comprises, consists essentially of, or consists of the amino acid sequence spanning amino acids 21-125 of SEQ ID NO: 2. An Ig1 domain decoy comprising, consisting essentially of, or consisting of amino acids spanning positions 21-125 of SEQ ID NO: 2 may, moreover, comprise at least one of the aforementioned mutations.

As described herein, the MuSK polypeptides such as the Ig1 domain and mutants thereof may be used as decoys to bind pathogenic IgG4 antibodies, as antigens in methods designed to induce mucosal tolerance, and/or in devices for use in connection with plasmapheresis, whereby pathogenic IgG4 antibodies specific for the MuSK Ig1 domain are depleted from plasma prior to re-introduction into the subject undergoing plasmapheresis for the treatment of MuSK-MG.

In an embodiment, the method further comprises measuring blood, serum, and/or cerebrospinal fluid levels of IgG4 antibodies specific for the Ig1 domain of MuSK in the subject before and after administering the MuSK Ig1 domain decoy and/or measuring levels of IgG4 antibodies specific for the Ig1 domain of MuSK in the subject at motor endplates before and after administering the MuSK Ig1 domain decoy.

In an embodiment of the method, the therapeutically effective amount of the MuSK Ig1 domain decoy reduces levels of IgG4 antibodies specific for the Ig1 domain of MuSK.

In another embodiment of the method, the improvement in motor function is measurable by determining innervation levels. Electromyography (EMG), for example, can be performed to assess motor function and/or innervation levels. EMG may be performed on facial muscles [such as, e.g., musculus nasalis (m. nasalis)], neck or shoulder muscles (such as, e.g., m. trapezius), and/or hand muscles (such as, e.g., m. abductor minimi). Single fiber electromyography may be performed on facial muscles (such as, e.g., m. orbicularis oculi) or arm muscles.

In yet another embodiment of the method, the MuSK Ig1 domain decoy maintains innervation levels in the subject.

In a further embodiment of the method, the MuSK Ig1 domain decoy stabilizes motor axon synapses or increases the number of motor axon synapses in the subject.

In a further embodiment, the subject is a mammal and is more particularly a primate. In a more particular embodiment, the subject is a human.

Also encompassed herein is a use of a muscle specific receptor kinase (MuSK) first immunoglobulin-like domain 1 (Ig1) domain decoy in the preparation of a medicament for improving motor function in muscle specific receptor kinase myasthenia gravis (MuSK-MG), wherein the medicament is administered to a subject afflicted with MuSK in a therapeutically effective amount that increases MuSK activity in the subject and thereby improves motor function in the subject.

Also encompassed herein is a use of a muscle specific receptor kinase (MuSK) first immunoglobulin-like domain 1 (Ig1) domain decoy in the preparation of a medicament for preserving neuromuscular synapses in muscle specific receptor kinase myasthenia gravis (MuSK-MG), wherein the medicament is administered to a subject afflicted with MuSK in a therapeutically effective amount that increases MuSK activity in the subject and thereby preserves neuromuscular synapses in the subject.

Also encompassed herein is a use of a muscle specific receptor kinase (MuSK) first immunoglobulin-like domain 1 (Ig1) domain decoy in the preparation of a medicament for treating muscle specific receptor kinase myasthenia gravis (MuSK-MG), wherein the medicament increases MuSK activity and thereby treats MuSK-MG.

In a further aspect, an agent that acts as a muscle specific receptor kinase (MuSK) first immunoglobulin-like domain 1 (Ig1) domain decoy for use in delaying motor dysfunction in muscle specific receptor kinase myasthenia gravis (MuSK-MG) is presented, wherein the agent is administered to a subject afflicted with MuSK in a therapeutically effective amount sufficient to increase MuSK activity in the subject and thereby improve motor function in the subject.

In another further aspect, an agent that acts as a muscle specific receptor kinase (MuSK) first immunoglobulin-like domain 1 (Ig1) domain decoy for use in preserving neuromuscular synapses in muscle specific receptor kinase myasthenia gravis (MuSK-MG) is presented, wherein the agent is administered to a subject afflicted with MuSK in a therapeutically effective amount sufficient to increase MuSK activity in the subject and thereby preserve neuromuscular synapses in the subject.

In a still further aspect, an agent that acts as a muscle specific receptor kinase (MuSK) first immunoglobulin-like domain 1 (Ig1) domain decoy for use in treating muscle specific receptor kinase myasthenia gravis (MuSK-MG) is presented, wherein the agent is administered to a subject afflicted with MuSK in a therapeutically effective amount sufficient to increase MuSK activity in the subject and thereby treat MuSK-MG in the subject.

With respect to the aforementioned uses and agents, the agent may be a polypeptide, an antibody or antibody fragment, a chemical compound, or a small molecule. In a particular embodiment thereof, the polypeptide comprises the Ig1 domain of MuSK. In a more particular embodiment, the polypeptide is the Ig1 domain of MuSK. In an even more particular embodiment, the polypeptide is a mutated Ig1 domain of MuSK comprising at least one mutation that reduces ability of the mutated Ig1 domain to bind Lrp4. More particularly still, the mutated Ig1 domain of MuSK comprises a mutation whereby alanine (A) replaces isoleucine (I) at amino acid position 96 of MuSK. In another particular embodiment, the mutated Ig1 domain of MuSK comprises a mutation whereby alanine (A) or asparagine (N) replaces threonine (T) at amino acid position 36 of MuSK and/or a mutation whereby lysine (K) replaces alanine (A) at amino acid position 114 of MuSK. In a further embodiment, the mutated Ig1 domain of MuSK comprises at least one of the mutations described herein.

Uses and agents described herein may further comprise measuring blood, serum, and/or cerebrospinal fluid levels of IgG4 antibodies specific for the Ig1 domain of MuSK before and after use of the MuSK Ig1 domain decoy and/or measuring levels of IgG4 antibodies specific for the Ig1 domain of MuSK in the subject at motor endplates before and after administering the MuSK Ig1 domain decoy.

In a particular embodiment thereof, use of the therapeutically effective amount of the MuSK Ig1 domain decoy or medicament reduces levels of IgG4 antibodies specific for the Ig1 domain of MuSK.

In a more particular embodiment thereof, the improvement in motor function is measurable by determining innervation levels. As described herein, EMG may be used to assess motor function and/or muscle innervation.

In another particular embodiment thereof, the medicament or agent maintains innervation levels in the subject.

In yet another embodiment thereof, the medicament or agent stabilizes motor axon synapses or increases the number of motor axon synapses in the subject.

With regard to the use or agent, the subject may be a mammal and is more particularly a primate. More particularly, the subject is a human.

Also encompassed herein is a method for screening to identify an agent that inhibits binding of IgG4 antibodies specific for muscle specific receptor kinase (MuSK) first immunoglobulin-like domain 1 (Ig1) domain to the MuSK Ig1 domain, the method comprising: contacting the IgG4 antibodies with at least one agent in vitro and assaying binding between the IgG4 antibodies and the MuSK Ig1 domain, wherein a reduction in the binding of the IgG4 antibodies to the MuSK Ig1 domain in the presence of the at least one agent relative to binding following contacting with a control agent identifies the at least one agent as an inhibitor of the binding of the IgG4 antibodies to the MuSK Ig1 domain.

In an embodiment thereof, the at least one agent is a polypeptide, an antibody or antibody fragment, a chemical compound, or a small molecule.

In a more particular embodiment thereof, the at least one agent binds to the IgG4 antibodies.

In another aspect, a method for preparing muscle specific receptor kinase (MuSK) antibody-depleted plasma is presented, the method comprising contacting plasma isolated from a subject afflicted with MuSK myasthenia gravis (MuSK-MG) with a MuSK first immunoglobulin-like domain 1 (Ig1) domain decoy to generate complexes comprising the MuSK Ig1 domain decoy and antibodies immunospecific for the MuSK Ig1 domain decoy; and separating the complexes from the plasma to generate MuSK antibody-depleted plasma.

In an embodiment thereof, the MuSK Ig1 domain decoy is immobilized prior to or after generation of complexes. In a particular embodiment thereof, the MuSK Ig1 domain decoy is immobilized on a solid surface. Exemplary solid surfaces are known in the art and include: sepharose, silica, and microporous cellulose beads.

In a further embodiment, the MuSK antibody-depleted plasma is administered to the subject afflicted with MuSK-MG from which the plasma was isolated to improve motor function in the subject, preserve neuromuscular synapses in the subject, and/or treat the subject.

In another embodiment, use of the MuSK antibody-depleted plasma in the preparation of a medicament for improving motor function in MuSK-MG, preserving neuromuscular synapses in MuSK-MG, and/or treating MuSK-MG is envisioned.

In yet another embodiment, the MuSK antibody-depleted plasma is envisioned for use in improving motor function in MuSK-MG, for use in preserving neuromuscular synapses in MuSK-MG, and/or for use in treating MuSK-MG.

Other objects and advantages will become apparent to those skilled in the art from a review of the following description which proceeds with reference to the following illustrative drawings.

BRIEF DESCRIPTION OF THE DRAWINGS

FIG. 2. MuSK MG IgG4 antibodies block binding between Lrp4 and MuSK and inhibit Agrin-stimulated MuSK phosphorylation in muscle. (a) IgG4 antibodies from MuSK MG patients, but not healthy controls inhibit Agrin-dependent binding between MuSK and Lrp4. Patient numbers are indicated. (b) IgG1-3 from the MuSK MG patients and healthy controls moderately and equally reduce association between MuSK and Lrp4. (c) Mutation of MuSK I96 fails to reduce binding of AP-ecto-MuSK to IgG4 antibodies from patient #17 [additional experiments and statistical analysis reveal that the difference is not significant]. (d) IgG4 antibodies from MuSK MG patients but not from an AChR MG patient or a healthy control inhibit Agrin-stimulated MuSK phosphorylation in C2 myotubes. (e) IgG4 antibodies from MuSK MG patients reduce MuSK phosphorylation, which was normalized to the level of immunoprecipitated MuSK (*, $p<0.05$, n=3; duplicate samples); patient antibodies to MuSK enhance the amount of MuSK that is immunoprecipitated.

FIGS. 5A and B. Nucleic and amino acid sequences of human MuSK. The nucleic acid sequence is designated SEQ ID NO: 1 and the amino acid sequence is designated SEQ ID NO: 2.

FIGS. 6A and B. Eukaryotic mutant expression vectors. Nucleic and amino acid sequences included in the various constructs described herein are presented and are correspondingly color coded. The color coding is based on crystal structure analyses. The color coding is as follows: Grey: signal sequence; Green: hypothetical Ig1 domain; Blue: hypothetical Ig2 domain; Purple: hypothetical Ig3 domain; Yellow: predicted Fz domain.

FIG. 7. Vector sequences. Amino acid sequences of MuSK included in the indicated vectors are presented. Experiments performed using these vectors revealed that MuSK-MG patient antibody binding to MuSK is reduced when the Ig-like 1 domain is deleted.

FIGS. 10 A, B, and C. An alignment of the amino acid sequences of different MuSK isoforms is presented. MuSK001 (SEQ ID NO: 22), MuSK002 (SEQ ID NO: 23), MuSK2.01 (SEQ ID NO: 27) and MuSK202 (SEQ ID NO: 26) all have the same Ig1 domain. The other 2 isoforms, MuSK003 (SEQ ID NO: 24) and MuSK004 (SEQ ID NO: 25), are truncated and do not comprise this domain of full length MuSK or only comprise portions thereof.

DETAILED DESCRIPTION OF THE INVENTION

Figure 1:
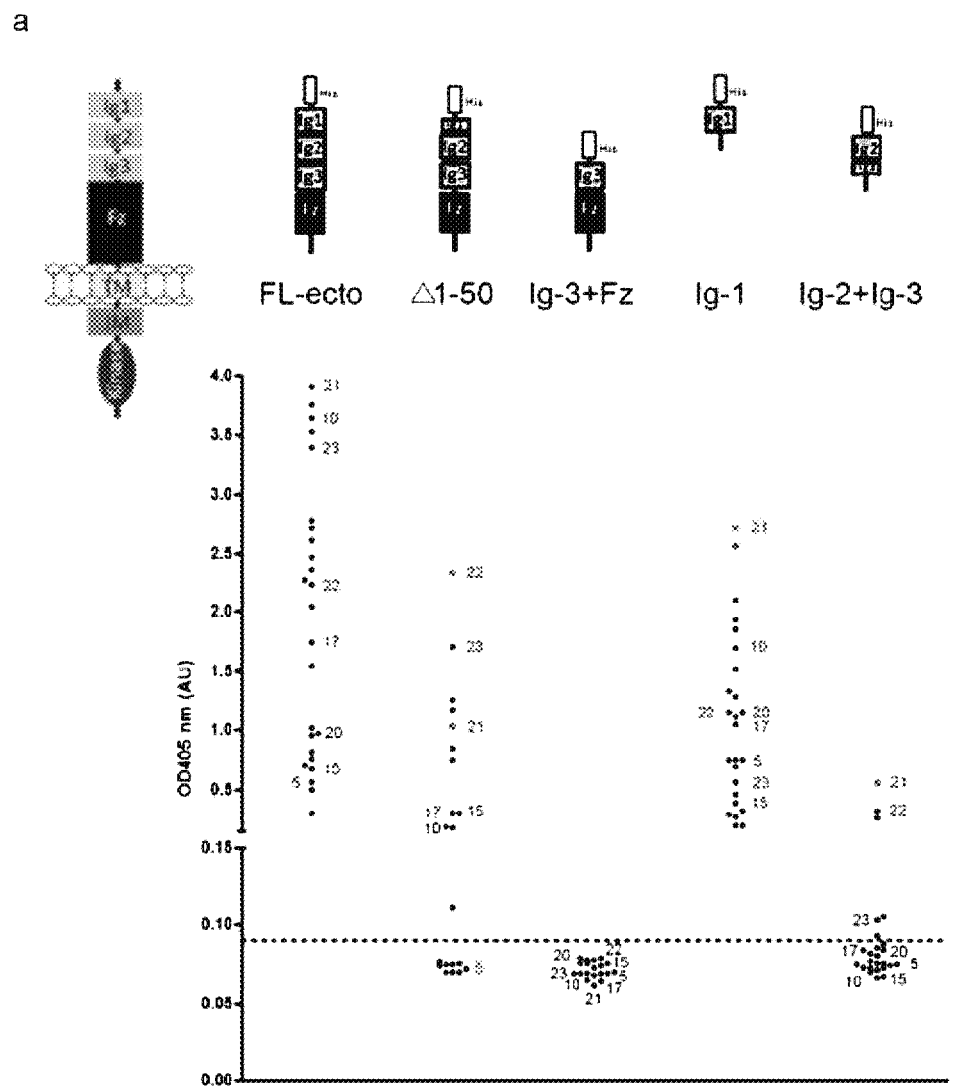
FIG. 1. MuSK MG IgG4 antibodies bind predominantly to the first Ig-like domain in MuSK. (a) Antibodies from all 25 patients bind to the extracellular region of MuSK. The predominant binding sites reside in the first Ig-like domain, as antibodies bind to this domain nearly as well as the entire extracellular region. Moreover, deletion of the N-terminal half of the first Ig-like domain substantially reduces antibody-binding. Antibodies from five patients have additional reactivity to the second Ig-like domain. (b,c) Antibodies that bind selectively to the first Ig-like domain stain cells expressing full-length MuSK-GFP but not ΔIg-like 1-MuSK-GFP, whereas antibodies with additional reactivity bind to cells expressing either construct. (d) Antibody-binding to the extracellular region of MuSK is strongly inhibited by the first Ig-like domain but poorly by 20-mer overlapping peptides from this domain. Peptides covering amino acids 64-104 reduce binding by 5-10%.
Figure 1:
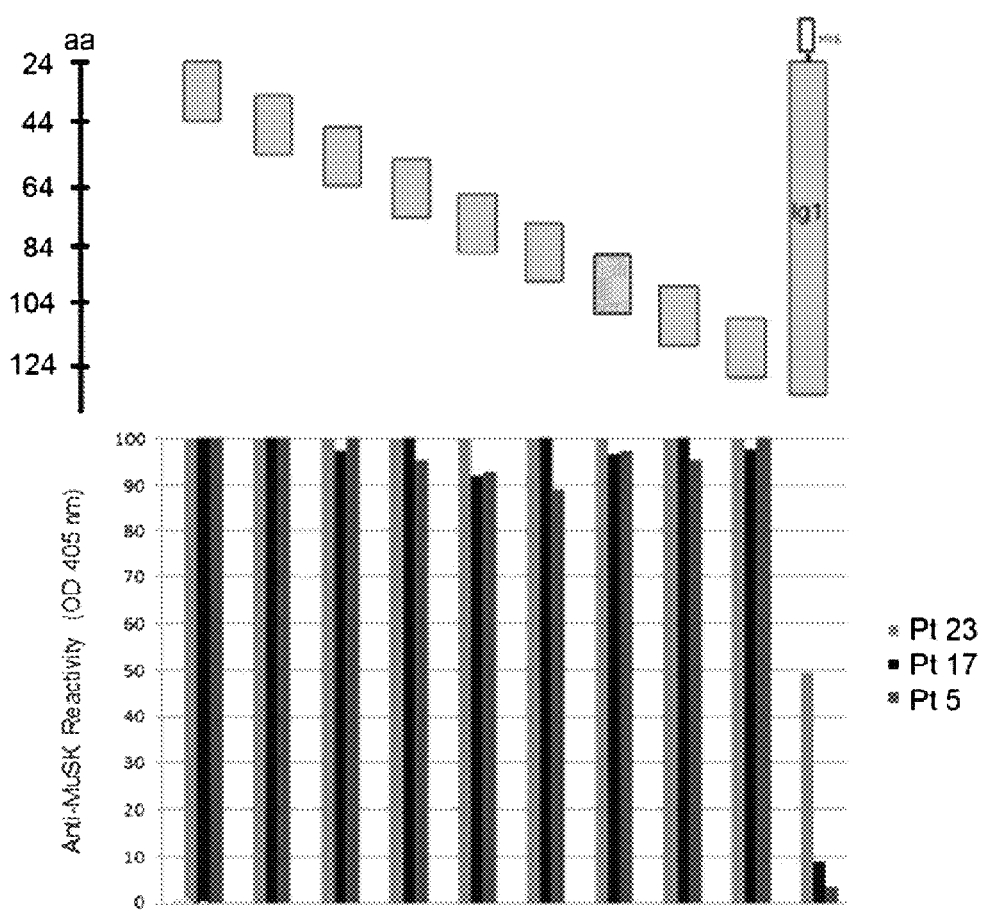

The present inventors have discovered that pathogenic human IgG4 MuSK antibodies bind to the first Ig-like domain (Ig1) in MuSK and prevent Lrp4 from binding MuSK, thereby inhibiting Agrin-stimulated MuSK phosphorylation. This inhibitory mechanism is likely responsible for disrupting the structure of the synapse, compromising synaptic transmission and causing disease. Findings presented herein therefore suggest that therapeutic strategies designed to increase MuSK activity may prove effective in treating MuSK MG. Moreover, studies presented herein provide the first mechanistic understanding of an IgG4-mediated autoimmune disease and may shed light on the mechanisms of other IgG4-mediated autoimmune diseases.

Further to the above, the present inventors propose that the pathogenic effects of the MuSK antibodies can be reduced or prevented by using a decoy Ig-like domain from MuSK. Accordingly, methods for treating MuSK MG using decoy MuSK Ig-like domains are proposed herein. Further to this objective, muscle cell culture and passive transfer assays are ongoing to assess the ability of decoy Ig-like domains of MuSK to reduce and/or prevent pathogenic effects of MuSK antibodies.

As described herein, the first Ig-like domain in MuSK is critical for MuSK association with Lrp4, which stimulates MuSK tyrosine phosphorylation. All MuSK MG patients studied have antibodies which bind to the first Ig-like domain in MuSK and prevent association between MuSK and Lrp4. Thus, the first Ig-like domain (Ig1) from MuSK or a variant or truncation thereof, presented on its own or together with an inert carrier, serves as a decoy or trap to sequester antibodies that would otherwise interfere with association between MuSK and Lrp4 and inhibit MuSK tyrosine phosphorylation in the biological context of MuSK MG. In so doing, the decoy first Ig-like domain of MuSK would restore MuSK signaling in a MuSK MG patient by acting as a sponge that binds pathogenic MuSK antibodies. Because the first Ig-like domain from MuSK may, however, bind to Lrp4 and interfere with the association of Lrp4 and MuSK, the present inventors envision using a mutated MuSK first Ig-like domain as a therapeutic agent for the treatment of MuSK. More particularly, the present inventors envision that a mutated MuSK first Ig-like domain that can be used as an effective decoy maintains its ability to bind and sequester antibodies from MuSK MG patients, but is impaired with respect to its ability to bind Lrp4 and interfere with normal Lrp4-MuSK association.

In a particular embodiment thereof, one such alteration would comprise the first Ig-like domain of MuSK that comprises a mutation of I96. In an embodiment thereof, the mutation of isoleucine at amino acid position 96 results in a substitution of any amino acid at amino acid position 96 of MuSK, except for leucine or valine (hydrophobics of approximately the same size as isoleucine). The crystal structure of MuSK and various functional assays suggest that the aforementioned mutations of I96 will abrogate Lrp4 and MuSK binding (25, 27). In a more particular embodiment thereof, the mutation results in a substitution of Alanine for Isoleucine at I96, which substitution abrogates Lrp4 and MuSK binding. Accordingly, mutated MuSK first Ig-like domains comprising alanine at amino acid 96 are envisioned as MuSK antibody traps or decoys as is their use in compositions, methods, uses, and medicaments described herein.

In other embodiments, a mutated MuSK first Ig-like domain comprising a mutation of a different residue or residues on the same surface as I96, such as T36 and/or A114, is envisioned. In that this surface is known to act as an interface with Lrp4, a mutated MuSK first Ig-like domain comprising a mutation at, for example, T36 and/or A114 is likely to be effective in binding pathogenic IgG4 antibodies, but ineffective with respect to interfering with binding between Lrp4 and endogenous MuSK expressed on the cell surface. In a particular embodiment of a mutation of the threonine at amino acid position 36, the mutation is T36N or T36A. In another particular embodiment, the mutation of the alanine at amino acid position 114 is A114K. These two residues are near Ile96 topologically and are, therefore, predicted to contribute to MuSK interactions with Lrp4. Underscoring their significance, T36 and A114 are conserved in the first Ig-like domain of MuSK across various species, whereas the amino acids at corresponding positions in the second Ig-like domain of MuSK differ. Indeed, the amino acid at corresponding position 36 in the second Ig-like domain of MuSK is asparagine (N) and the amino acid at corresponding position 114 is lysine (K).

Figure 9:
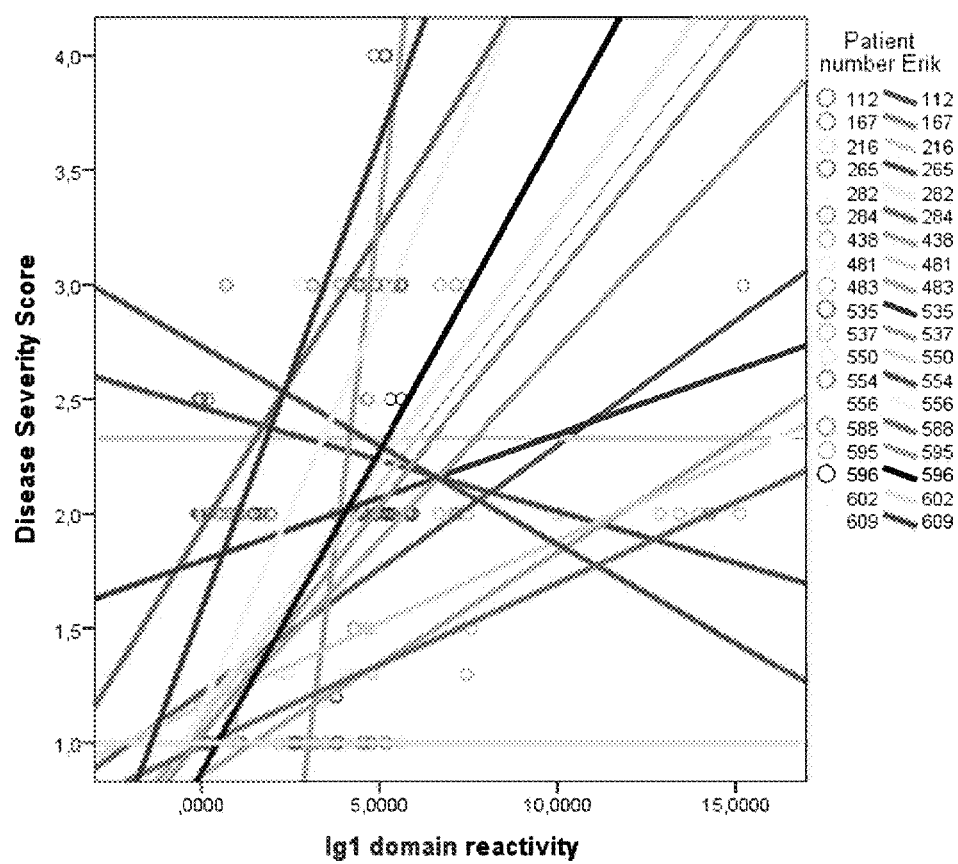
FIG. 9. Reactivity level against the N-terminal MuSK domain positively predicts disease severity in MuSK MG patients. Each line represents the correlation in one patient for a longitudinal sample set.

To investigate further the importance of the main immunogenic region at the Ig-like 1 domain of MuSK, the present inventors evaluated whether epitope spreading occurred in longitudinal samples of 31 unique MuSK MG patients. Epitope spreading occurred in less than 20% of the MuSK MG patients tested, suggesting that changes in the epitope repertoire are relatively rare. The present inventors also assessed whether disease severity correlated with the reactivity against any of the particular MuSK domains. A linear mixed effect model confirmed that reactivity against the N-terminal part of MuSK significantly correlates (average β-coefficient 0.159, p=0,000) with disease severity as scored by the DSS score from Niks et al. (Niks 2008 J Neuroimmun). See FIG. 9. Reactivity to any of the other domains of MuSK did not significantly contribute to disease severity.

These data support the idea that antibodies that bind to the N-terminal part of MuSK inhibit its function and thereby cause MuSK-Mg, which provides a further rational for specific elimination of these pathogenic autoantibodies. The protein that was used for this evaluation was a MuSK peptide spanning amino acids 21-125 as follows:

```
                                       (SEQ ID NO: 20)
TEKLPKAPVITTPLETVDALVEEVATFMCAVESYPQPEISWTRNKILIKL

FDTRYSIRENGQLLTILSVEDSDDGIYCCTANNGVGGAVESCGALQVKMK

PKITR.
```

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A. TERMINOLOGY

The term "specific binding member" describes a member of a pair of molecules, which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organization of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. This application is concerned with antigen-antibody type reactions.

The term "antibody" describes an immunoglobulin whether natural or partly or wholly synthetically produced. The term also covers any polypeptide or protein having a binding domain, which is, or is homologous to, an antibody binding domain. CDR grafted antibodies are also contemplated by this term. An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567. The term "antibody(ies)" includes a wild type immunoglobulin (Ig) molecule, generally comprising four full length polypeptide chains, two heavy (H) chains and two light (L) chains, or an equivalent Ig homologue thereof (e.g., a camelid nanobody, which comprises only a heavy chain); including full length functional mutants, variants, or derivatives thereof, which retain the essential epitope binding features of an Ig molecule, and including dual specific, bispecific, multispecific, and dual variable domain antibodies; Immunoglobulin molecules can be of any class (e.g., IgG, IgE, IgM, IgD, IgA, and IgY), or subclass (e.g., IgG1, IgG2, IgG3, IgG4, IgA1, and IgA2). Also included within the meaning of the term "antibody" is any "antibody fragment".

An "antibody fragment" means a molecule comprising at least one polypeptide chain that is not full length, including (i) a Fab fragment, which is a monovalent fragment consisting of the variable light (VL), variable heavy (VH), constant light (CL) and constant heavy 1 (CH1) domains; (ii) a F(ab')2 fragment, which is a bivalent fragment comprising two Fab fragments linked by a disulfide bridge at the hinge region; (iii) a heavy chain portion of an Fab (Fd) fragment, which consists of the VH and CH1 domains; (iv) a variable fragment (Fv) fragment, which consists of the VL and VH domains of a single arm of an antibody, (v) a domain antibody (dAb) fragment, which comprises a single variable domain (Ward, E. S. et al., Nature 341, 544-546 (1989)); (vi) a camelid antibody; (vii) an isolated complementarity determining region (CDR); (viii) a Single Chain Fv (ScFv) Fragment wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (ix) a diabody, which is a bivalent, bispecific antibody in which VH and VL domains are expressed on a single polypeptide chain, but using a linker that is too short to allow for pairing between the two domains on the same chain, thereby forcing the domains to pair with the complementarity domains of another chain and creating two antigen binding sites (WO94/13804; P. Holliger et al Proc. Natl. Acad. Sci. USA 90 6444-6448, (1993)); and (x) a linear antibody, which comprises a pair of tandem Fv segments (VH-CH1-VH-CH1) which, together with complementarity light chain polypeptides, form a pair of antigen binding regions; (xi) multivalent antibody fragments (scFv dimers, trimers and/or tetramers (Power and Hudson, J Immunol. Methods 242: 193-204 9 (2000)); and (xii) other non-full length portions of heavy and/or light chains, or mutants, variants, or derivatives thereof, alone or in any combination.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023 and U.S. Pat. Nos. 4,816,397 and 4,816,567.

An "antibody combining site" is that structural portion of an antibody molecule comprised of light chain or heavy and light chain variable and hypervariable regions that specifically binds antigen.

The term "variable" refers to the fact that certain portions of the variable domains differ extensively in sequence among antibodies and are used in the binding and specificity of each particular antibody for its particular antigen. Variability is not, however, evenly distributed throughout antibody variable domains and is concentrated in three segments called complementarity determining regions (CDRs) or hypervariable regions which are found in both the light chain and heavy chain variable domains. The more highly conserved portions of variable domains are referred to as the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of an antibody. The constant domains are not involved directly in antigen binding, but exhibit various effector functions, such as participation of the antibody in antibody-dependent cellular toxicity.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contain the paratope, including those portions known in the art as Fab, Fab', F(ab')$_2$ and F(v), which portions are preferred for use in the therapeutic methods described herein.

Antibodies may also be bispecific, wherein one binding domain of the antibody is a specific binding member of the invention, and the other binding domain has a different specificity, e.g. to recruit an effector function or the like. Bispecific antibodies of the present invention include wherein one binding domain of the antibody is a specific binding member of the present invention, including a fragment thereof, and the other binding domain is a distinct antibody or fragment thereof, including that of a distinct anti-growth hormone receptor specific antibody. The other binding domain may be an antibody that recognizes or targets a particular cell type, as in a muscle, neural or glial cell-specific antibody. In the bispecific antibodies of the present invention the one binding domain of the antibody of the invention may be combined with other binding domains or molecules which recognize particular cell receptors and/or modulate cells in a particular fashion, as for instance an immune modulator (e.g., interleukin(s)), a growth modulator or cytokine, or mitotic agent or factor.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may also contain an antibody molecule having a plurality of antibody combining sites, each immunospecific for a different antigen; e.g., a bispecific (chimeric) monoclonal antibody.

The term "antigen binding domain" describes the part of an antibody which comprises the area which specifically binds to and is complementary to part or all of an antigen. Where an antigen is large, an antibody may bind to a particular part of the antigen only, which part is termed an epitope. An antigen binding domain may be provided by one or more antibody variable domains. Preferably, an antigen binding domain comprises an antibody light chain variable region (VL) and an antibody heavy chain variable region (VH).

The term "specific" may be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

As used herein, the term "immunomodulator" refers to an agent which is able to modulate an immune response. An example of such modulation is an enhancement of cell activation or of antibody production.

An "immunological response" to a composition or vaccine comprised of an antigen is the development in the host of a cellular- and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

The term "comprise" is generally used in the sense of include, that is to say permitting the presence of one or more features or components.

The term "consisting essentially of" refers to a product, particularly a peptide sequence, of a defined number of residues which is not covalently attached to a larger product. In the case of the peptide of the invention referred to above, those of skill in the art will appreciate that minor modifications to the N- or C-terminal of the peptide may however be contemplated, such as the chemical modification of the terminal to add a protecting group or the like, e.g. the amidation of the C-terminus.

Agents or compounds described herein may, therefore, comprise the MuSK Ig1 domain and mutants thereof as described herein, consist essentially of the MuSK Ig1 domain and mutants thereof as described herein, and/or consist of the MuSK Ig1 domain and mutants thereof as described herein. An agent or compound consisting essentially of or consisting of the MuSK Ig1 domain may comprise one or more of the mutations described herein that are involved in MuSK binding to Lrp4.

The term "isolated" refers to the state in which specific binding members of the invention or nucleic acid encoding such binding members will be, in accordance with the present invention. Members and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practiced in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy.

As used herein, "pg" means picogram, "ng" means nanogram, "ug" or "μg" mean microgram, "mg" means milligram, "ul" or "μl" mean microliter, "ml" means milliliter, "l" means liter.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

| TABLE OF CORRESPONDENCE | | |
|---|---|---|
| SYMBOL | | AMINO |
| 1-Letter | 3-Letter | ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding protein or peptide sequences as provided herein, or comprising sequences which are degenerate thereto. DNA sequences having the nucleic acid sequence encoding the peptides of the invention are contemplated, including degenerate sequences thereof encoding the same, or a conserved or substantially similar, amino acid sequence. By "degenerate to" is meant that a different three-letter codon is used to specify a particular amino acid. It is well known in the art that the following codons can be used interchangeably to code for each specific amino acid:

Phenylalanine (Phe or F) UUU or UUC
Leucine (Leu or L) UUA or UUG or CUU or CUC or CUA or CUG
Isoleucine (Ile or I) AUU or AUC or AUA
Methionine (Met or M) AUG
Valine (Val or V) GUU or GUC of GUA or GUG
Serine (Ser or S) UCU or UCC or UCA or UCG or AGU or AGC
Proline (Pro or P) CCU or CCC or CCA or CCG
Threonine (Thr or T) ACU or ACC or ACA or ACG
Alanine (Ala or A) GCU or GCG or GCA or GCG
Tyrosine (Tyr or Y) UAU or UAC
Histidine (His or H) CAU or CAC
Glutamine (Gln or Q) CAA or CAG
Asparagine (Asn or N) AAU or AAC Lysine (Lys or K) AAA or AAG
Aspartic Acid (Asp or D) GAU or GAC
Glutamic Acid (Glu or E) GAA or GAG
Cysteine (Cys or C) UGU or UGC
Arginine (Arg or R) CGU or CGC or CGA or CGG or AGA or AGG
Glycine (Gly or G) GGU or GGC or GGA or GGG
Tryptophan (Trp or W) UGG
Termination codon UAA (ochre) or UAG (amber) or UGA (opal)

It should be understood that the codons specified above are for RNA sequences. The corresponding codons for DNA have a T substituted for U.

Mutations can be made in the sequences encoding the protein or peptide sequences of the invention, such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:
Amino Acids with Nonpolar R Groups
Alanine, Valine, Leucine, Isoleucine, Proline, Phenylalanine, Tryptophan, Methionine
Amino Acids with Uncharged Polar R Groups
Glycine, Serine, Threonine, Cysteine, Tyrosine, Asparagine, Glutamine
Amino Acids with Charged Polar R Groups (Negatively Charged at pH 6.0)
Aspartic acid, Glutamic acid
Basic Amino Acids (Positively Charged at pH 6.0)
Lysine, Arginine, Histidine (at pH 6.0)
Another grouping may be those amino acids with phenyl groups:
Phenylalanine, Tryptophan, Tyrosine
Particularly preferred substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free $NH_2$ can be maintained.

Exemplary and preferred conservative amino acid substitutions include any of: glutamine (Q) for glutamic acid (E) and vice versa; leucine (L) for valine (V) and vice versa; serine (S) for threonine (T) and vice versa; isoleucine (I) for valine (V) and vice versa; lysine (K) for glutamine (Q) and vice versa; isoleucine (I) for methionine (M) and vice versa; serine (S) for asparagine (N) and vice versa; leucine (L) for methionine (M) and vice versa; lysine (L) for glutamic acid (E) and vice versa; alanine (A) for serine (S) and vice versa; tyrosine (Y) for phenylalanine (F) and vice versa; glutamic acid (E) for aspartic acid (D) and vice versa; leucine (L) for isoleucine (I) and vice versa; lysine (K) for arginine (R) and vice versa.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces beta-turns in the protein's structure.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined $T_m$ with washes of higher stringency, if desired.

The term 'agent' means any molecule, including polypeptides, antibodies, polynucleotides, chemical compounds and small molecules. In particular the term agent includes compounds such as test compounds or drug candidate compounds.

The term 'agonist' refers to a ligand that stimulates the receptor the ligand binds to in the broadest sense or stimulates a response that would be elicited on binding of a natural binder to a binding site.

The term 'assay' means any process used to measure a specific property of a compound or agent. A 'screening assay' means a process used to characterize or select compounds based upon their activity from a collection of compounds.

The term 'preventing' or 'prevention' refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

The term 'prophylaxis' is related to and encompassed in the term 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

The 'subject' or 'patient' afflicted with MuSK-MG treatable with the compounds/agents described herein can be any animal, and is preferably a mammal, such as a wild or domesticated animal or a livestock animal or a human.

'Therapeutically effective amount' means that amount of a drug, compound, antimicrobial, antibody, or pharmaceutical agent that will elicit the biological or medical response of a subject that is being sought by a medical doctor or other clinician. Accordingly, in therapeutic applications described herein, agents and/or compositions thereof are administered to a subject or patient afflicted with MuSK-MG in an amount sufficient to at least partially arrest the symptoms of the disease and its complications. An amount adequate to accomplish this is defined as a 'therapeutically effective amount or dose.' Amounts effective for this use will depend on the severity of the disease and the weight and general state of the patient.

The term 'treating' or 'treatment' of any disease or infection refers, in one embodiment, to ameliorating the disease or infection (i.e., arresting the disease or growth of the infectious agent or bacteria or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or infection, either physically (e.g., stabilization of a discernible symptom), physiologically, (e.g., stabilization of a physical parameter), or both. In a further embodiment, 'treating' or 'treatment' relates to slowing the progression of a disease or reducing an infection.

The term 'MuSK MG' refers to an autoimmune disease, caused by auto-antibodies to proteins in the postsynaptic membrane at neuromuscular synapses, which causes muscle weakness and fatigue that is exacerbated by activity. In MuSK MG, the auto-antibodies are directed to MuSK. Clinical signs and symptoms as seen in patients with serum antibodies against MuSK include, but are not restricted to, muscle weakness or atrophy of the external eye muscles, eyelid muscles, bulbar and neck muscles, as well as muscles involved in respiratory function.

The phrase 'pharmaceutically acceptable' refers to molecular entities and compositions that are physiologically tolerable and do not typically produce an allergic or similar untoward reaction, such as gastric upset, dizziness and the like, when administered to a human.

The term 'inhibit' or 'inhibiting' refers to a statistically significant and measurable reduction in activity, preferably a reduction of at least about 10% versus control, more particularly a reduction of about 50% or more, still more particularly a reduction of about 80% or more. With respect to inhibiting binding of pathogenic IgG4 antibodies to the MuSK IgG-like domain, binding may be reduced by at least about 10%, at least about 20%, at least about 30%, at least about 40%, at least about 50%, at least about 60%, at least about 70%, at least about 80%, at least about 90%, at least about 95%, or about 100%.

B. DETAILED DISCLOSURE

As described herein, the present inventors sought to determine if pathogenic IgG4 auto-antibodies to MuSK interfere directly with MuSK function. To this end, the present inventors performed experiments to address this possibility. Results presented herein reveal that human IgG4 MuSK antibodies bind to the first Ig-like domain in MuSK and prevent Lrp4 from binding MuSK, thereby inhibiting Agrin-stimulated MuSK phosphorylation. Results presented herein also show that inhibiting the association between Lrp4 and MuSK appears to be the major mechanism by which the MuSK IgG4 antibodies disrupt MuSK signaling and cause MuSK MG, since these antibodies do not modulate MuSK surface expression and have only a minor direct effect on MuSK dimerization. See also Huijbers et al. (2013, Proc Natl Acad Sci 110:20783-20788), the entire content of which is incorporated herein by reference.

Myasthenia Gravis

Myasthenia gravis is an auto-immune disease caused by auto-antibodies to synaptic proteins, including acetylcholine receptors (AChRs), MuSK, and Lrp4, leading to muscle weakness. The prevalence in the US is 1/~7,500 (~60,000 patients in US with myasthenia gravis; ~20% of these have MuSK MG). Auto-antibodies to AChRs stimulate accelerated degradation of AChRs and cause complement-mediated structural disorganization of the synapse. In contrast, auto-antibodies to MuSK are IgG4, which are functionally monovalent and fail to engage complement, suggesting that they directly interfere with MuSK function, rather than through the recruitment of complement.

Methods for Making MuSK Extracellular Domains

Recombinant proteins comprising the complete extracellular region of MuSK and domains thereof may be generated as described herein below. Such methods are equally well applied to making recombinant proteins comprising variants and truncations of MuSK domains, including variants and truncations of MuSK Ig1.

Preparation of MuSK-Encoding Nucleic Acid Molecules and MuSK

Nucleic Acid Molecules:

Nucleic acid molecules encoding MuSK or a domain thereof (including, for example, mutated domains) may be prepared by two general methods: (1) Synthesis from appropriate nucleotide triphosphates; or (2) Isolation from biological sources. Both methods utilize protocols well known in the art.

The availability of nucleotide sequence information, such as a full length DNA of SEQ ID NO: 1 (See FIG. 5), enables preparation of an isolated nucleic acid molecule of the invention by oligonucleotide synthesis. Synthetic oligonucleotides may be prepared by the phosphoramidite method employed in the Applied Biosystems 380A DNA Synthesizer or similar devices. The resultant product may be purified according to methods known in the art, such as high performance liquid chromatography (HPLC). Double-stranded polynucleotides, such as a DNA molecule described herein, may be synthesized in stages, due to the size limitations inherent in oligonucleotide synthetic methods. Synthetic DNA molecules constructed by such means may then be cloned and amplified in an appropriate vector. Nucleic acid sequences encoding MuSK or a domain thereof may be isolated from appropriate biological sources using methods known in the art. In that nucleic and amino acid sequences corresponding to MuSK are known in the art and are, for example, presented in U.S. Pat. Nos. 5,814,478; 6,413,740; and 6,852,838 (the entire contents of each of which is incorporated herein in its entirety), genomic and cDNA MuSK clones are readily available in the scientific community and easily made.

Nucleic acids described herein may be maintained as DNA in any convenient cloning vector. In a preferred embodiment, clones are maintained in a plasmid cloning/expression vector, such as pBluescript (Stratagene, La Jolla, Calif.), which is propagated in a suitable *E. coli* host cell.

MuSK-encoding and MuSK domain-encoding nucleic acid molecules include DNA, genomic DNA, RNA, and fragments thereof which may be single- or double-stranded. Also provided are oligonucleotides (sense or antisense strands of DNA or RNA) having sequences capable of hybridizing with at least one sequence of a nucleic acid molecule described herein, such as selected segments of a DNA of SEQ ID NO: 1. Such oligonucleotides are useful as probes for detecting or isolating genes related to MuSK and in polymerase chain reaction (PCR) amplifications.

Methods for obtaining a nucleic acid of interest are also presented herein, wherein such methods include hybridization of a probe having part or all of the sequence shown in SEQ ID NO: 1, or a complementary sequence thereto, to target nucleic acid. Successful hybridization leads to isolation of nucleic acid which has hybridized to the probe, which may involve one or more steps of PCR amplification.

In particular embodiments, oligonucleotides are fragments of the sequences shown in SEQ ID NO: 1 and are at least about 10 nucleotides in length, more particularly at least 15 nucleotides in length, more particularly at least about 20 nucleotides in length. Fragments and other oligonucleotides may be used as primers or probes as discussed but may also be generated, e.g., by PCR.

Polypeptides:

A full-length MuSK or a domain thereof may be prepared in a variety of ways, according to known methods. The protein may be purified from appropriate sources. This is not, however, a preferred method due to the low amount of protein likely to be present in a given cell type at any time. The availability of nucleic acid molecules encoding MuSK or a domain thereof enables production of these proteins using in vitro expression methods known in the art. For example, a DNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis. or BRL, Rockville, Md.

Alternatively, according to a preferred embodiment, larger quantities of MuSK or a domain thereof may be produced by expression in a suitable prokaryotic or eukaryotic system. For example, part or all of a DNA molecule, such as the sequence of SEQ ID NO: 1, may be inserted into a plasmid vector adapted for expression in a bacterial cell, such as *E. coli*. Such vectors comprise regulatory elements necessary for expression of the DNA in a host cell (e.g. *E. coli*) positioned in such a manner as to permit expression of the DNA in the host cell. Such regulatory elements required for expression include promoter sequences, transcription initiation sequences and, optionally, enhancer sequences.

MuSK or a domain thereof produced by gene expression in a recombinant prokaryotic or eukaryotic system may be purified according to methods known in the art. In a particular embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope or the hemagglutinin epitope. Such methods are commonly used by skilled practitioners.

MuSK and fragments thereof, such as MuSK domains (e.g., the first Ig-like domain and mutants thereof) prepared by the aforementioned methods, may be analyzed according to standard procedures. For example, such proteins may be subjected to amino acid sequence analysis, according to known methods.

Polypeptides which are amino acid sequence variants, alleles, derivatives or mutants are also envisioned herein. A polypeptide which is a variant, allele, derivative, or mutant may have an amino acid sequence that differs from that given in SEQ ID NO: 2 or a fragment thereof by one or more of addition, substitution, deletion and insertion of one or more amino acids. Preferred such polypeptides are recognized by pathogenic IgG4 antibodies that are specific for the MuSK Ig-like domain and thus, are able to act as decoys or competitive inhibitors that reduce binding of the IgG4 antibodies to endogenous MuSK expressed on the cell surface. In a particular embodiment, polypeptide is the first MuSK Ig-like domain or a mutant thereof that can bind to the IgG4 antibodies but does not bind to Lrp4.

A polypeptide which is an amino acid sequence variant, allele, derivative or mutant of the amino acid sequence shown in SEQ ID NO: 2 or a fragment thereof may comprise an amino acid sequence which shares greater than about 35% sequence identity with the sequence shown, greater than about 40%, greater than about 50%, greater than about 60%, greater than about 70%, greater than about 80%, greater than about 90% or greater than about 95%. Particular amino acid sequence variants may differ from that shown in SEQ ID NO: 2 or a fragment thereof by insertion, addition, substitution or deletion of 1 amino acid, 2, 3, 4, 5-10, 10-20, 20-30, 30-40, or 40-50 amino acids. For amino acid "homology", this may be understood to be identity or similarity (according to the established principles of amino acid similarity, e.g., as determined using the algorithm GAP (Genetics Computer Group, Madison, Wis.). GAP uses the Needleman and Wunsch algorithm to align two complete sequences that maximizes the number of matches and minimizes the number of gaps. Generally, the default parameters are used, with a gap creation penalty=12 and gap extension penalty=4. Use of GAP may be preferred but other algorithms may be used including without limitation, BLAST (Altschul et al. (1990 J. Mol. Biol. 215:405-410); FASTA (Pearson and Lipman (1998) PNAS USA 85:2444-2448) or the Smith Waterman algorithm (Smith and Waterman (1981) J. Mol. Biol. 147: 195-197) generally employing default parameters. Use of either of the terms "homology" and "homologous" herein does not imply any necessary evolutionary relationship between the compared sequences. The terms are used similarly to the phrase "homologous recombination", i.e., the terms merely require that the two nucleotide sequences are sufficiently similar to recombine under appropriate conditions.

Further to the above, constructs in the form of plasmids, vectors, transcription or expression cassettes which comprise at least one polynucleotide as described herein are envisioned. Also encompassed herein are recombinant host cells which comprise one or more these constructs. A nucleic acid encoding any of the MuSK domains, including variants and truncations thereof, as described herein forms a further aspect, as does a method of production of the MuSK domain or variant or truncation thereof, which method comprises expression from encoding nucleic acid therefor. Expression may conveniently be achieved by culturing recombinant host cells comprising the nucleic acid under appropriate conditions. Following production by expression, a MuSK domain or variant or truncation thereof may be isolated and/or purified using any suitable technique, and then used as described herein.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is E. coli. The expression of antibodies and antibody fragments, for example, in prokaryotic cells such as E. coli is well established in the art.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. eds., John Wiley & Sons, 1992. The disclosures of Sambrook et al. and Ausubel et al. are incorporated herein by reference.

Thus, in a further aspect, a host cell containing nucleic acid as disclosed herein is envisioned. In a still further aspect, a method comprising introducing such nucleic acid into a host cell is envisioned. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene. Also encompassed herein is a method which comprises using a construct as stated above in an expression system in order to express a MuSK domain or variant or truncation thereof as described herein.

Another feature encompassed herein is the expression of DNA sequences contemplated herein, particularly those encoding a MuSK domain or variant or truncation thereof. As is well known in the art, DNA sequences may be expressed by operatively linking them to an expression control sequence in an appropriate expression vector and employing that expression vector to transform an appropriate unicellular host. A wide variety of host/expression vector combinations may be employed in expressing the DNA sequences of this invention. Useful expression vectors, for example, may consist of segments of chromosomal, non-chromosomal, cDNA, and synthetic DNA sequences. Suitable vectors include derivatives of SV40 and known bacterial plasmids, e.g., E. coli plasmids col El, pCR1, pBR322, pMB9 and their derivatives, plasmids such as RP4; phage DNAs, e.g., the numerous derivatives of phage λ, e.g., NM989, and other phage DNA, e.g., M13 and filamentous single stranded phage DNA; yeast plasmids such as the 2 u plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences described herein. These hosts may include well known eukaryotic and prokaryotic hosts, such as strains of E. coli, Pseudomonas, Bacillus, Streptomyces, fungi such as yeasts, and animal cells, such as CHO, YB/20, NSO, SP2/0, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express DNA sequences described herein. Neither will all hosts function equally well with the same expression system. However, one skilled in the art will be able to select the proper vectors, expression control sequences, and hosts without undue experimentation to accomplish the desired expression without departing from the scope of this invention. In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products. Considering these and other factors a person skilled in the art will be able to construct a variety of vector/expression control sequence/host combinations that will express DNA sequences described herein on fermentation or in large scale animal culture.

Polypeptides thus generated may be used, for example, for therapeutic purposes and/or in screening assays for molecules which reduce the binding of pathogenic IgG4 antibodies to endogenous MuSK expressed on the cell surface. Such molecules may be useful for therapeutic and/or research purposes.

In a particular embodiment, recombinant proteins comprising the complete extracellular region of MuSK or domains thereof may be generated as described herein below.

As described herein below, five recombinant proteins were created to either cover the complete extracellular domain of MuSK or domains of MuSK. See also FIGS. 6 and 7. Five proteins of approximately 100 amino acids in length were also generated to further delineate the epitope. In order to generate the specific production constructs, each insert was picked up with a primer set and ligated into the TOPO-II blunt vector (Invitrogen, Breda, The Netherlands). The primers introduced restriction sites that allowed for direct cloning into the pET28 a/b vector (EMD Biosciences, Novagen Brand, Madison, Wis.). All constructs were sequenced to verify their structure (LGTC, Leiden, Netherlands). Protein expression and purification were performed as described previously (Titulaer et al. 2009, J Clin Oncol 27:4260-4267; the entire content of which is incorporated herein by reference).

Additional methods for making MuSK and domains thereof, as well as mutants thereof, are provided in U.S. Pat. No. 5,814,478, the entire content of which is incorporated herein by reference.

Animal Models of MuSK Myasthenia Gravis

MuSK-MG differs from AChR MG with respect to clinical manifestation and symptoms. MuSK-MG presents with more focal muscle involvement (neck, shoulders, facial, and bulbar muscles) and wasting of the involved muscles, particularly axial muscles therein. MuSK, moreover, responds poorly to anticholinesterase treatment, a standard treatment for AChR MG, and is not associated with thymic hyperplasia. Animal models of MuSK-MG are known and have been induced in mice, rats, and rabbits by immunization with purified xenogeneic MuSK ectodomain and by passive transfer of purified serum IgG antibodies isolated from MuSK-MG patients into mice. See, for example, Richman et al. (2012, Ann NY Acad Sci 1274:140-147), Cole et al. (J Physiol. 2010, 588:3217-3229), Cole et al. (Ann Neurol. 2008; 63:782-789), Jha et al. (J Neuroimmunol. 2006; 175:107-117), Mori et al. (J Neuroimmunol. 2012; 245:75-78), Mori et al. (Am J Pathol. 2012; 180:798-810), Mori et al. (J Neuroimmunol. 2012; 244:1-7), Shigemoto et al. (J Clin Invest. 2006; 116:1016-1024), Viegas et al. (Exp Neurol. 2012; 234:506-512), Punga et al. (Exp Neurol. 2011; 230:207-217), Richman et al. (Arch Neurol. 2012; 69:453-460), and Klooster et al. (Brain. 2012; 135:1081-1101), the entire content of each of which is incorporated herein by reference.

Experiments in animal models of multiple sclerosis have been used evaluate tolerance strategies in rats. Results derived therefrom may be applied in the present approach with regard to MuSK-MG. In rats two or three intravenous (iv) injections of 500 ug reduced severity of the disease. See, for example, Experimental and Molecular Pathology 68, 29-37 (2000); Proc Natl Acad Sci 2007; 104(3):920-925). Some indications for disease exacerbation were, however, found in other experiments (Proc Natl Acad Sci 2007; 104(47): 18625-18630). Coupling antigen to nanoparticles may, however, offer a new and more efficient way of inducing tolerance (Hunter et al. ACS Nano. 2014 Mar. 25; 8(3):2148-60. doi: 10.1021/nn405033r. Epub 2014 Feb. 27). Microparticles are also described in the context of inducing T cell tolerance in an animal model of experimental autoimmune encephalomyelitis (Getts et al. Nat Biotechnol 2012; 30:1217-1224.

Passive Transfer Animal Models

Figure 8:
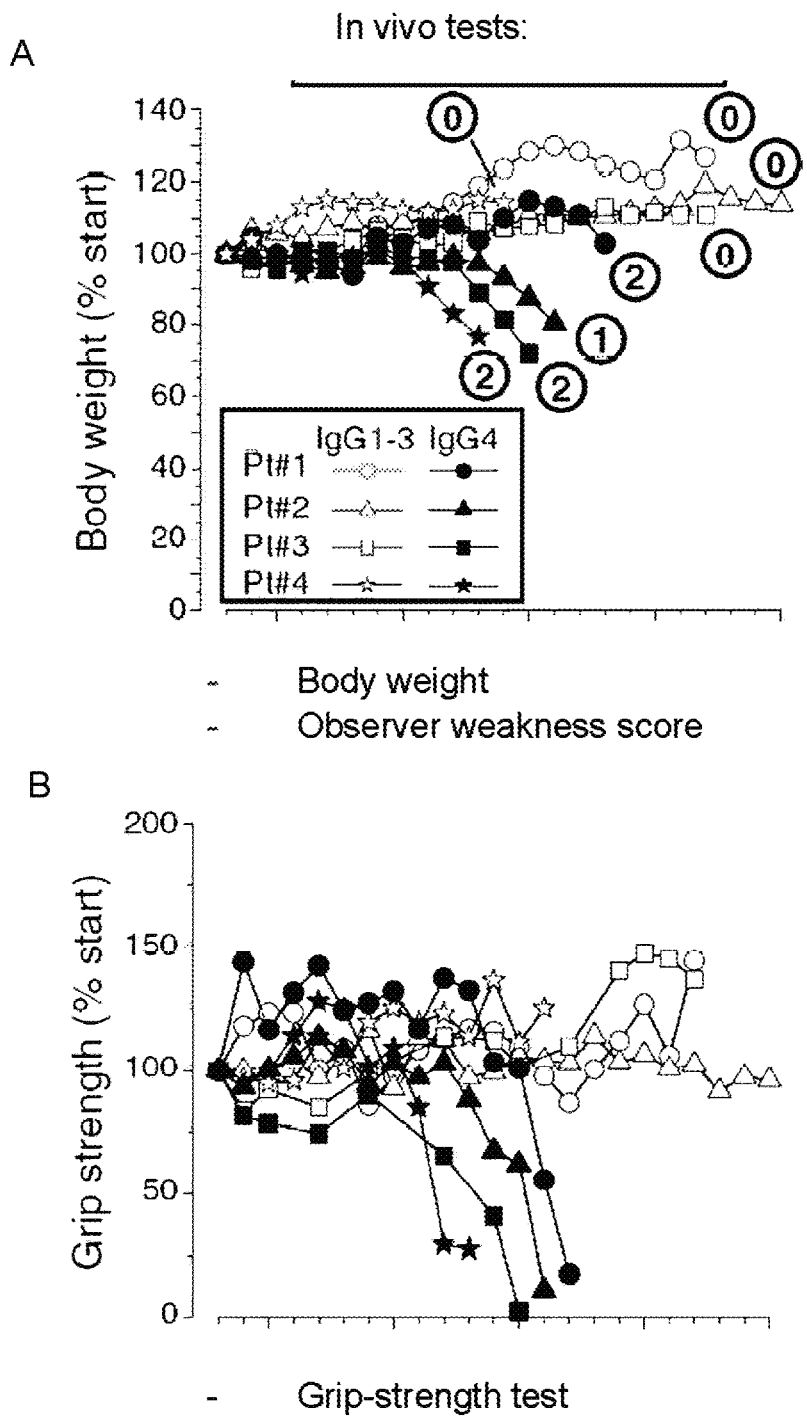
FIG. 8. Analysis of the MuSK MG mouse model described by Klooster et al. (Brain. 2012; 135:1081-1101). Nod-Scid mice. injected with MuSK MG IgG4, lose weight, strength and respiratory depth (A, B, C, D), beginning 7 days after the first injection. Anesthetized mice show decremental compound muscle action potentials (CMAPs) and reduced EPPs (E, F), like MuSK MG patients. AChR density is reduced and the postsynaptic membrane is disorganized (G), as described for MuSK MG.
Figure 8:
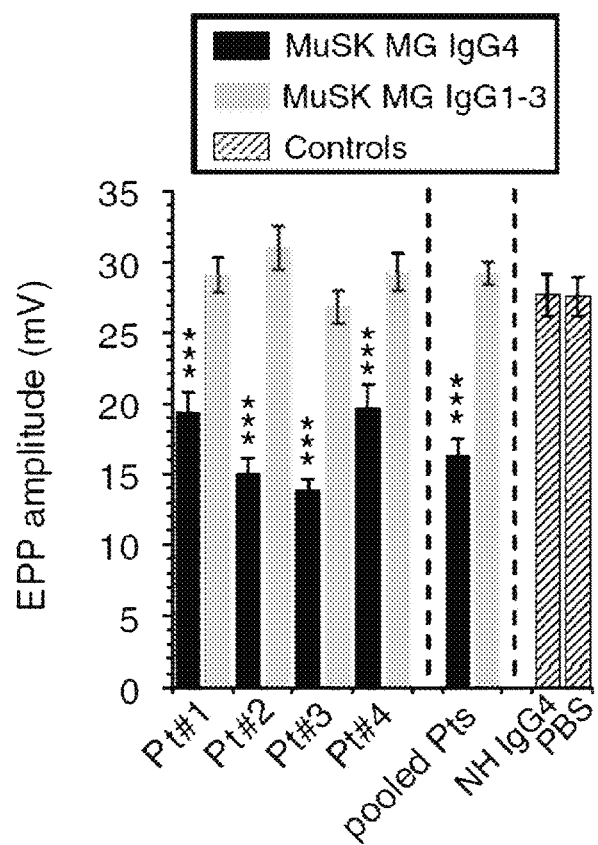

Klooster et al. (Brain. 2012; 135:1081-1101) disclose an exemplary animal model system for MuSK-MG. More particularly, passive transfer studies in NOD.CB17-Prkdcscid/J immunodeficient mice have shown that IgG4 antibodies from MuSK MG patients cause disease without requiring complement or other immune components, demonstrating that these MuSK antibodies cause disease by directly interfering with MuSK function (Klooster et al. supra). Importantly, disease in this passive transfer model provides an excellent representation of the human disease, as the present inventors showed that motor performance, synaptic transmission and synaptic structure are altered (FIG. 8) in ways that reproduce the clinical and cellular aberrations found in MuSK MG. See, for example, FIG. 8 and Klooster et al. (Brain. 2012; 135:1081-1101), the entire content of which is incorporated herein by reference. Accordingly, this IgG4 antibody-mediated passive transfer model is viewed as highly representative of MuSK-MG in humans. In contrast, active immunization models also lead to generation of antibodies which recruit complement and dimerize and modulate MuSK cell surface expression.

Further to the above, the ability of MuSK Ig1 to modulate MuSK MG in this animal model system will be assessed by injecting IgG4 MuSK MG patient antibodies into NOD.CB17-Prkdcscid/J immunodeficient mice to induce MuSK MG, as described previously (Klooster et al. Brain. 2012; 135:1081-1101). As described therein, mice are injected intraperitoneally with purified subclass IgG dissolved in sterile phosphate buffered saline (PBS) at a dose ranging from 0.25 to 4 mg IgG4/day. A baseline for strength in general may, moreover, be established by generating an observer weakness score in advance of the injection of IgG4 MuSK MG patient antibodies. Mice typically begin to show signs of disease after 7-10 days and exhibit overt muscle weakness thereafter. Body weight, respiration depth (as assessed by, for example, whole-body plethysmography) and muscle strength (as assessed by, for example, inverted mesh test and/or grip-strength test) will be measured daily. The dose of patient IgG4 will be adjusted so that the disease progresses gradually over this time course. A collection of MuSK sera from ~50 MuSK MG patients, as well as plasma exchange fluids from 10 patients, will be used for this purpose.

MuSK Ig1 domain or a variant thereof as described herein will be co-injected with IgG4 antibodies from MuSK MG patients into mice to determine whether the MuSK Ig1 domain or a variant thereof can prevent, delay or ameliorate the signs of disease, as assessed by measuring respiration, muscle strength, and body-weight during the treatment and morphological and electrophysiological assays at the end of the experiment. All of these assays may be performed using techniques described in Klooster et al. (Brain. 2012; 135: 1081-1101) and understood by those skilled in the art. These studies will also include control groups, which receive either saline or a ragweed pollen antibody instead of the MuSK Ig1 domain or a variant thereof. In addition, mice will be treated with the MuSK Ig1 domain or a variant thereof alone to assess possible toxicity/side effects.

Each treatment group will consist of 6 mice, which will enable detection of a 50% increase in the mean endplate potential amplitude (from ~15 to ~22 mV) due to the MuSK Ig1 domain or a variant thereof treatment with a calculated power of 0.8. The dose and frequency of injections of MuSK Ig1 domain or a variant thereof will be varied. The protective effect of the MuSK Ig1 domain or a variant thereof will be tested in at least two ways. At the outset, the present inventors will begin dosing of the MuSK Ig1 domain or a variant thereof about one week after the patient IgG4 antibody was first injected in order to learn whether one injection of MuSK Ig1 domain or a variant thereof can halt or reverse disease progression once symptoms of disease become evident. Additional experiments are also envisioned which call for reversing the order of administration, increasing the frequency of injections, and/or initiating administration of the MuSK Ig1 domain or a variant thereof at day 1, 2, 3, 4, 5, or 6 post injection of patient IgG4 antibody. Such approaches may yield information relevant to optimizing dosing schedules. Such approaches would, for example, involve dosing of the MuSK Ig1 domain or a variant thereof one day before the patient IgG4 antibody is first injected in order to learn whether the MuSK Ig1 domain or a variant thereof can prevent disease. Since weakness in MuSK MG patients can fluctuate dramatically and treatment of known MuSK MG patients in remission periods is envisioned herein, such experiments are relevant to use of the MuSK Ig1 domain or a variant thereof to prevent relapse.

As indicated herein above, multiple outcome measurements will be assessed including: (1) muscle strength and muscle fatigue; (2) respiratory function (breathing volume and frequency); (3) histological analysis of muscle, including staining for AChR, MuSK, nerve terminals and electron microscopic, ultrastructural studies; (4) in vitro microelectrode electrophysiological analysis of synaptic transmission, including miniature endplate potential (MEPP) amplitude and frequency, endplate potential and quantal content. All of these methods are performed in accordance with standard protocols in the field and have been described in detail elsewhere. See, for example, FIG. 8 and Klooster et al. (Brain. 2012; 135:1081-1101).

Therapeutic Strategies

Several types of therapeutic strategies are envisioned herein. In a particular embodiment, a MuSK Ig1 domain decoy or variant or truncation thereof (e.g., a mutated or truncated MuSK Ig1 domain that binds pathogenic IgG4 antibodies but does not bind to Lrp4) is administered to a subject afflicted with MuSK-MG, used to treat a subject afflicted with MuSK-MG, and/or used in a medicament to treat MuSK-MG or a device for use in the treatment of MuSK-MG. Such strategies generally relate to treating a subject afflicted with MuSK-MG and may more particularly relate to, for example, improving motor function, preserving neuromuscular synapses, and/or providing symptomatic relief in a subject afflicted with MuSK-MG.

With regard to the aforementioned device, the present inventors envision plasmapheresis using a MuSK-sepharose column to absorb the pathogenic IgG4 antibodies. In a particular embodiment thereof, the first Ig-like domain of MuSK is attached to the sepharose column. In another embodiment, a mutated version of the first Ig-like domain of MuSK is attached to the sepharose column. Such mutations include, without limitation, any one of or a combination of a mutation of I96, T36 and/or A114. With regard to mutations of I96, in one embodiment, the mutation of isoleucine at amino acid position 96 results in a substitution of any amino acid at amino acid position 96 of MuSK, except for leucine or valine (hydrophobics of approximately the same size as isoleucine). In a more particular embodiment thereof, the mutation results in a substitution of Alanine for Isoleucine at I96, which substitution abrogates Lrp4 and MuSK binding. With regard to mutation in T36, in one embodiment, the mutation is T36N or T36A. With regard to mutation in A114, in one embodiment, the mutation is A114K.

Plasmapharesis refers to the removal, treatment, and return of blood plasma components derived from the circulating blood of a subject. It is, therefore, a medical procedure performed outside the body and thus, falls under the category of an extracorporeal therapy. It is used for the treatment of a variety of disorders including MG (Batocchi et al., 2000, Therapeutic apheresis: official journal of the International Society for Apheresis and the Japanese Society for Apheresis 4:275-279; Yazdi et al., 2012, Romanian Journal of Internal Medicine 50:245-247; the entire content of each of which is incorporated herein in its entirety), Goodpasture's syndrome, Guillain-Barré syndrome, lupus, and thrombotic thrombocytopenic purpura.

During plasmapheresis, blood is removed from a subject via needle or previously implanted catheter. Plasma is thereafter removed from the blood using a cell separator. Three procedures are commonly used to achieve separation of plasma from blood cells. Discontinuous flow centrifugation requires one venous line and typically involves removal of about a 300 ml batch of blood at a time, which is centrifuged to separate the plasma from the blood cells. Continuous flow centrifugation requires two venous lines and thus, involves the removal of smaller volumes of blood at any one time due to the ability to continuously spin out plasma. Plasma filtration requires two venous lines and involves filtration using standard hemodialysis equipment. Since this is a continuous process, it requires removal of less than 100 ml of blood at a time.

After plasma separation, blood cells are returned to the subject undergoing treatment, while the plasma, which contains antibodies (including pathogenic antibodies) is first treated and then returned to the subject under treatment via traditional plasmapheresis. As indicated herein above, the present inventors envision that treatment of the plasma from MuSK-MG patients will include contacting the plasma with MuSK Ig1 domain (e.g., immobilized MuSK Ig1 domain), so as to incorporate a specific absorption step whereby immunoglobulin molecules, particularly pathogenic IgG4 antibodies specific for the MuSK Ig1 domain, are absorbed and thus depleted from the plasma prior to return to the subject afflicted with MuSK-MG. In a particular embodiment thereof, the immobilized MuSK Ig1 domain comprises a mutation of I96, T36 and/or A114. In another particular embodiment, the MuSK Ig1 domain or a mutant thereof is immobilized on a sepharose column using techniques known to those skilled in the art. See, for example, Supplemental Methods below for additional guidance pertaining to immobilization of MuSK domains.

More particularly, the aforementioned MuSK polypeptides can be used to remove pathogenic MuSK antibodies specifically by ways of immunoabsorption. To that end a MuSK polypeptide (e.g., the Ig1 domain) could be immobilized on a stable column material/carrier (e.g., Sepharose beads). A MuSK-MG patient would then be connected to this system during plasmapheresis. By way of background, since plasmapheresis is a treatment quite often used for treating MuSK-MG patients, incorporation an absorption step during the course of plasmapheresis could be achieved with ease. The plasma would be run past this column, thereby absorbing the MuSK specific antibodies from the plasma and the MuSK antibody-depleted plasma generated thereby returned to the patient. This approach focuses on extracorporal removal of pathogenic antibodies. This strategy has been explored for AChR MG using protein-A, tryptophan or a peptide representing part of the AChR. See, for example, Yang et al. (Artif Cells Blood Substit Immobil Biotechnol. 2004; 32(4):519-28); Benny et al. (Transfusion. 1999 July; 39(7):682-7); Takamori et al. (Therapeutic Apheresis 2001, 5(5):340-350); Takamori et al. (Transfus Sci 1996, 17(3):445-453); Lagoumintzis et al. (J Neuroimmunol. 2014 Feb. 15; 267(1-2):1-6. doi: 10.1016/j.jneuroim.2013.11.001. Epub 2013 Nov. 10); the entire content of which is incorporated herein by reference.

Also envisioned herein are methods, uses, and medicaments for inducing oral or nasal tolerance to the first Ig-like domain of MuSK. The MuSK Ig1 domain and mutants thereof, as described herein, are set forth as antigens suitable for inducing oral or nasal tolerance to the MuSK Ig1 domain and thus, offer yet another therapeutic option for subjects afflicted with MuSK-MG. Oral tolerance is classically defined as the suppression of immune responses to antigens (Ag) that have been administered previously by the oral route. See, for example, Faria et al. (2006, Clinical & Developmental Immunology 13:143-157), the entire content of which is incorporated herein by reference. As described therein, oral and nasal tolerance have been shown to suppress several animal models of autoimmune diseases, including experimental allergic encephalomyelitis (EAE), uveitis, thyroiditis, myasthenia, arthritis and diabetes in the nonobese diabetic (NOD) mouse, and non-autoimmune diseases such as asthma, atherosclerosis, colitis and stroke. Oral tolerance has, moreover, been tested in human autoimmune diseases including multiple sclerosis, arthritis, uveitis and diabetes and in allergy. Mucosal tolerance provides an attractive approach for treatment of autoimmune and inflammatory diseases due to minimal toxicity, ease of administration over time, and Ag-specific mechanism of action. See also Weiner et al. (2011, Immunol Rev 241:241-259), the entire content of which is incorporated herein by reference).

Further to the above, Maiti et al. (2004, J Neuroimmunology 152:112-120; and (29); the entire content of each of which is incorporated herein by reference), for example, have demonstrated that a syngeneic recombinant fragment of the extracellular domain of the acetylcholine receptor (AChR) α-subunit (Ra1-205), when administered orally, suppresses ongoing experimental autoimmune myasthenia gravis (EAMG) in rats. They have determined that the underlying mechanism involves a shift from Th1 to Th2 regulation as evidenced by downregulated mRNA expression levels of IFN-γ and TNF-α, upregulated IL-10, changes in anti-AChR IgG isotypes, and diminished Th1 signaling via CD28/CTLA-4:B7. The finding that mucosal tolerance can be induced by the aforementioned syngeneic fragment even during an active disease phase is significant in that it underscores the genuine potential for treatment of MG in human patients that seek medical help when the disease already exists.

The present inventors envision that methods similar to those described in Maiti et al. (supra), Faria et al. (supra), and Weiner et al. (supra) may be applied in circumstances wherein the MuSK Ig1 domain and mutants thereof, as described herein, are used as antigens for inducing oral or nasal tolerance.

For the induction of oral tolerance, high and low dose tolerance should be considered. The type of tolerance induced relates to the dose of antigen fed: anergy/deletion (high dose) or regulatory T-cell (Treg) induction (low dose). (Weiner et al. Immunol Rev. 2011 May; 241(1):241-59). In typical high dose experiments, ovalbumin (20 mg/ml) was added to the drinking water of rats for 5 days (Proc Natl Acad Sci USA. 2009 Sep. 29; 106(39):16770-5). An amount of 0.5 mg per day was considered low dose (Liu et al. J Immunol. 1999 Aug. 15; 163(4):2284-90). The induction of human oral tolerance has been described (Kraus et al. Gastroenterology 2004. 126: 1771-1778; Husby et al. J. Immunol. 1994. 152: 4663-4670; Mestecky et al. J. Immunol. 2007. 179: 5633-5638) after feeding keyhole limpet hemocyanin (KLH), a neoantigen which is safe to use in humans. Compared with rodent studies, the antigen doses used were much lower and effects observed were not as uniform: reduced delayed-type hypersensitivity (DTH) (Husby et al. J. Immunol. 1994. 152: 4663-4670; Mestecky et al. J. Immunol. 2007. 179: 5633-5638) and antigen-specific proliferation of PBMC (Kraus et al. Gastroenterology 2004. 126: 1771-1778; Husby et al. J. Immunol. 1994. 152: 4663-4670; Mestecky et al. J. Immunol. 2007. 179: 5633-5638) have been reported after feeding KLH, although KLH-specific B-cell responses were unaffected (Kraus et al. Gastroenterology 2004. 126: 1771-1778) or even amplified (Husby et al. J. Immunol. 1994. 152: 4663-4670; Mestecky et al. J. Immunol. 2007. 179: 5633-5638). See also Kapp et al. Eur. J. Immunol. 2010. 40: 3128-3137 for review. High dose of KLH was 50 mg, and repeated low dose consisted of 10 days of 5 mg a day ingested in acid-resistant capsules (Kapp et al. Eur. J. Immunol. 2010. 40: 3128-3137).

Clinical endpoints for assessing efficacy of the aforementioned methods, uses, medicaments, and devices include, without limitation, changes in muscle strength, fatigue, measures of Activities of Daily Life, or myasthenia gravis specific scores, like MGFA score, Quantitative Myasthenia Gravis score (QMG). Other endpoints include changes in MuSK antibody titer, or changes in electrophysiological measurements, like electromyogram using repetitive stimulation, single fiber electromyography.

In one particular embodiment, with respect to the compounds or agents described herein, the compound/agent is administered alone or in conjunction with other compounds/agents described herein or known to be efficacious in the treatment of a disorder associated with synaptic loss and motor dysfunction such as those described herein. In another aspect, pharmaceutical compositions comprising a compound/agent or a plurality of the compounds/agents described herein are administered to a subject in need thereof. Compounds and agents described herein may also be used in the preparation of a medicament for treating MuSK MG.

In one embodiment, with respect to the method of treatment, use of an agent of compound, or preparation of a medicament, the disease or condition is MuSK MG.

Pharmaceutical Compositions

When employed as pharmaceuticals, the compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base.

Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds described herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds described herein can also be administered in sustained release forms or from sustained release drug delivery systems. A description of representative sustained release materials can be found in *Remington's Pharmaceutical Sciences.*

The following formulation examples illustrate representative pharmaceutical compositions of this invention. The present invention, however, is not limited to the following pharmaceutical compositions.

Formulation 1

Tablets

A compound of the invention is admixed as a dry powder with a dry gelatin binder in an approximate 1:2 weight ratio. A minor amount of magnesium stearate is added as a lubricant. The mixture is formed into 240-270 mg tablets (80-90 mg of active amide compound per tablet) in a tablet press.

Formulation 2

Capsules

A compound of the invention is admixed as a dry powder with a starch diluent in an approximate 1:1 weight ratio. The mixture is filled into 250 mg capsules (125 mg of active amide compound per capsule).

Formulation 3

Liquid

A compound of the invention (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4

Tablets

A compound of the invention is admixed as a dry powder with a dry gelatin binder in an approximate 1:2 weight ratio. A minor amount of magnesium stearate is added as a lubricant. The mixture is formed into 450-900 mg tablets (150-300 mg of active amide compound) in a tablet press.

Formulation 5

Injection

A compound of the invention is dissolved or suspended in a buffered sterile saline injectable aqueous medium to a concentration of approximately 5 mg/ml.

Formulation 6

Topical

Stearyl alcohol (250 g) and a white petrolatum (250 g) are melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present compounds/agents are used as therapeutic agents for the treatment of MuSK-MG in mammals. Accordingly, the compounds and pharmaceutical compositions described herein find use as therapeutics for preventing and/or treating MuSK-MG in mammals, including humans.

In a method of treatment aspect, a method for treating a mammal susceptible to or afflicted with MuSK-MG is presented herein, which method comprises administering an effective amount of one or more of the pharmaceutical compositions just described. In a more particular embodiment, the method comprises administering an effective condition-treating or condition-preventing amount of one or more of the pharmaceutical compositions described herein.

In a further aspect, the present compounds are provided for use as pharmaceuticals, especially in the treatment or prevention of MuSK-MG. Also provided herein is the use of the present compounds in the manufacture of a medicament for the treatment or prevention of MuSK-MG. Also encompassed is at least one compound or agent described herein for use in treating or preventing MuSK-MG. Further to the above, a combination of one or more of the compounds/agents described herein for a method of treating MuSK-MG in a subject is also encompassed herein.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as, e.g., MuSK-MG, the regimen for treatment usually stretches over many months or years, so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound of the invention, with preferred doses each providing from about 0.1 to about 10 mg/kg and especially about 1 to about 5 mg/kg. Long term treatment of the above-mentioned diseases is envisioned to span ~5 years with respect to ALS, ~20 years with respect to sarcopenia, and >30 years with respect to anti-MuSK myasthenia gravis.

Transdermal doses are generally selected to provide similar or lower blood levels than are achieved using injection doses. Modes of administration suitable for mucosal sites are also envisioned herein and include without limitation: intra-anal swabs, enemas, intranasal sprays, and aerosolized or vaporized compounds and/or compositions for delivery to the lung mucosa. One of skill in the art would choose an appropriate delivery mode/s based on a variety of parameters, including the organ or tissue site in a patient with a disease or condition that is most severely affected by the disease or condition. A skilled practitioner could, for example, treat a patient afflicted with MuSK-MG, for example, with a therapeutic regimen that included delivery of the compounds or compositions of the invention using an intramuscular injection for direct delivery to an affected muscle. Intraperitoneal (ip) and intravenous (iv) injection delivery modes are also envisioned for the treatment of MuSK-MG.

When used to prevent the onset of MuSK-MG, the compounds described herein will be administered to a patient at risk for developing the condition or disorder, typically on the advice and under the supervision of a physician, at the dosage levels described above. Patients at risk for developing a particular condition generally include those with a family history of the condition, or those who have been identified by genetic testing or screening to be particularly susceptible to developing the condition.

The compounds of this invention can be administered as the sole active agent or they can be administered in combination with other agents, including other compounds that demonstrate the same or a similar therapeutic activity and are determined to be safe and efficacious for such combined administration.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

Example I

Experimental Procedures

Patients

Twenty-five Dutch MuSK MG patients and 18 controls were included for the studies described herein (Table 1). All patients gave written consent according to the Declaration of Helsinki, and the study was approved by the Leiden University Medical Center ethics committee. The patients were diagnosed based on the presence of fatigable muscle weakness with electrophysiological evidence of decrementing compound muscle action potentials in response to low-rate repetitive nerve stimulation or increased jitter on single-fiber electromyography. Furthermore, they tested positive for MuSK antibodies in a standard commercial radioimmunoprecipitation assay (RIA) from RSR (RSR, Cardiff, UK). Eighteen controls included five patients with AChR MG, one with Lambert-Eaton myasthenia gravis (LEMS) and twelve healthy controls. Plasmapheresis material from 7 patients became available during regular treatment for MuSK MG. This material was stored at −80° C. until it was further processed for IgG purification. Plasmapheresis material was affinity purified for IgG4 and IgG1-3 as described previously (Supplemental Methods) (13).

TABLE 1

Demographical and clinical characteristics of 25 MuSK MG patients.

| | |
|---|---|
| Women - n (%) | 15 (60) |
| Age at onset - median (range) in yrs | 38.5 (2-80) |
| Follow-up - median (range) in yrs | 5.8 (0.5-33) |
| Predominant weakness | |
| Bulbar - n (%) | 9 (36) |
| Oculobulbar - n (%) | 12 (48) |
| Generalized - n (%) | 4 (16) |
| MGFA* at maximum - n | |
| II (b) | 6 (6) |
| III (b) | 4 (2) |
| IV (b) | 8 (8) |
| V (%) | 7 (28) |
| Immunosuppressive treatment at serum sampling - n (%) | 16 (64) |

*Myasthenia Gravis Foundation of America score is a quantitative assessment of muscle weakness Binding Assays Recombinant proteins were generated to cover the complete extracellular region of MuSK or domains of MuSK (See Supplemental Methods). Epitopes recognized by the MuSK MG patient antibodies were identified using an ELISA and by a competition ELISA, using twenty amino-acid overlapping peptide fragments (LUMC peptide facility) that cover the first Ig-like domain (Supplemental Methods). Binding between MuSK and Lrp4 was measured using a solid-phase binding assay, as described previously (21), except human rather than rat MuSK was used (Supplemental Methods).

Tyrosine Phosphorylation Assays

MuSK L746M/S747T was generated by site-directed mutagenesis and transfected into 3T3 cells with Lipofectamine 2000 (Invitrogen). 3T3 cells were treated with 40 µg/ml IgG4 from MuSK MG patients, or controls from 12 to 36 hr after transfection; cell surface proteins were digested by trypsin (0.05%) for 5 minutes at 37° C. Myotubes were stimulated with 0.4 nM neural Agrin or Agrin together with 40 µg/ml IgG4 from MuSK MG patients, or controls for 30 minutes at 37° C. MuSK tyrosine phosphorylation was measured as described previously (53). PJ69-4A yeast were transformed with plasmids encoding the GAL4 DNA binding domain fused to wild-type rat MuSK, MuSK D753A, MuSK L745M, S746T or the insulin receptor. Fusions proteins were immunoprecipitated with antibodies to GAL4 and Western blots were probed with antibodies to phosphotyrosine.

Immunostaining

U2O cells were transfected with human MuSK-GFP or MuSK-ΔIg-1-GFP, and fixed cells were stained with patient antibodies, followed by Alexa 594 conjugated-mouse anti-human IgG (Invitrogen). Stained cells were viewed with a Leica DM 5500B microscope, and images were analyzed with LAS AF software (Supplemental Methods).

Supplemental Methods

IgG Purification

Plasma was diluted five-fold in a citrate buffer and filtered through a 0.22 µm filter. Depending on IgG subtype, protein concentration and column capacity (6 mg/ml for IgG4 and 15 mg/ml for IgG1-3), plasma was loaded onto an IgG4 class-specific affinity column (BAC, Leiden, The Netherlands). Bound IgG4 antibodies were eluted with 0.1 M glycine, pH 3.0, buffered with 1M Tris pH 8.0 and dialyzed against PBS. After depleting plasma of IgG4, the IgG1-3 fraction was purified on an IgG1-3 affinity column, as described above. The quality and quantity of the purified fractions were assessed using a MuSK ELISA and Western blotting, as described previously (Klooster et al. 2012, Brain 135:1081-1101; the entire content of which is incorporated herein by reference).

Recombinant Proteins

Five recombinant proteins were created to either cover the complete extracellular domain of MuSK or domains of MuSK. Five proteins of approximately 100 amino acids in length were also generated to further delineate the epitope. In order to generate the specific production constructs, each insert was picked up with a primer set and ligated into the TOPO-II blunt vector (Invitrogen, Breda, The Netherlands). The primers introduced restriction sites that allowed for direct cloning into the pET28 a/b vector (EMD Biosciences, Novagen Brand, Madison, Wis.). All constructs were sequenced to verify their structure (LGTC, Leiden, Netherlands). Protein expression and purification were performed as described previously (Titulaer et al. 2009, J Clin Oncol 27:4260-4267; the entire content of which is incorporated herein by reference).

MuSK ELISA

The epitope(s) recognized by the MuSK MG patient antibodies were identified by coating MaxiSorp plates (NUNC, Thermo Scientific, Roskilde, Denmark) with 0.3 µg/well of the various recombinant MuSK proteins. The full length extracellular region of MuSK was dissolved in PBS. The other proteins were coated in 1M urea. After overnight incubation at 4° C., the plate was washed, blocked and incubated with patient serum according to the procedure recommended for the commercial MuSK ELISA (IBL international, Hamburg, Germany). All assays were performed in duplicate.

Expression in U2O Cells and Immunostaining

Full length MuSK was cloned from human muscle cDNA with the following primers: forward 5'-gac ctc gag atg aga gag ctc gtc aac att cca ctg-3' (SEQ ID NO: 10) and reverse 3'-ctc tcc cgt ctc cct tga cac tca cag acc atg gcg t-5' (SEQ ID NO: 11). These primers introduced an N-terminal XhoI and a C-terminal KpnI site that allowed subcloning into the pEGFP-N2 vector. Deletion of the stop codon enabled expression of a GFP-fusion protein. To generate the ΔIg-like1 domain MuSK construct the same approach was used except for the inclusion of a different forward primer: 5'-gcc ttc agc gga act gag aaa cct aaa ata act cgc cct ccc-3' (SEQ ID NO: 12) deleting amino-acids 24-120.

U2O cells (ATCC, Manassas, Va., U.S.A) were transiently transfected with 0.5 µg/ml DNA and X-tremeGENE 9 transfection reagent (Roche, Basel, Switzerland). The following day, the cells were fixed with 4% paraformaldehyde (PFA), permeabilized with 0.03% Tween-20 and 0.2% Triton X-100, and non-specific binding sites were blocked with 1% bovine serum albumin (BSA) in PBS for 1 hour. Thereafter, patient serum was diluted 1:50 in blocking buffer and incubated with the cells for one hour at RT. Next the cells were washed with PBS and bound antibodies were labelled with goat anti-human IgG ALEXA594 (Invitrogen). Immunolabelled cells were imaged with a Leica DM 5500B microscope, and analysed with LAS AF software. For each patient's immunostaining at least 10 images were taken at two independent experiments which were analysed by two independent blinded observers.

Peptide Competition Assay

Twenty amino-acids-long overlapping peptide fragments were purchased from the LUMC peptide facility covering the Ig-like1 domain. Serial dilutions of patient IgG4 were made to identify an antibody concentration in which antibody-binding to the extracellular region of MuSK was linear. The purified IgG4 fractions were incubated with the peptides, ranging from an equimolar amount of peptide: purified IgG4 to a 1000-fold excess of peptide. The peptides were incubated with purified IgG4 for 30 minutes at room temperature before measuring binding to the extracellular region of MuSK using the ELISA.

MuSK-Lrp4 Interaction Solid-Phase Binding Assay

Human MuSK-Fc was generated by PCR amplified using a forward primer, 5'-agc gaa ttc atg aga gag ctc gtc aac att c-3' (SEQ ID NO: 13) and a reverse primer, 3'-g agt gga tgt atg agg tac tga tct aga cgt-5' (SEQ ID NO: 14). The primers introduced an N-terminal EcoRI site and a C-terminal BglII site to insert the DNA into pFUSE-hIgG1-FC1 (Invivogen, San Diego, Calif., U.S.A.). The vector was transfected into COS-7 cells, and human MuSK-Fc was harvested and concentrated from media 3 days after transfection. MuSK-Fc (250 ng/well) was added to Protein A 96 wells plates (Thermo Scientific, Rochester, N.Y., U.S.A.) overnight at 4° C., as described (Zhang et al. 2011, J Biol Chem 286:40624-40630; the entire content of which is incorporated herein by reference). The plates were washed and blocked with protease free 1% BSA containing IgG (Gemini bioproducts, Sacramento, Calif., U.S.A.). Next, 10 nM Lrp4-AP, 10 nM agrin and 8.33 µM of purified IgG4 or IgG1-3 from patients or controls were co-incubated for two hours at room temperature. Binding of Lrp4-AP was measured, as described previously (Zhang et al. 2011, J Biol Chem 286:40624-40630). The value of Lrp4-AP binding in the absence of IgG was assigned a value of 100%. These experiments were performed in duplicate.

Generation of MuSK Mutants

To investigate the effect of IgG4 and IgG1-3 antibodies from MuSK MG patients on MuSK dimerization, MuSK L746M/S747T-GFP were generated. The 5'-act ttg gca tga cca gga aca tct act cag ca-3' (SEQ ID NO: 15) and 5'-aga tgt tcc tgg tca tgc caa agt cgg caa ttt tca c-3' (SEQ ID NO: 16) primers were used to introduce the point mutation and combined with forward primer 5'-gac ctc gag atg aga gag ctc gtc aac att cca ctg-3' (SEQ ID NO: 17) and reverse primer 5'-gag agg gca gag gga act gtg agt gtc tgg tac cgc a-3' (SEQ ID NO: 18) to introduce an XhoI and KpnI site which allowed for direct cloning into the pEGFP-N2 vector.

MuSK Immunoprecipitation and Western Blotting

MuSK was immunoprecipitated using antibodies to the carboxy-terminus of MuSK and detected by probing Western blots with antibodies to MuSK (AF3904 from R&D Systems) (Herbst and Burden 2000; Stiegler et al., 2006; Hallock et al., 2011). Tyrosine phosphorylated MuSK was detected by probing western blots with monoclonal antibody 4G10 to phosphotyrosine (Millipore). Quantitation of the western blots was performed by densitometric scanning using NIH Image J 1.04b software. AU values are given as mean±standard error of the mean. A two-tailed t test was used to determine whether differences were statistically significant (p<0.05).

Results

The Main Immunogenic Region (MIR) Includes Structural Epitopes Contained in the First Ig-Like Domain of MuSK.

The earliest available serum samples from 25 MuSK MG patients and sera from 18 controls, were tested for immunoreactivity against human MuSK recombinant proteins using an ELISA (FIG. 1a). All patients, but no controls had high immunoreactivity against the Ig-like domain 1, although the level of binding varied among patients (FIG. 1a). This variation likely reflects differences in antibody titer and/or affinity for MuSK. For 20 patients, the immunoreactivity was limited to the first Ig-like domain (FIG. 1a). Five patients showed additional immunoreactivity against the Ig-like domain 2 (FIG. 1a). Reactivity to the Ig-like domain 3 or the Frizzled-like domain (FIG. 1a) was not detected.

In addition, the present inventors also expressed full length MuSK-GFP or a mutant form of MuSK-GFP lacking the first Ig-like domain (ΔIg-like1 MuSK) in non-muscle cells and stained transfected cells with patient sera. Antibodies that bound selectively to the first Ig-like domain stained cells expressing wild-type MuSK but not the mutant form lacking the first Ig-like domain (FIG. 1b). In contrast, antibodies that showed reactivity to the second Ig-like domain stained cells expressing wild-type MuSK as well as cells expressing MuSK lacking the first Ig-like domain (FIG. 1c). In conclusion, all patients in this Dutch cohort harbor antibodies against the first Ig-like domain in MuSK at disease onset. Therefore, this region is likely to represent the MIR of MuSK. A small group of patients have additional auto-antibodies against the second Ig-like domain.

In AChR MG and other autoimmune diseases, auto-antibodies often require a discontinuous stretch of amino acids that comprise a structural epitope (29,30,31,32,33,34). In order to determine whether the auto-antibodies to MuSK recognize a linear epitope in the first Ig-like domain of MuSK, the present inventors used a competition ELISA with overlapping 20-mer peptides from the first Ig-like domain (FIG. 1d). Pre-incubation of patient antibodies with the complete Ig-like domain 1 inhibited binding of the IgG4 fractions to full-length recombinant MuSK. Inhibition was nearly complete for patients 5 and 17 who harbor antibodies that bind exclusively to the first Ig-like domain, whereas competition was incomplete for patient 23 with reactivity to the second Ig-like domain. These findings, therefore, confirmed results acquired using direct ELISA. Pre-incubation of the patient antibodies with 20-mer peptides, covering the first Ig-like domain, were largely without effect, with the exception of amino acids 64-104, which modestly (~10%) reduced antibody binding to full-length MuSK (FIG. 1 c). These findings indicate that the antibodies bind to a structural epitope, formed either by non-contiguous sequences within the first Ig-like domain or folding of a linear amino acid sequence, which is poorly represented in short peptides. Thus, similar to antibodies in AChR MG, antibodies to MuSK only poorly recognize linear sequences. Nonetheless, because peptides extending from amino acid 64 to 104 react with the patient antibodies, this region is likely to be the core structure of the MuSK MIR.

MuSK Patient IgG4 Antibodies Interfere with Agrin-Dependent Association Between MuSK and Lrp4.

One face of the first Ig-like domain in MuSK is solvent-exposed and binds Lrp4. Because the pathogenic IgG4 antibodies to MuSK bind the first Ig-like domain the present inventors asked whether the auto-antibodies interfered with the association between Lrp4 and MuSK. To this end, binding between Lrp4 and MuSK was measured using a solid phase binding assay in which the extracellular region of MuSK, fused to Fc (ecto-MuSK-Fc) was adsorbed to protein A plates. The extracellular region of Lrp4 (ecto-Lrp4), fused to human alkaline phosphatase (AP), binds specifically but weakly to ecto-MuSK in the absence of neural Agrin; neural Agrin binds Lrp4 and stimulates strong and specific binding of AP-ecto-Lrp4 to ecto-MuSK (21). The present inventors tested IgG4 as well as IgG1-3 antibodies from 7 MuSK MG patients and found that the IgG4 auto-antibodies from all MuSK MG patients strongly inhibited binding between Lrp4 and MuSK, reducing binding by as much as 80-100%, in a dose-dependent manner (FIG. 2a), whereas IgG1-3 patient antibodies had little effect, similar to IgG4 antibodies from healthy controls (FIG. 2b). The patient antibodies that were the most effective inhibitors of MuSK-Lrp4 association were the most potent inducers of myasthenia in vivo in a passive transfer model (13). Because the association between MuSK and Lrp4 is crucial for maintaining the neuromuscular synapse, these findings indicate that the auto-antibodies cause myasthenia, in large part, by interfering with binding between MuSK and Lrp4.

Given these findings, the present inventors wondered whether binding of patient IgG4 antibodies to MuSK required MuSK I96, which is required for MuSK to bind Lrp4. The present inventors used an ELISA, in which patient antibodies were attached to a Protein-A plate, which was probed with alkaline phosphatase (AP)-MuSK fusion proteins, encoding either the entire extracellular region from wild-type MuSK or MuSK I96A. FIG. 2c shows that mutation of MuSK I96 failed to reduce antibody binding, indicating that I96 does not participate in binding between MuSK and patient antibodies. These findings indicate MuSK binds Lrp4 and patient antibodies by distinct mechanisms and that mutation of I96 does not interfere with antibody-binding.

Because binding between Lrp4 and MuSK is essential for Agrin to stimulate MuSK phosphorylation, the present inventors asked whether the pathogenic IgG4 auto-antibodies to MuSK prevented Agrin-induced MuSK phosphorylation in cultured muscle cells. To address this question, IgG4 antibodies from patients with MuSK MG were added to cultured C2 myotubes, together with neural Agrin, and MuSK phosphorylation was measured. Patient IgG4 antibodies to MuSK blocked MuSK phosphorylation (FIGS. 2d,e). Together, these data indicate that the MuSK antibodies cause disease by preventing Lrp4 from binding MuSK and blocking MuSK phosphorylation.

MuSK Patient IgG4 Antibodies have No Direct Inhibitory Effect on MuSK Dimerization.

Because the first Ig-like domain of MuSK also contains a hydrophobic surface that functions as a dimerization interface, which is important for Agrin to induce MuSK phosphorylation (25), the present inventors considered the possibility that pathogenic IgG4 antibodies to MuSK might also directly interfere with MuSK homo-dimerization and inhibit MuSK function by an additional mechanism. They therefore sought to determine whether IgG4 antibodies to MuSK inhibit MuSK phosphorylation in fibroblasts expressing MuSK but not Lrp4, a context where MuSK phosphorylation is dependent upon MuSK dimerization and not facilitated by Lrp4.

MuSK is poorly tyrosine phosphorylated in transfected mammalian non-muscle cells and in yeast. Because MuSK has an unusually high Km for ATP (35), similar to the ATP concentration in muscle but higher than the ATP concentration in most cell types, the present inventors considered the possibility that this high Km for ATP restrained MuSK phosphorylation in non-muscle cell types. Because the insulin receptor has a lower Km for ATP, typical for receptor tyrosine kinases, the present inventors mutated two amino acids in the activation loop of MuSK to the corresponding residues in the insulin receptor, reasoning that these substitutions might destabilize the activation loop, lower the Km for ATP and increase MuSK phosphorylation in non-muscle cells.

Figure 3:
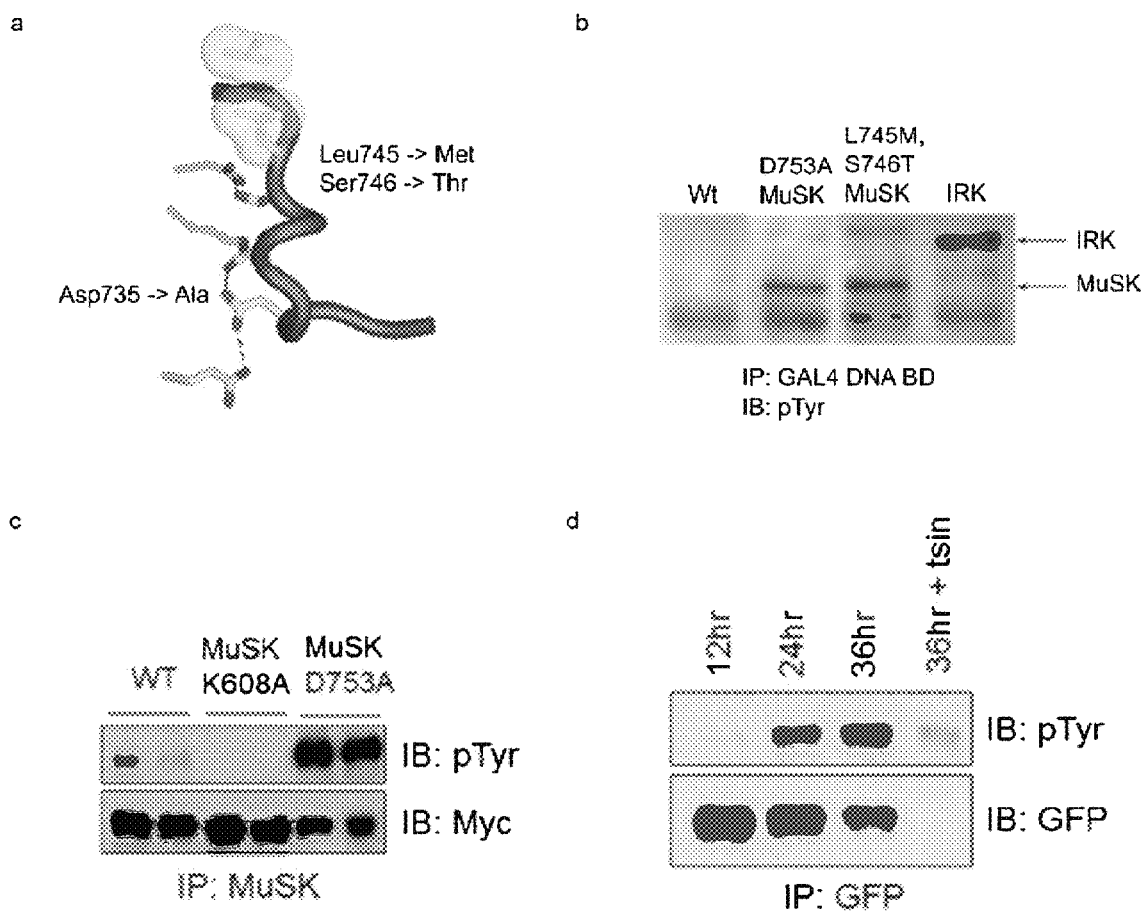
FIG. 3. IgG4 antibodies from MuSK MG patients fail to reduce MuSK phosphorylation in 3T3 cells transfected with MuSK but not Lrp4. (a) The diagram of the MuSK activation loop shows the substitutions in rodent MuSK that increase MuSK kinase activity. (b) MuSK tyrosine phosphorylation in yeast is enhanced to levels that are comparable to the insulin receptor (IRK) by mutation of D753 or L745/S746 in rodent MuSK (L746/S747 in human MuSK). Yeast were transformed with plasmids encoding fusion proteins between the DNA binding domain (BD) of GAL4 and MuSK or IRK. (c) MuSK tyrosine phosphorylation in 293 cells is enhanced 50-fold by mutation of D753. 293 cells were transfected with wild-type Myc-MuSK (22), Myc-MuSK K608A, a kinase-inactive form of MuSK, or Myc-MuSK D753A. (d) Tyrosine phosphorylation of MuSK L746M/S747T-GFP is detectable 24 h after transfection and increases over the next 12 h. Nearly all tyrosine phosphorylated MuSK is on the cell surface, as it is removed by digestion of cell surface proteins with trypsin. (e,f,g) Addition of IgG4 antibodies from MuSK MG patients but not a healthy control (HC) or an AChR MG patient at 12 h following transfection does not have significant effect on MuSK phosphorylation.

The present inventors generated an activation loop double mutant, MuSK L746M, S747T and found that this activation loop mutant, unlike wild-type MuSK, was efficiently tyrosine phosphorylated in non-muscle cells (FIG. 3a,b,c). 3T3 cells were transfected with the activated form of MuSK and MuSK phosphorylation was measured 12, 24 and 36 hours after transfection; MuSK phosphorylation was undetectable at 12 hr, but increased in a linear manner over the next 24 hr (FIG. 3d). In that mild trypsin treatment degraded MuSK, leading to the disappearance of the tyrosine phosphorylated MuSK band at ~110 kd (FIG. 3e), nearly all tyrosine phosphorylated MuSK was determined to be on the cell surface. The present inventors therefore treated transfected 3T3 cells with IgG4 antibodies to MuSK, beginning at 12 hr after transfection and measured MuSK phosphorylation at 24 and 36 hr. FIG. 3 shows that IgG4 from MuSK patients failed to inhibit MuSK phosphorylation (FIG. 3e,f,g). Because these antibodies completely block binding between Lrp4 and MuSK, but have no detectable effect on MuSK dimerization, inhibition of MuSK dimerization likely plays little if any role in pathogenesis.

MuSK Patient IgG4 Antibodies do not Deplete MuSK Cell Surface Expression.

Figure 4:
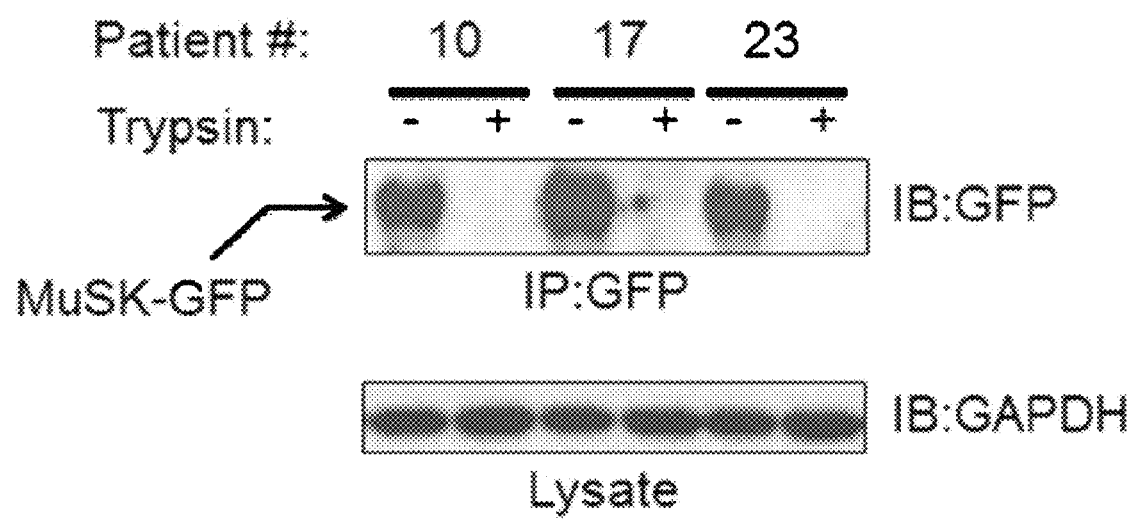
FIG. 4. IgG4 antibodies from MuSK MG patients do not reduce MuSK cell surface expression. 3T3 cells expressing MuSK were treated with MuSK MG IgG4 antibodies for 24 h (FIG. 3). Cells were harvested, or treated with trypsin prior to harvesting, and the level of MuSK and GAPDH expression were determined by Western blotting.

Nearly all MuSK expressed in 3T3 cells was on the cell surface and removed by mild trypsin treatment (FIG. 3c). Treatment of these cells with IgG4 patient antibodies did not alter the amount of MuSK expressed by 3T3 cells (FIG. 4), which was likewise found almost entirely on the cell surface and removed by mild trypsin treatment. In contrast, intracellular proteins, such as GAPDH, were not degraded by trypsin (FIG. 4). Thus, the pathogenic IgG4 antibodies to MuSK do not modulate and reduce MuSK cell surface expression in this context.

Discussion

MuSK MG is an IgG4 mediated autoimmune disease. Transfer of purified IgG4 from MuSK MG patients into immune-deficient mice causes myasthenic weakness that mimics the pathophysiology of patients with MuSK MG (13). These data show that the auto-antibodies exert their pathogenic effects independent of the immune system by binding to MuSK and interfering with normal neuromuscular physiology. The present studies show that pathogenic IgG4 antibodies to MuSK prevent Agrin from stimulating MuSK by blocking association between Lrp4 and MuSK. This inhibitory mechanism likely plays a key role in disrupting the structure of the synapse, compromising synaptic transmission and causing disease. Because the pathogenic antibodies do not decrease MuSK surface expression and only modestly affect MuSK dimerization, therapeutic strategies designed to increase MuSK activity may prove effective in treating MuSK MG.

All Dutch MuSK MG patients tested had strong immunoreactivity against the first Ig-like domain of MuSK. Five patients harbored additional reactivity against the Ig-like domain 2 in the ELISA. Other studies have reported that patients harbor auto-antibodies outside of the Ig-like domains, including the Frizzled-like domain (36,14,37). These differences might be caused by racial differences, and/or different disease states of the patients.

Other studies have explored an active immunization model of MuSK MG instead of a passive transfer model with patient auto-antibodies. Because rabbits lack the equivalent of human IgG4 antibodies, and mouse IgG also binds complement (38,39), the active immunization models lead to the production of classic, bivalent antibodies that cross-link antigens, deplete cell surface expression and engage complement. In addition, the MuSK epitopes recognized by these polyclonal antibody responses are unknown. As such, the nature of disease in the active immunization model is distinct from MuSK MG caused by human IgG4 antibodies.

Passive transfer of total IgG from MuSK MG patients into mice can stimulate rather than inhibit MuSK phosphorylation (40). Given the structure and function of IgG4 antibodies, as well as the present findings showing that IgG4 antibodies inhibit MuSK phosphorylation, it seems likely that stimulation of MuSK phosphorylation was due to IgG1-3 rather than IgG4 in these passive transfer experiments. Combining the IgG1-3 and IgG4 fractions therefore might mask individual effects of the different anti-MuSK IgG subclasses. Because IgG4 rather than IgG1-3 antibodies are pathogenic in Dutch MuSK MG patients (13), these findings, taken together, raise the possibility that different ethnic groups generate different immune responses to MuSK and that some MG patients carry IgG1-3 antibodies to MuSK that cause disease by other mechanisms.

MuSK is essential for all known aspects of presynaptic and postsynaptic differentiation (10,11,18). As such, antibodies that inhibit MuSK function would be expected to disrupt the architecture of the neuromuscular synapse as well as perturb neurotransmitter release and reception (41, 10,42,36,19,43,44,20). Because the synaptic accumulation of acetylcholinesterase (AChE), like all other postsynaptic proteins, depends upon MuSK (11), IgG4 antibodies to MuSK are likely to lower AChE expression at the synapse, which may explain the hypersensitivity of MuSK MG patients to AChE inhibitors.

In AChR MG, the decrease in AChR expression and function leads to a compensatory increase in neurotransmitter release, termed quantal content. An increase in quantal content, however, is not evident in MuSK MG (13,17,45). These findings suggest that MuSK plays an important role in this homeostatic response. Because muscle inactivity increases MuSK expression (46), antibodies to AChRs may stimulate MuSK expression and MuSK-dependent retrograde signaling, thereby increasing quantal content. Because MuSK signaling is required to cluster Lrp4, which serves as a retrograde signal for presynaptic differentiation (26), antibodies that inhibit MuSK are likely to compromise presynaptic differentiation and prevent a compensatory increase in transmitter release. If so, auto-antibodies to Lrp4 may likewise perturb presynaptic and postsynaptic differentiation (40,47,13,48,49).

Traditionally, IgG4 antibodies have been considered to have an anti-inflammatory role, as they have the potential to compete with IgG1-3 and prevent complement-mediated cell damage and inflammation. There is growing evidence, however, that IgG4 antibodies can have a pathogenic role, as IgG4 antibodies against desmoglein cause a skin-blistering disease, termed *Pemphigus* (50), and IgG4 antibodies to the phospholipase A2 receptor on podocytes are thought to contribute to membranous nephropathy (51). Moreover, IgG4 auto-antibodies to Leucine-rich glioma inactivated 1 (Lgi1), a regulator of the voltage-gated potassium channel that is important for synaptic transmission in the central nervous system, are thought to be responsible for limbic encephalitis (52). The mechanisms by which these IgG4 antibodies disrupt function and cause disease, however, are not understood. Our studies provide the first mechanistic understanding of an auto-immune disease caused by IgG4 antibodies and may shed light on the mechanisms of other IgG4 mediated auto-immune diseases.

This invention may be embodied in other forms or carried out in other ways without departing from the spirit or essential characteristics thereof. The present disclosure is therefore to be considered as in all aspects illustrate and not restrictive, the scope of the invention being indicated by the appended claims, and all changes which come within the meaning and range of equivalency are intended to be embraced therein.

Various references are cited throughout this Specification, each of which is incorporated herein by reference in its entirety.

REFERENCES

1. Lennon V A, Lindstrom J M, Seybold M E (1975) Experimental autoimmune myasthenia: A model of myasthenia gravis in rats and guinea pigs. J Exp Med 141: 1365-1375.
2. Lindstrom J M et al. (1976) Pathological mechanisms in experimental autoimmune myasthenia gravis. II. Passive transfer of experimental autoimmune myasthenia gravis in rats with anti-acetylcholine recepotr antibodies. J Exp Med 144:739-753.
3. Lindstrom J M, Einarson B L, Lennon V A, Seybold M E (1976) Pathological mechanisms in experimental autoimmune myasthenia gravis. I. Immunogenicity of syngeneic muscle acetylcholine receptor and quantitative extraction of receptor and antibody-receptor complexes from muscles of rats with experimental autoimmune myasthenia gravis. J Exp Med 144:726-738.
4. Rodgaard A et al. (1987) Acetylcholine receptor antibody in myasthenia gravis: predominance of IgG subclasses 1 and 3. Clin Exp Immunol 67:82-88.
5. Engel A G, Arahata K (1987) The membrane attack complex of complement at the endplate in myasthenia gravis. Ann N Y Acad Sci 505:326-332.
6. Drachman D B et al. (1978) Myasthenic antibodies cross-link acetylcholine receptors to accelerate degradation. N Engl J Med 298:1116-1122.
7. Drachman D B, Adams R N, Josifek L F, Self S G (1982) Functional activities of autoantibodies to acetylcholine receptors and the clinical severity of myasthenia gravis. N Engl J Med 307:769-775.
8. Christadoss P (1988) C5 gene influences the development of murine myasthenia gravis. J Immunol 140:2589-2592.
9. Papanastasiou D, Poulas K, Kokla A, Tzartos S J (2000) Prevention of passively transferred experimental autoimmune myasthenia gravis by Fab fragments of monoclonal antibodies directed against the main immunogenic region of the acetylcholine receptor. J Neuroimmunol 104:124-132.
10. Burden S J, Yumoto N, Zhang W (2013) The role of MuSK in synapse formation and neuromuscular disease. Cold Spring Harb Perspect Biol 5:a009167-
11. DeChiara T M et al. (1996) The receptor tyrosine kinase MuSK is required for neuromuscular junction formation in vivo. Cell 85:501-512.
12. Hoch W et al. (2001) Auto-antibodies to the receptor tyrosine kinase MuSK in patients with myasthenia gravis without acetylcholine receptor antibodies. Nat Med 7:365-368.
13. Klooster R et al. (2012) Muscle-specific kinase myasthenia gravis IgG4 autoantibodies cause severe neuromuscular junction dysfunction in mice. Brain 135:1081-1101.
14. McConville J et al. (2004) Detection and characterization of MuSK antibodies in seronegative myasthenia gravis. Ann Neurol 55:580-584.
15. Niks E H et al. (2008) Clinical fluctuations in MuSK myasthenia gravis are related to antigen-specific IgG4 instead of IgG1. J Neuroimmunol 195:151-156.

16. van der Neut K M et al. (2007) Anti-inflammatory activity of human IgG4 antibodies by dynamic Fab arm exchange. Science 317:1554-1557.
17. Mori S et al. (2012) Antibodies against muscle-specific kinase impair both presynaptic and postsynaptic functions in a murine model of myasthenia gravis. Am J Pathol 180:798-810.
18. Sanes J R, Lichtman J W (2001) Induction, assembly, maturation and maintenance of a postsynaptic apparatus. Nat Rev Neurosci 2:791-805.
19. Kim N et al. (2008) Lrp4 is a receptor for Agrin and forms a complex with MuSK. Cell 135:334-342.
20. Zhang B et al. (2008) LRP4 serves as a coreceptor of agrin. Neuron 60:285-297.
21. Zhang W, Coldefy A S, Hubbard S R, Burden S J (2011) Agrin binds to the N-terminal region of Lrp4 protein and stimulates association between Lrp4 and the first immunoglobulin-like domain in muscle-specific kinase (MuSK). J Biol Chem 286:40624-40630.
22. Hallock P T et al. (2010) Dok-7 regulates neuromuscular synapse formation by recruiting Crk and Crk-L. Genes Dev 24:2451-2461.
23. Hamuro J et al. (2008) Mutations causing DOK7 congenital myasthenia ablate functional motifs in Dok-7. J Biol Chem 283:5518-5524.
24. Okada K et al. (2006) The muscle protein Dok-7 is essential for neuromuscular synaptogenesis. Science 312:1802-1805.
25. Stiegler A L, Burden S J, Hubbard S R (2006) Crystal structure of the agrin-responsive immunoglobulin-like domains 1 and 2 of the receptor tyrosine kinase MuSK. J Mol Biol 364:424-433.
26. Yumoto N, Kim N, Burden S J (2012) Lrp4 is a retrograde signal for presynaptic differentiation at neuromuscular synapses. Nature 489:438-442.
27. Hesser B A, Henschel O, Witzemann V (2006) Synapse disassembly and formation of new synapses in postnatal muscle upon conditional inactivation of MuSK. Mol Cell Neurosci 31:470-480.
28. Kong X C, Barzaghi P, Ruegg M A (2004) Inhibition of synapse assembly in mammalian muscle in vivo by RNA interference. EMBO Rep 5:183-188.
29. Im S H, Barchan D, Fuchs S, Souroujon M C (2000) Mechanism of nasal tolerance induced by a recombinant fragment of acetylcholine receptor for treatment of experimental myasthenia gravis. J Neuroimmunol 111:161-168.
30. Lennon V A et al. (1991) Recombinant human acetylcholine receptor alpha-subunit induces chronic experimental autoimmune myasthenia gravis. J Immunol 146:2245-2248.
31. Lindstrom J, Campbell M, Nave B (1978) Specificities of antibodies to acetylcholine receptors. Muscle Nerve 1:140-145.
32. Lindstrom J, Einarson B (1979) Antigenic modulation and receptor loss in experimental autoimmune myasthenia gravis. Muscle Nerve 2:173-179.
33. Luo J et al. (2009) Main immunogenic region structure promotes binding of conformation-dependent myasthenia gravis autoantibodies, nicotinic acetylcholine receptor conformation maturation, and agonist sensitivity. J Neurosci 29:13898-13908.
34. Mahler M, Fritzler M J (2010) Epitope specificity and significance in systemic autoimmune diseases. Ann N Y Acad Sci 1183:267-287.
35. Till J H et al. (2002) Crystal structure of the MuSK tyrosine kinase: insights into receptor autoregulation. Structure 10:1187-1196.
36. Kawakami Y et al. (2011) Anti-MuSK autoantibodies block binding of collagen Q to MuSK. Neurology 77:1819-1826.
37. Takamori M, Nakamura T, Motomura M (2013) Antibodies against Wnt receptor of muscle-specific tyrosine kinase in myasthenia gravis. J Neuroimmunol 254:183-186.
38. Dangl J L et al. (1988) Segmental flexibility and complement fixation of genetically engineered chimeric human, rabbit and mouse antibodies. EMBO J 7:1989-1994.
39. Oi V T et al. (1984) Correlation between segmental flexibility and effector function of antibodies. Nature 307:136-140.
40. Cole R N et al. (2010) Patient autoantibodies deplete postsynaptic muscle-specific kinase leading to disassembly of the ACh receptor scaffold and myasthenia gravis in mice. J Physiol 588:3217-3229.
41. Amenta A R et al. (2012) Biglycan is an extracellular MuSK binding protein important for synapse stability. J Neurosci 32:2324-2334.
42. Cartaud A et al. (2004) MuSK is required for anchoring acetylcholinesterase at the neuromuscular junction. J Cell Biol 165:505-515.
43. Luo Z G et al. (2002) Regulation of AChR clustering by Dishevelled interacting with MuSK and PAK1. Neuron 35:489-505.
44. Ngo S T et al. (2012) Neuregulin-1 potentiates agrin-induced acetylcholine receptor clustering through muscle-specific kinase phosphorylation. J Cell Sci 125:1531-1543.
45. Viegas S et al. (2012) Passive and active immunization models of MuSK-Ab positive myasthenia: electrophysiological evidence for pre and postsynaptic defects. Exp Neurol 234:506-512.
46. Valenzuela D M et al. (1995) Receptor tyrosine kinase specific for the skeletal muscle lineage: expression in embryonic muscle, at the neuromuscular junction, and after injury. Neuron 15:573-584.
47. Higuchi O, Hamuro J, Motomura M, Yamanashi Y (2011) Autoantibodies to low-density lipoprotein receptor-related protein 4 in myasthenia gravis. Ann Neurol 69:418-422.
48. Pevzner A et al. (2012) Anti-LRP4 autoantibodies in AChR- and MuSK-antibody-negative myasthenia gravis. J Neurol 259:427-435.
49. Zhang B et al. (2012) Autoantibodies to lipoprotein-related protein 4 in patients with double-seronegative myasthenia gravis. Arch Neurol 69:445-451.
50. Di Z G et al. (2012) *Pemphigus* autoantibodies generated through somatic mutations target the desmoglein-3 cis-interface. J Clin Invest 122:3781-3790.
51. Beck L H, Jr. et al. (2009) M-type phospholipase A2 receptor as target antigen in idiopathic membranous nephropathy. N Engl J Med 361:11-21.
52. Irani S R et al. (2012) Morvan syndrome: clinical and serological observations in 29 cases. Ann Neurol 72:241-255.
53. Herbst R, Burden S J (2000) The juxtamembrane region of MuSK has a critical role in agrin-mediated signaling. EMBO J 19:67-77.

What is claimed is:

1. A method for improving motor function in a subject afflicted with muscle specific receptor kinase myasthenia gravis (MuSK-MG), the method comprising: administering a muscle specific receptor kinase (MuSK) first immunoglobulin-like domain 1 (Ig1) domain decoy that consists of residues 24 to 119 of SEQ ID NO: 2 and comprises a mutation whereby isoleucine at amino acid position 96 is replaced by an amino acid other than isoleucine to the subject in a therapeutically effective amount sufficient to increase MuSK activity in the subject and thereby improve motor function in the subject with MuSK-MG.

2. A method for treating a subject afflicted with muscle specific receptor kinase myasthenia gravis (MuSK-MG), the method comprising: administering a muscle specific receptor kinase (MuSK) first immunoglobulin-like domain 1 (Ig1) domain decoy that consists of residues 24 to 119 of SEQ ID NO: 2 and comprises a mutation whereby isoleucine at amino acid position 96 is replaced by an amino acid other than isoleucine to the subject in a therapeutically effective amount sufficient to increase MuSK activity in the subject and thereby treat the subject with MuSK-MG.

3. The method of claim 1 or 2, wherein the MuSK Ig1 domain decoy comprises a mutation whereby alanine (A) replaces isoleucine (I) at amino acid position 96 of MuSK.

4. The method of claim 1 or 2, further comprising measuring blood, serum, and/or cerebrospinal fluid levels of IgG4 antibodies specific for the Ig1 domain of MuSK in the subject before and after administering the MuSK Ig1 domain decoy and/or measuring levels of IgG4 antibodies specific for the Ig1 domain of MuSK in the subject at motor endplates before and after administering the MuSK Ig1 domain decoy.

5. The method of claim 1 or 2, wherein the therapeutically effective amount of the MuSK Ig1 domain decoy reduces levels of IgG4 antibodies specific for the Ig1 domain of MuSK.

6. The method of claim 1, wherein the improvement in motor function is measurable by determining innervation levels.

7. The method of claim 1 or 2, wherein the subject is a mammal.

8. The method of claim 1 or 2, wherein the subject is a human.

9. The method of claim 1 or 2, wherein the MuSK Ig1 domain decoy comprises a mutation whereby isoleucine at amino acid position 96 is replaced by an amino acid other than isoleucine, leucine, or valine.

10. A method for improving motor function in a subject afflicted with muscle specific receptor kinase myasthenia gravis (MuSK-MG), the method comprising: administering a muscle specific receptor kinase (MuSK) first immunoglobulin-like domain 1 (Ig1) domain decoy that consists of residues 24 to 119 of SEQ ID NO: 2 and comprises a mutation whereby isoleucine at amino acid position 96 is replaced by an amino acid other than isoleucine, and comprises a mutation whereby alanine (A) or asparagine (N) replaces threonine (T) at amino acid position 36 of MuSK and/or a mutation whereby lysine (K) replaces alanine (A) at amino acid position 114 of MuSK, to the subject in a therapeutically effective amount sufficient to increase MuSK activity in the subject and thereby improve motor function in the subject with MuSK-MG.

11. A method for treating a subject afflicted with muscle specific receptor kinase myasthenia gravis (MuSK-MG), the method comprising: administering a muscle specific receptor kinase (MuSK) first immunoglobulin-like domain 1 (Ig1) domain decoy that consists of residues 24 to 119 of SEQ ID NO: 2 and comprises a mutation whereby isoleucine at amino acid position 96 is replaced by an amino acid other than isoleucine, and comprises a mutation whereby alanine (A) or asparagine (N) replaces threonine (T) at amino acid position 36 of MuSK and/or a mutation whereby lysine (K) replaces alanine (A) at amino acid position 114 of MuSK, to the subject in a therapeutically effective amount sufficient to increase MuSK activity in the subject and thereby treat the subject with MuSK-MG.

* * * * *

UNITED STATES PATENT AND TRADEMARK OFFICE
CERTIFICATE OF CORRECTION

PATENT NO. : 9,574,015 B2
APPLICATION NO. : 14/486400
DATED : February 21, 2017
INVENTOR(S) : Steven J. Burden et al.

Page 1 of 1

It is certified that error appears in the above-identified patent and that said Letters Patent is hereby corrected as shown below:

In the Specification

At Column 1, Lines 16-19 replace:
"The research leading to the present invention was funded in part by Grant No. RO1 NS36193 awarded by the National Institutes of Health. The United States government has certain rights in the invention."

With:
--This invention was made with government support under grant number R01 NS036193 awarded by the National Institutes of Health. The government has certain rights in the invention.--

Signed and Sealed this
Eighteenth Day of June, 2019

Andrei Iancu
*Director of the United States Patent and Trademark Office*

SEQUENCE LISTING

<160> NUMBER OF SEQ ID NOS: 27

<210> SEQ ID NO 1
<211> LENGTH: 2666
<212> TYPE: DNA
<213> ORGANISM: Homo sapiens

<400> SEQUENCE: 1

| | | | | | |
|---|---|---|---|---|---|
| tgcgttgtcc | agaaggaact | tcgtcctgcg | tgagcctgga | ttaatcatga | gagagctcgt | 60 |
| caacattcca | ctggtacata | ttcttactct | ggttgccttc | agcggaactg | agaaacttcc | 120 |
| aaaagctcct | gtcatcacca | ctcctcttga | aacagtggat | gccttagttg | aagaagtggc | 180 |
| tactttcatg | tgtgcagtgg | aatcctaccc | ccagcctgag | atttcctgga | ctagaaataa | 240 |
| aattctcatt | aaactctttg | acacccggta | cagcatccgg | gagaatgggc | agctcctcac | 300 |
| catcctgagt | gtgaaagaca | gtgatgatgg | catttactgc | tgcacggcca | caatggtgt | 360 |
| gggaggagct | gtggagagtt | gtggagccct | gcaagtgaag | atgaaaccta | aataactcg | 420 |
| ccctcccata | aatgtgaaaa | taatagaggg | attaaaagca | gtcctaccat | gtactacaat | 480 |
| gggtaatccc | aaaccatcag | tgtcttggat | aaagggagac | agccctctca | gggaaaattc | 540 |
| ccgaattgca | gttcttgaat | ctgggagctt | gaggattcat | aacgtacaaa | aggaagatgc | 600 |
| aggacagtat | cgatgtgtgg | caaaaaacag | cctcgggaca | gcatattcca | agtggtgaa | 660 |
| gctggaagtt | gaggtttttg | ccaggatcct | gcgggctcct | gaatcccaca | atgtcacctt | 720 |
| tggctccttt | gtgaccctgc | actgtacagc | aacaggcatt | cctgtcccca | ccatcacctg | 780 |
| gattgaaaac | ggaaatgctg | tttcttctgg | gtccattcaa | gagagtgtga | agaccgagt | 840 |
| gattgactca | agactgcagc | tgtttatcac | caagccagga | ctctacacat | gcatagctac | 900 |
| caataagcat | ggggagaagt | tcagtactgc | caaggctgca | gccaccatca | gcatagcaga | 960 |
| atggagtaaa | ccacagaaag | ataacaaagg | ctactgcgcc | cagtacagag | gggaggtgtg | 1020 |
| taatgcagtc | ctggcaaaag | atgctcttgt | ttttctcaac | acctcctatg | cggaccctga | 1080 |
| ggaggcccaa | gagctactgg | tccacacggc | ctggaatgaa | ctgaaagtag | tgagcccagt | 1140 |
| ctgccggcca | gctgctgagg | ctttgttgtg | taaccacatc | ttccaggagt | gcagtcctgg | 1200 |
| agtagtgcct | actcctattc | ccatttgcag | agagtactgc | ttggcagtaa | aggagctctt | 1260 |
| ctgcgcaaaa | gaatggctgg | taatggaaga | gaagacccac | agaggactct | acagatccga | 1320 |
| gatgcatttg | ctgtccgtgc | cagaatgcag | caagcttccc | agcatgcatt | gggacccac | 1380 |
| ggcctgtgcc | agactgccac | atctagatta | taacaaagaa | aacctaaaaa | cattcccacc | 1440 |
| aatgacgtcc | tcaaagccaa | gtgtggacat | tccaaatctg | ccttcctcct | cctcttcttc | 1500 |
| cttctctgtc | tcacctacat | actccatgac | tgtaataatc | tccatcatgt | ccagctttgc | 1560 |
| aatatttgtg | cttcttacca | taactactct | ctattgctgc | cgaagaagaa | aacaatggaa | 1620 |
| aaataagaaa | agagaatcag | cagcagtaac | cctcaccaca | ctgccttctg | agctcttact | 1680 |
| agatagactt | catcccaacc | ccatgtacca | gaggatgccg | ctccttctga | accccaaatt | 1740 |
| gctcagcctg | gagtatccaa | ggaataacat | tgaatatgtg | agagacatcg | gagagggagc | 1800 |
| gtttggaagg | gtgtttcaag | caagggcacc | aggcttactt | ccctatgaac | ctttcactat | 1860 |
| ggtggcagta | aagatgctca | agaagaagc | ctcggcagat | atgcaagcgg | actttcagag | 1920 |
| ggaggcagcc | ctcatggcag | aatttgacaa | ccctaacatt | gtgaagctat | taggagtgtg | 1980 |
| tgctgtcggg | aagccaatgt | gcctgctctt | tgaatacatg | gcctatggtg | acctcaatga | 2040 |

```
gttcctccgc agcatgtccc ctcacaccgt gtgcagcctc agtcacagtg acttgtctat    2100
gagggctcag gtctccagcc ctgggccccc accccctctcc tgtgctgagc agctttgcat   2160
tgccaggcag gtggcagctg catggcctta cctctcagaa cgtaagtttg ttcaccgaga    2220
tttagccacc aggaactgcc tggtgggcga gaacatggtg gtgaaaattg ccgactttgg    2280
cctctccagg aacatctact cagcagacta ctacaaagct aatgaaaacg acgctatccc    2340
tatccgttgg atgccaccag agtccatttt ttataaccgc tacactacag agtctgatgt    2400
gtgggcctat ggcgtggtcc tctgggagat cttctcctat ggcctgcagc cctactatgg    2460
gatggcccat gaggaggtca tttactacgt gcgagatggc aacatcctct cctgccctga    2520
gaactgcccc gtggagctgt acaatctcat gcgtctatgt tggagcaagc tgcctgcaga    2580
cagacccagt tcaccagta ttcaccgaat tctggaacgc atgtgtgaga gggcagaggg     2640
aactgtgagt gtctaaggtt gaagac                                         2666
```

<210> SEQ ID NO 2
<211> LENGTH: 869
<212> TYPE: PRT
<213> ORGANISM: Homo sapiens

<400> SEQUENCE: 2

```
Met Arg Glu Leu Val Asn Ile Pro Leu Val His Ile Leu Thr Leu Val
  1               5                  10                  15

Ala Phe Ser Gly Thr Glu Lys Leu Pro Lys Ala Pro Val Ile Thr Thr
             20                  25                  30

Pro Leu Glu Thr Val Asp Ala Leu Val Glu Glu Val Ala Thr Phe Met
         35                  40                  45

Cys Ala Val Glu Ser Tyr Pro Gln Pro Glu Ile Ser Trp Thr Arg Asn
     50                  55                  60

Lys Ile Leu Ile Lys Leu Phe Asp Thr Arg Tyr Ser Ile Arg Glu Asn
 65                  70                  75                  80

Gly Gln Leu Leu Thr Ile Leu Ser Val Glu Asp Ser Asp Asp Gly Ile
                 85                  90                  95

Tyr Cys Cys Thr Ala Asn Asn Gly Val Gly Gly Ala Val Glu Ser Cys
            100                 105                 110

Gly Ala Leu Gln Val Lys Met Lys Pro Lys Ile Thr Arg Pro Pro Ile
        115                 120                 125

Asn Val Lys Ile Ile Glu Gly Leu Lys Ala Val Leu Pro Cys Thr Thr
    130                 135                 140

Met Gly Asn Pro Lys Pro Ser Val Ser Trp Ile Lys Gly Asp Ser Pro
145                 150                 155                 160

Leu Arg Glu Asn Ser Arg Ile Ala Val Leu Glu Ser Gly Ser Leu Arg
                165                 170                 175

Ile His Asn Val Gln Lys Glu Asp Ala Gly Gln Tyr Arg Cys Val Ala
            180                 185                 190

Lys Asn Ser Leu Gly Thr Ala Tyr Ser Lys Val Val Lys Leu Glu Val
        195                 200                 205

Glu Val Phe Ala Arg Ile Leu Arg Ala Pro Glu Ser His Asn Val Thr
    210                 215                 220

Phe Gly Ser Phe Val Thr Leu His Cys Thr Ala Thr Gly Ile Pro Val
225                 230                 235                 240

Pro Thr Ile Thr Trp Ile Glu Asn Gly Asn Ala Val Ser Ser Gly Ser
                245                 250                 255

Ile Gln Glu Ser Val Lys Asp Arg Val Ile Asp Ser Arg Leu Gln Leu
```

-continued

```
            260                 265                 270
Phe Ile Thr Lys Pro Gly Leu Tyr Thr Cys Ile Ala Thr Asn Lys His
            275                 280                 285
Gly Glu Lys Phe Ser Thr Ala Lys Ala Ala Thr Ile Ser Ile Ala
        290                 295                 300
Glu Trp Ser Lys Pro Gln Lys Asp Asn Lys Gly Tyr Cys Ala Gln Tyr
305                 310                 315                 320
Arg Gly Glu Val Cys Asn Ala Val Leu Ala Lys Asp Ala Leu Val Phe
                325                 330                 335
Leu Asn Thr Ser Tyr Ala Asp Pro Glu Glu Ala Gln Glu Leu Leu Val
            340                 345                 350
His Thr Ala Trp Asn Glu Leu Lys Val Val Ser Pro Val Cys Arg Pro
            355                 360                 365
Ala Ala Glu Ala Leu Leu Cys Asn His Ile Phe Gln Glu Cys Ser Pro
        370                 375                 380
Gly Val Val Pro Thr Pro Ile Pro Ile Cys Arg Glu Tyr Cys Leu Ala
385                 390                 395                 400
Val Lys Glu Leu Phe Cys Ala Lys Glu Trp Leu Val Met Glu Glu Lys
                405                 410                 415
Thr His Arg Gly Leu Tyr Arg Ser Glu Met His Leu Leu Ser Val Pro
            420                 425                 430
Glu Cys Ser Lys Leu Pro Ser Met His Trp Asp Pro Thr Ala Cys Ala
        435                 440                 445
Arg Leu Pro His Leu Asp Tyr Asn Lys Glu Asn Leu Lys Thr Phe Pro
        450                 455                 460
Pro Met Thr Ser Ser Lys Pro Ser Val Asp Ile Pro Asn Leu Pro Ser
465                 470                 475                 480
Ser Ser Ser Ser Ser Phe Ser Val Ser Pro Thr Tyr Ser Met Thr Val
                485                 490                 495
Ile Ile Ser Ile Met Ser Ser Phe Ala Ile Phe Val Leu Leu Thr Ile
            500                 505                 510
Thr Thr Leu Tyr Cys Cys Arg Arg Arg Lys Gln Trp Lys Asn Lys Lys
            515                 520                 525
Arg Glu Ser Ala Ala Val Thr Leu Thr Thr Leu Pro Ser Glu Leu Leu
        530                 535                 540
Leu Asp Arg Leu His Pro Asn Pro Met Tyr Gln Arg Met Pro Leu Leu
545                 550                 555                 560
Leu Asn Pro Lys Leu Leu Ser Leu Glu Tyr Pro Arg Asn Asn Ile Glu
                565                 570                 575
Tyr Val Arg Asp Ile Gly Glu Gly Ala Phe Gly Arg Val Phe Gln Ala
            580                 585                 590
Arg Ala Pro Gly Leu Leu Pro Tyr Glu Pro Phe Thr Met Val Ala Val
        595                 600                 605
Lys Met Leu Lys Glu Glu Ala Ser Ala Asp Met Gln Ala Asp Phe Gln
        610                 615                 620
Arg Glu Ala Ala Leu Met Ala Glu Phe Asp Asn Pro Asn Ile Val Lys
625                 630                 635                 640
Leu Leu Gly Val Cys Ala Val Gly Lys Pro Met Cys Leu Leu Phe Glu
                645                 650                 655
Tyr Met Ala Tyr Gly Asp Leu Asn Glu Phe Leu Arg Ser Met Ser Pro
            660                 665                 670
His Thr Val Cys Ser Leu Ser His Ser Asp Leu Ser Met Arg Ala Gln
            675                 680                 685
```

```
Val Ser Ser Pro Gly Pro Pro Pro Leu Ser Cys Ala Glu Gln Leu Cys
        690             695                 700
Ile Ala Arg Gln Val Ala Ala Gly Met Ala Tyr Leu Ser Glu Arg Lys
705             710                 715                 720
Phe Val His Arg Asp Leu Ala Thr Arg Asn Cys Leu Val Gly Glu Asn
            725                 730                 735
Met Val Val Lys Ile Ala Asp Phe Gly Leu Ser Arg Asn Ile Tyr Ser
            740                 745                 750
Ala Asp Tyr Tyr Lys Ala Asn Glu Asn Asp Ala Ile Pro Ile Arg Trp
            755                 760                 765
Met Pro Pro Glu Ser Ile Phe Tyr Asn Arg Tyr Thr Thr Glu Ser Asp
770                 775                 780
Val Trp Ala Tyr Gly Val Val Leu Trp Glu Ile Phe Ser Tyr Gly Leu
785                 790                 795                 800
Gln Pro Tyr Tyr Gly Met Ala His Glu Glu Val Ile Tyr Tyr Val Arg
                805                 810                 815
Asp Gly Asn Ile Leu Ser Cys Pro Glu Asn Cys Pro Val Glu Leu Tyr
                820                 825                 830
Asn Leu Met Arg Leu Cys Trp Ser Lys Leu Pro Ala Asp Arg Pro Ser
            835                 840                 845
Phe Thr Ser Ile His Arg Ile Leu Glu Arg Met Cys Glu Arg Ala Glu
        850                 855                 860
Gly Thr Val Ser Val
865

<210> SEQ ID NO 3
<211> LENGTH: 2772
<212> TYPE: DNA
<213> ORGANISM: Homo sapiens

<400> SEQUENCE: 3
gtggagctgc tgacacaaac agtcattagc agacaaccct tttgcaacaa agtatgcttt      60
aaaatgtaaa ctgtggagcc attttccttg cgttgtccag aaggaacttc gtcctgcgtg     120
agcctggatt aatcatgaga gagctcgtca acattccact ggtacatatt cttactctgg     180
ttgccttcag cggaactgag aaacttccaa aagctcctgt catcaccact cctcttgaaa     240
cagtggatgc cttagttgaa gaagtggcta ctttcatgtg tgcagtggaa tcctacccc     300 agcctgagat tcctggact agaaataaaa ttctcattaa actctttgac acccggtaca     360
gcatccggga gaatgggcag ctcctcacca tcctgagtgt ggaagacagt gatgatggca     420
tttactgctg cacggccaac aatggtgtgg aggagctgtg gagagttgt ggagccctgc     480 aagtgaagat gaaacctaaa ataactcgtc ctcccataaa tgtgaaaata atagagggat     540
taaaagcagt cctaccatgt actacaatgg gtaatcccaa accatcagtg tcttggataa     600
agggagacag ccctctcagg gaaaattccc gaattgcagt tcttgaatct gggagcttga     660
ggattcataa cgtacaaaag gaagatgcag acagtatcg atgtgtggca aaaaacagcc     720
tcgggacagc atattccaaa gtggtgaagc tggaagttga ggttttttgcc aggatcctgc     780 gggctcctga atcccacaat gtcacctttg ctcctttgt gaccctgcac tgtacagcaa     840
caggcattcc tgtccccacc atcacctgga ttgaaaacgg aaatgctgtt tcttctgggt     900
ccattcaaga gagtgtgaaa gaccgagtga ttgactcaag actgcagctg tttatcacca     960
agccaggact ctacacatgc atagctacca ataagcatgg ggagaagttc agtactgcca    1020
```

-continued

| | |
|---|---|
| aggctgcagc caccatcagc atagcagaaa tgttgttcat ttcttctttc agtaaaccac | 1080 |
| agaaagataa caaaggctac tgcgcccagt acagagggga ggtgtgtaat gcagtcctgg | 1140 |
| caaaagatgc tcttgttttt ctcaacacct cctatgcgga ccctgaggag gcccaagagc | 1200 |
| tactggtcca cacggcctgg aatgaactga aagtagtgag cccagtctgc cggccagctg | 1260 |
| ctgaggcttt gttgtgtaac cacatcttcc aggagtgcag tcctggagta gtgcctactc | 1320 |
| ctattcccat ttgcagagag tactgcttgg cagtaaagga gctcttctgc gcaaaagaat | 1380 |
| ggctggtaat ggaagagaag acccacagag gactctacag atccgagatg catttgctgt | 1440 |
| ccgtgccaga tgcagcaag cttcccagca tgcattggga ccccacggcc tgtgccagac | 1500 |
| tgccacatct agattataac aaagaaaacc taaaaacatt cccaccaatg acgtcctcaa | 1560 |
| agccaagtgt ggacattcca aatctgcctt cctcctcctc ttcttccttc tctgtctcac | 1620 |
| ctacatactc catgactgta ataatctcca tcatgtccag ctttgcaata tttgtgcttc | 1680 |
| ttaccataac tactctctat tgctgccgaa gaagaaaaca atggaaaaat aagaaaagag | 1740 |
| aatcagcagc agtaaccctc accacactgc cttctgagct cttactagat agacttcatc | 1800 |
| ccaaccccat gtaccagagg atgccgctcc ttctgaaccc caaattgctc agcctggagt | 1860 |
| atccaaggaa taacattgaa tatgtgagag acatcggaga gggagcgttt ggaagggtgt | 1920 |
| ttcaagcaag ggcaccaggc ttacttccct atgaaccttt cactatggtg gcagtaaaga | 1980 |
| tgctcaaaga agaagcctcg gcagatatgc aagcggactt tcagagggag gcagccctca | 2040 |
| tggcagaatt tgacaaccct aacattgtga agctattagg agtgtgtgct gtcgggaagc | 2100 |
| caatgtgcct gctcttttgaa tacatggcct atggtgacct caatgagttc ctccgcagca | 2160 |
| tgtccctca ccgtgtgc agcctcagtc acagtgactt gtctatgagg gctcaggtct | 2220 |
| ccagccctgg gccccaccc ctctcctgtg ctgagcagct ttgcattgcc aggcaggtgg | 2280 |
| cagctggcat ggcttacctc tcagaacgta agtttgttca ccgagattta gccaccagga | 2340 |
| actgcctggt gggcgagaac atggtggtga aaattgccga cttttggcctc tccaggaaca | 2400 |
| tctactcagc agactactac aaagctaatg aaaacgacgc tatccctatc cgttggatgc | 2460 |
| caccagagtc cattttttat aaccgctaca ctacagagtc tgatgtgtgg gcctatggcg | 2520 |
| tggtcctctg ggagatcttc tcctatggcc tgcagcccta ctatgggatg gcccatgagg | 2580 |
| aggtcattta ctacgtgcga gatggcaaca tcctctcctg ccctgagaac tgccccgtgg | 2640 |
| agctgtacaa tctcatgcgt ctatgttgga gcaagctgcc tgcagacaga cccagtttca | 2700 |
| ccagtattca ccgaattctg gaacgcatgt gtgagagggc agaggaact gtgagtgtct | 2760 |
| aaggttgaag ac | 2772 |

<210> SEQ ID NO 4
<211> LENGTH: 8
<212> TYPE: PRT
<213> ORGANISM: Homo sapiens

<400> SEQUENCE: 4

Gly Ala Ala Asp Thr Asn Ser His
1               5

<210> SEQ ID NO 5
<211> LENGTH: 473
<212> TYPE: PRT
<213> ORGANISM: Homo sapiens

<400> SEQUENCE: 5

-continued

```
Thr Glu Lys Leu Pro Lys Ala Pro Val Ile Thr Thr Pro Leu Glu Thr
 1               5                  10                  15
Val Asp Ala Leu Val Glu Val Ala Thr Phe Met Cys Ala Val Glu
            20                  25                  30
Ser Tyr Pro Gln Pro Glu Ile Ser Trp Thr Arg Asn Lys Ile Leu Ile
            35                  40                  45
Lys Leu Phe Asp Thr Arg Tyr Ser Ile Arg Glu Asn Gly Gln Leu Leu
 50              55                  60
Thr Ile Leu Ser Val Glu Asp Ser Asp Gly Ile Tyr Cys Cys Thr
 65                  70                  75              80
Ala Asn Asn Gly Val Gly Gly Ala Val Glu Ser Cys Gly Ala Leu Gln
                85                  90                  95
Val Lys Met Lys Pro Lys Ile Thr Arg Pro Pro Ile Asn Val Lys Ile
            100                 105                 110
Ile Glu Gly Leu Lys Ala Val Leu Pro Cys Thr Thr Met Gly Asn Pro
            115                 120                 125
Lys Pro Ser Val Ser Trp Ile Lys Gly Asp Ser Pro Leu Arg Glu Asn
 130                 135                 140
Ser Arg Ile Ala Val Leu Glu Ser Gly Ser Leu Arg Ile His Asn Val
145                 150                 155                 160
Gln Lys Glu Asp Ala Gly Gln Tyr Arg Cys Val Ala Lys Asn Ser Leu
            165                 170                 175
Gly Thr Ala Tyr Ser Lys Val Val Lys Leu Glu Val Glu Val Phe Ala
            180                 185                 190
Arg Ile Leu Arg Ala Pro Glu Ser His Asn Val Thr Phe Gly Ser Phe
            195                 200                 205
Val Thr Leu His Cys Thr Ala Thr Gly Ile Pro Val Pro Thr Ile Thr
            210                 215                 220
Trp Ile Glu Asn Gly Asn Ala Val Ser Ser Gly Ser Ile Gln Glu Ser
225                 230                 235                 240
Val Lys Asp Arg Val Ile Asp Ser Arg Leu Gln Leu Phe Ile Thr Lys
            245                 250                 255
Pro Gly Leu Tyr Thr Cys Ile Ala Thr Asn Lys His Gly Glu Lys Phe
            260                 265                 270
Ser Thr Ala Lys Ala Ala Ala Thr Ile Ser Ile Ala Glu Trp Ser Lys
            275                 280                 285
Pro Gln Lys Asp Asn Lys Gly Tyr Cys Ala Gln Tyr Arg Gly Glu Val
            290                 295                 300
Cys Asn Ala Val Leu Ala Lys Asp Ala Leu Val Phe Leu Asn Thr Ser
305                 310                 315                 320
Tyr Ala Asp Pro Glu Glu Ala Gln Glu Leu Leu Val His Thr Ala Trp
            325                 330                 335
Asn Glu Leu Lys Val Val Ser Pro Val Cys Arg Pro Ala Ala Glu Ala
            340                 345                 350
Leu Leu Cys Asn His Ile Phe Gln Glu Cys Ser Pro Gly Val Val Pro
            355                 360                 365
Thr Pro Ile Pro Ile Cys Arg Glu Tyr Cys Leu Ala Val Lys Glu Leu
            370                 375                 380
Phe Cys Ala Lys Glu Trp Leu Val Met Glu Glu Lys Thr His Arg Gly
385                 390                 395                 400
Leu Tyr Arg Ser Glu Met His Leu Leu Ser Val Pro Glu Cys Ser Lys
            405                 410                 415
Leu Pro Ser Met His Trp Asp Pro Thr Ala Cys Ala Arg Leu Pro His
```

```
                         420                 425                 430
Leu Asp Tyr Asn Lys Glu Asn Leu Lys Thr Phe Pro Pro Met Thr Ser
            435                 440                 445

Ser Lys Pro Ser Val Asp Ile Pro Asn Leu Pro Ser Ser Ser Ser Ser
    450                 455                 460

Ser Phe Ser Val Ser Pro Thr Tyr Ser
465                 470

<210> SEQ ID NO 6
<211> LENGTH: 420
<212> TYPE: PRT
<213> ORGANISM: Homo sapiens

<400> SEQUENCE: 6

Arg Tyr Ser Ile Arg Glu Asn Gly Gln Leu Leu Thr Ile Leu Ser Val
 1               5                  10                  15

Glu Asp Ser Asp Asp Gly Ile Tyr Cys Cys Thr Ala Asn Asn Gly Val
            20                  25                  30

Gly Gly Ala Val Glu Ser Cys Gly Ala Leu Gln Val Lys Met Lys Pro
        35                  40                  45

Lys Ile Thr Arg Pro Pro Ile Asn Val Lys Ile Ile Glu Gly Leu Lys
 50                  55                  60

Ala Val Leu Pro Cys Thr Thr Met Gly Asn Pro Lys Pro Ser Val Ser
65                  70                  75                  80

Trp Ile Lys Gly Asp Ser Pro Leu Arg Glu Asn Ser Arg Ile Ala Val
                85                  90                  95

Leu Glu Ser Gly Ser Leu Arg Ile His Asn Val Gln Lys Glu Asp Ala
            100                 105                 110

Gly Gln Tyr Arg Cys Val Ala Lys Asn Ser Leu Gly Thr Ala Tyr Ser
        115                 120                 125

Lys Val Val Lys Leu Glu Val Glu Val Phe Ala Arg Ile Leu Arg Ala
130                 135                 140

Pro Glu Ser His Asn Val Thr Phe Gly Ser Phe Val Thr Leu His Cys
145                 150                 155                 160

Thr Ala Thr Gly Ile Pro Val Pro Thr Ile Thr Trp Ile Glu Asn Gly
                165                 170                 175

Asn Ala Val Ser Ser Gly Ser Ile Gln Glu Ser Val Lys Asp Arg Val
            180                 185                 190

Ile Asp Ser Arg Leu Gln Leu Phe Ile Thr Lys Pro Gly Leu Tyr Thr
        195                 200                 205

Cys Ile Ala Thr Asn Lys His Gly Glu Lys Phe Ser Thr Ala Lys Ala
    210                 215                 220

Ala Ala Thr Ile Ser Ile Ala Glu Trp Ser Lys Pro Gln Lys Asp Asn
225                 230                 235                 240

Lys Gly Tyr Cys Ala Gln Tyr Arg Gly Glu Val Cys Asn Ala Val Leu
                245                 250                 255

Ala Lys Asp Ala Leu Val Phe Leu Asn Thr Ser Tyr Ala Asp Pro Glu
            260                 265                 270

Glu Ala Gln Glu Leu Leu Val His Thr Ala Trp Asn Glu Leu Lys Val
        275                 280                 285

Val Ser Pro Val Cys Arg Pro Ala Ala Glu Ala Leu Leu Cys Asn His
    290                 295                 300

Ile Phe Gln Glu Cys Ser Pro Gly Val Val Pro Thr Pro Ile Pro Ile
305                 310                 315                 320
```

```
Cys Arg Glu Tyr Cys Leu Ala Val Lys Glu Leu Phe Cys Ala Lys Glu
            325                 330                 335

Trp Leu Val Met Glu Glu Lys Thr His Arg Gly Leu Tyr Arg Ser Glu
        340                 345                 350

Met His Leu Leu Ser Val Pro Glu Cys Ser Lys Leu Pro Ser Met His
            355                 360                 365

Trp Asp Pro Thr Ala Cys Ala Arg Leu Pro His Leu Asp Tyr Asn Lys
370                 375                 380

Glu Asn Leu Lys Thr Phe Pro Pro Met Thr Ser Ser Lys Pro Ser Val
385                 390                 395                 400

Asp Ile Pro Asn Leu Pro Ser Ser Ser Ser Ser Ser Phe Ser Val Ser
                405                 410                 415

Pro Thr Tyr Ser
            420

<210> SEQ ID NO 7
<211> LENGTH: 281
<212> TYPE: PRT
<213> ORGANISM: Homo sapiens

<400> SEQUENCE: 7

Arg Ile Leu Arg Ala Pro Glu Ser His Asn Val Thr Phe Gly Ser Phe
1               5                   10                  15

Val Thr Leu His Cys Thr Ala Thr Gly Ile Pro Val Pro Thr Ile Thr
            20                  25                  30

Trp Ile Glu Asn Gly Asn Ala Val Ser Ser Gly Ser Ile Gln Glu Ser
        35                  40                  45

Val Lys Asp Arg Val Ile Asp Ser Arg Leu Gln Leu Phe Ile Thr Lys
    50                  55                  60

Pro Gly Leu Tyr Thr Cys Ile Ala Thr Asn Lys His Gly Glu Lys Phe
65                  70                  75                  80

Ser Thr Ala Lys Ala Ala Ala Thr Ile Ser Ile Ala Glu Trp Ser Lys
                85                  90                  95

Pro Gln Lys Asp Asn Lys Gly Tyr Cys Ala Gln Tyr Arg Gly Glu Val
            100                 105                 110

Cys Asn Ala Val Leu Ala Lys Asp Ala Leu Val Phe Leu Asn Thr Ser
        115                 120                 125

Tyr Ala Asp Pro Glu Glu Ala Gln Glu Leu Leu Val His Thr Ala Trp
    130                 135                 140

Asn Glu Leu Lys Val Val Ser Pro Val Cys Arg Pro Ala Ala Glu Ala
145                 150                 155                 160

Leu Leu Cys Asn His Ile Phe Gln Glu Cys Ser Pro Gly Val Val Pro
                165                 170                 175

Thr Pro Ile Pro Ile Cys Arg Glu Tyr Cys Leu Ala Val Lys Glu Leu
            180                 185                 190

Phe Cys Ala Lys Glu Trp Leu Val Met Glu Glu Lys Thr His Arg Gly
        195                 200                 205

Leu Tyr Arg Ser Glu Met His Leu Leu Ser Val Pro Glu Cys Ser Lys
    210                 215                 220

Leu Pro Ser Met His Trp Asp Pro Thr Ala Cys Ala Arg Leu Pro His
225                 230                 235                 240

Leu Asp Tyr Asn Lys Glu Asn Leu Lys Thr Phe Pro Pro Met Thr Ser
                245                 250                 255

Ser Lys Pro Ser Val Asp Ile Pro Asn Leu Pro Ser Ser Ser Ser Ser
            260                 265                 270
```

```
Ser Phe Ser Val Ser Pro Thr Tyr Ser
        275                 280
```

<210> SEQ ID NO 8
<211> LENGTH: 138
<212> TYPE: PRT
<213> ORGANISM: Homo sapiens

<400> SEQUENCE: 8

```
Asn Lys Gly Tyr Cys Ala Gln Tyr Arg Gly Glu Val Cys Asn Ala Val
 1               5                  10                 15

Leu Ala Lys Asp Ala Leu Val Phe Leu Asn Thr Ser Tyr Ala Asp Pro
            20                  25                 30

Glu Glu Ala Gln Glu Leu Leu Val His Thr Ala Trp Asn Glu Leu Lys
        35                  40                  45

Val Val Ser Pro Val Cys Arg Pro Ala Ala Glu Ala Leu Leu Cys Asn
    50                  55                  60

His Ile Phe Gln Glu Cys Ser Pro Gly Val Val Pro Thr Pro Ile Pro
 65                 70                  75                  80

Ile Cys Arg Glu Tyr Cys Leu Ala Val Lys Glu Leu Phe Cys Ala Lys
                85                  90                  95

Glu Trp Leu Val Met Glu Glu Lys Thr His Arg Gly Leu Tyr Arg Ser
            100                 105                110

Glu Met His Leu Leu Ser Val Pro Glu Cys Ser Lys Leu Pro Ser Met
        115                 120                 125

His Trp Asp Pro Thr Ala Cys Ala Arg Leu
    130                 135
```

<210> SEQ ID NO 9
<211> LENGTH: 105
<212> TYPE: PRT
<213> ORGANISM: Homo sapiens

<400> SEQUENCE: 9

```
Thr Glu Lys Leu Pro Lys Ala Pro Val Ile Thr Thr Pro Leu Glu Thr
 1               5                  10                 15

Val Asp Ala Leu Val Glu Glu Val Ala Thr Phe Met Cys Ala Val Glu
            20                  25                 30

Ser Tyr Pro Gln Pro Glu Ile Ser Trp Thr Arg Asn Lys Ile Leu Ile
        35                  40                  45

Lys Leu Phe Asp Thr Arg Tyr Ser Ile Arg Glu Asn Gly Gln Leu Leu
    50                  55                  60

Thr Ile Leu Ser Val Glu Asp Ser Asp Asp Gly Ile Tyr Cys Cys Thr
 65                 70                  75                  80

Ala Asn Asn Gly Val Gly Gly Ala Val Glu Ser Cys Gly Ala Leu Gln
                85                  90                  95

Val Lys Met Lys Pro Lys Ile Thr Arg
            100                 105
```

<210> SEQ ID NO 10
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 10
gacctcgaga tgagagagct cgtcaacatt ccactg                36

<210> SEQ ID NO 11
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 11
ctctcccgtc tcccttgaca ctcacagacc atggcgt    37

<210> SEQ ID NO 12
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 12
gccttcagcg gaactgagaa acctaaaata actcgccctc cc    42

<210> SEQ ID NO 13
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 13
agcgaattca tgagagagct cgtcaacatt c    31

<210> SEQ ID NO 14
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 14
gagtggatgt atgaggtact gatctagacg t    31

<210> SEQ ID NO 15
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 15
actttggcat gaccaggaac atctactcag ca    32

<210> SEQ ID NO 16
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 16
agatgttcct ggtcatgcca aagtcggcaa ttttcac    37

<210> SEQ ID NO 17
<211> LENGTH: 36
<212> TYPE: DNA
<213> ORGANISM: Artificial Sequence
<220> FEATURE:

-continued

<223> OTHER INFORMATION: Synthetic oligonucleotide

<400> SEQUENCE: 17
gacctcgaga tgagagagct cgtcaacatt ccactg                             36

<210> SEQ ID NO 18
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 18
gagagggcag agggaactgt gagtgtctgg taccgca                            37

<210> SEQ ID NO 19
<211> LENGTH: 90
<212> TYPE: PRT
<213> ORGANISM: Homo sapiens

<400> SEQUENCE: 19

Pro Val Ile Thr Thr Pro Leu Glu Thr Val Asp Ala Leu Val Glu Glu
1               5                   10                  15

Val Ala Thr Phe Met Cys Ala Val Glu Ser Tyr Pro Gln Pro Glu Ile
            20                  25                  30

Ser Trp Thr Arg Asn Lys Ile Leu Ile Lys Leu Phe Asp Thr Arg Tyr
        35                  40                  45

Ser Ile Arg Glu Asn Gly Gln Leu Leu Thr Ile Leu Ser Val Glu Asp
    50                  55                  60

Ser Asp Asp Gly Ile Tyr Cys Cys Thr Ala Asn Asn Gly Val Gly Gly
65                  70                  75                  80

Ala Val Glu Ser Cys Gly Ala Leu Gln Val
                85                  90

<210> SEQ ID NO 20
<211> LENGTH: 10
<212> TYPE: PRT
<213> ORGANISM: Homo sapiens

<400> SEQUENCE: 20

Gln Thr Thr Leu Leu Gln Gln Ser Met Leu
1               5                   10

<210> SEQ ID NO 21
<211> LENGTH: 899
<212> TYPE: PRT
<213> ORGANISM: Homo sapiens

<400> SEQUENCE: 21

Asn Val Asn Cys Gly Ala Ile Phe Leu Ala Leu Ser Arg Arg Asn Phe
1               5                   10                  15

Val Leu Arg Glu Pro Gly Leu Ile Met Arg Glu Leu Val Asn Ile Pro
            20                  25                  30

Leu Val His Ile Leu Thr Leu Val Ala Phe Ser Gly Thr Glu Lys Leu
        35                  40                  45

Pro Lys Ala Pro Val Ile Thr Thr Pro Leu Glu Thr Val Asp Ala Leu
    50                  55                  60

Val Glu Glu Val Ala Thr Phe Met Cys Ala Val Glu Ser Tyr Pro Gln
65                  70                  75                  80

Pro Glu Ile Ser Trp Thr Arg Asn Lys Ile Leu Ile Lys Leu Phe Asp

```
                  85                  90                  95
Thr Arg Tyr Ser Ile Arg Glu Asn Gly Gln Leu Leu Thr Ile Leu Ser
                100                 105                 110

Val Glu Asp Ser Asp Asp Gly Ile Tyr Cys Cys Thr Ala Asn Asn Gly
            115                 120                 125

Val Gly Gly Ala Val Glu Ser Cys Gly Ala Leu Gln Val Lys Met Lys
    130                 135                 140

Pro Lys Ile Thr Arg Pro Pro Ile Asn Val Lys Ile Glu Gly Leu
145                 150                 155                 160

Lys Ala Val Leu Pro Cys Thr Thr Met Gly Asn Pro Lys Pro Ser Val
                165                 170                 175

Ser Trp Ile Lys Gly Asp Ser Pro Leu Arg Glu Asn Ser Arg Ile Ala
            180                 185                 190

Val Leu Glu Ser Gly Ser Leu Arg Ile His Asn Val Gln Lys Glu Asp
        195                 200                 205

Ala Gly Gln Tyr Arg Cys Val Ala Lys Asn Ser Leu Gly Thr Ala Tyr
    210                 215                 220

Ser Lys Val Val Lys Leu Glu Val Glu Val Phe Ala Arg Ile Leu Arg
225                 230                 235                 240

Ala Pro Glu Ser His Asn Val Thr Phe Gly Ser Phe Val Thr Leu His
                245                 250                 255

Cys Thr Ala Thr Gly Ile Pro Val Pro Thr Ile Thr Trp Ile Glu Asn
            260                 265                 270

Gly Asn Ala Val Ser Ser Gly Ser Ile Gln Glu Ser Val Lys Asp Arg
        275                 280                 285

Val Ile Asp Ser Arg Leu Gln Leu Phe Ile Thr Lys Pro Gly Leu Tyr
    290                 295                 300

Thr Cys Ile Ala Thr Asn Lys His Gly Glu Lys Phe Ser Thr Ala Lys
305                 310                 315                 320

Ala Ala Ala Thr Ile Ser Ile Ala Glu Met Leu Phe Ile Ser Ser Phe
                325                 330                 335

Ser Lys Pro Gln Lys Asp Asn Lys Gly Tyr Cys Ala Gln Tyr Arg Gly
            340                 345                 350

Glu Val Cys Asn Ala Val Leu Ala Lys Asp Ala Leu Val Phe Leu Asn
        355                 360                 365

Thr Ser Tyr Ala Asp Pro Glu Glu Ala Gln Glu Leu Leu Val His Thr
    370                 375                 380

Ala Trp Asn Glu Leu Lys Val Val Ser Pro Val Cys Arg Pro Ala Ala
385                 390                 395                 400

Glu Ala Leu Leu Cys Asn His Ile Phe Gln Glu Cys Ser Pro Gly Val
                405                 410                 415

Val Pro Thr Pro Ile Pro Ile Cys Arg Glu Tyr Cys Leu Ala Val Lys
            420                 425                 430

Glu Leu Phe Cys Ala Lys Glu Trp Leu Val Met Glu Glu Lys Thr His
        435                 440                 445

Arg Gly Leu Tyr Arg Ser Glu Met His Leu Leu Ser Val Pro Glu Cys
    450                 455                 460

Ser Lys Leu Pro Ser Met His Trp Asp Pro Thr Ala Cys Ala Arg Leu
465                 470                 475                 480

Pro His Leu Asp Tyr Asn Lys Glu Asn Leu Lys Thr Phe Pro Pro Met
                485                 490                 495

Thr Ser Ser Lys Pro Ser Val Asp Ile Pro Asn Leu Pro Ser Ser Ser
            500                 505                 510
```

Ser Ser Ser Phe Ser Val Ser Pro Thr Tyr Ser Met Thr Val Ile Ile
            515                 520                 525

Ser Ile Met Ser Ser Phe Ala Ile Phe Val Leu Leu Thr Ile Thr Thr
        530                 535                 540

Leu Tyr Cys Cys Arg Arg Arg Lys Gln Trp Lys Asn Lys Lys Arg Glu
545                 550                 555                 560

Ser Ala Ala Val Thr Leu Thr Thr Leu Pro Ser Glu Leu Leu Leu Asp
                565                 570                 575

Arg Leu His Pro Asn Pro Met Tyr Gln Arg Met Pro Leu Leu Leu Asn
            580                 585                 590

Pro Lys Leu Leu Ser Leu Glu Tyr Pro Arg Asn Asn Ile Glu Tyr Val
        595                 600                 605

Arg Asp Ile Gly Glu Gly Ala Phe Gly Arg Val Phe Gln Ala Arg Ala
610                 615                 620

Pro Gly Leu Leu Pro Tyr Glu Pro Phe Thr Met Val Ala Val Lys Met
625                 630                 635                 640

Leu Lys Glu Glu Ala Ser Ala Asp Met Gln Ala Asp Phe Gln Arg Glu
                645                 650                 655

Ala Ala Leu Met Ala Glu Phe Asp Asn Pro Asn Ile Val Lys Leu Leu
            660                 665                 670

Gly Val Cys Ala Val Gly Lys Pro Met Cys Leu Leu Phe Glu Tyr Met
        675                 680                 685

Ala Tyr Gly Asp Leu Asn Glu Phe Leu Arg Ser Met Ser Pro His Thr
690                 695                 700

Val Cys Ser Leu Ser His Ser Asp Leu Ser Met Arg Ala Gln Val Ser
705                 710                 715                 720

Ser Pro Gly Pro Pro Pro Leu Ser Cys Ala Glu Gln Leu Cys Ile Ala
                725                 730                 735

Arg Gln Val Ala Ala Gly Met Ala Tyr Leu Ser Glu Arg Lys Phe Val
            740                 745                 750

His Arg Asp Leu Ala Thr Arg Asn Cys Leu Val Gly Glu Asn Met Val
        755                 760                 765

Val Lys Ile Ala Asp Phe Gly Leu Ser Arg Asn Ile Tyr Ser Ala Asp
770                 775                 780

Tyr Tyr Lys Ala Asn Glu Asn Asp Ala Ile Pro Ile Arg Trp Met Pro
785                 790                 795                 800

Pro Glu Ser Ile Phe Tyr Asn Arg Tyr Thr Thr Glu Ser Asp Val Trp
                805                 810                 815

Ala Tyr Gly Val Val Leu Trp Glu Ile Phe Ser Tyr Gly Leu Gln Pro
            820                 825                 830

Tyr Tyr Gly Met Ala His Glu Glu Val Ile Tyr Tyr Val Arg Asp Gly
        835                 840                 845

Asn Ile Leu Ser Cys Pro Glu Asn Cys Pro Val Glu Leu Tyr Asn Leu
850                 855                 860

Met Arg Leu Cys Trp Ser Lys Leu Pro Ala Asp Arg Pro Ser Phe Thr
865                 870                 875                 880

Ser Ile His Arg Ile Leu Glu Arg Met Cys Glu Arg Ala Glu Gly Thr
                885                 890                 895

Val Ser Val

<210> SEQ ID NO 22
<211> LENGTH: 869
<212> TYPE: PRT

<213> ORGANISM: Homo sapiens

<400> SEQUENCE: 22

```
Met Arg Glu Leu Val Asn Ile Pro Leu Val His Ile Leu Thr Leu Val
1               5                   10                  15
Ala Phe Ser Gly Thr Glu Lys Leu Pro Lys Ala Pro Val Ile Thr Thr
            20                  25                  30
Pro Leu Glu Thr Val Asp Ala Leu Val Glu Glu Val Ala Thr Phe Met
        35                  40                  45
Cys Ala Val Glu Ser Tyr Pro Gln Pro Glu Ile Ser Trp Thr Arg Asn
    50                  55                  60
Lys Ile Leu Ile Lys Leu Phe Asp Thr Arg Tyr Ser Ile Arg Glu Asn
65                  70                  75                  80
Gly Gln Leu Leu Thr Ile Leu Ser Val Glu Asp Ser Asp Asp Gly Ile
                85                  90                  95
Tyr Cys Cys Thr Ala Asn Asn Gly Val Gly Gly Ala Val Glu Ser Cys
            100                 105                 110
Gly Ala Leu Gln Val Lys Met Lys Pro Lys Ile Thr Arg Pro Pro Ile
        115                 120                 125
Asn Val Lys Ile Ile Glu Gly Leu Lys Ala Val Leu Pro Cys Thr Thr
130                 135                 140
Met Gly Asn Pro Lys Pro Ser Val Ser Trp Ile Lys Gly Asp Ser Pro
145                 150                 155                 160
Leu Arg Glu Asn Ser Arg Ile Ala Val Leu Glu Ser Gly Ser Leu Arg
                165                 170                 175
Ile His Asn Val Gln Lys Glu Asp Ala Gly Gln Tyr Arg Cys Val Ala
            180                 185                 190
Lys Asn Ser Leu Gly Thr Ala Tyr Ser Lys Val Val Lys Leu Glu Val
        195                 200                 205
Glu Val Phe Ala Arg Ile Leu Arg Ala Pro Glu Ser His Asn Val Thr
210                 215                 220
Phe Gly Ser Phe Val Thr Leu His Cys Thr Ala Thr Gly Ile Pro Val
225                 230                 235                 240
Pro Thr Ile Thr Trp Ile Glu Asn Gly Asn Ala Val Ser Ser Gly Ser
                245                 250                 255
Ile Gln Glu Ser Val Lys Asp Arg Val Ile Asp Ser Arg Leu Gln Leu
            260                 265                 270
Phe Ile Thr Lys Pro Gly Leu Tyr Thr Cys Ile Ala Thr Asn Lys His
        275                 280                 285
Gly Glu Lys Phe Ser Thr Ala Lys Ala Ala Ala Thr Ile Ser Ile Ala
290                 295                 300
Glu Trp Ser Lys Pro Gln Lys Asp Asn Lys Gly Tyr Cys Ala Gln Tyr
305                 310                 315                 320
Arg Gly Glu Val Cys Asn Ala Val Leu Ala Lys Asp Ala Leu Val Phe
                325                 330                 335
Leu Asn Thr Ser Tyr Ala Asp Pro Glu Glu Ala Gln Glu Leu Leu Val
            340                 345                 350
His Thr Ala Trp Asn Glu Leu Lys Val Val Ser Pro Val Cys Arg Pro
        355                 360                 365
Ala Ala Glu Ala Leu Leu Cys Asn His Ile Phe Gln Glu Cys Ser Pro
370                 375                 380
Gly Val Val Pro Thr Pro Ile Pro Ile Cys Arg Glu Tyr Cys Leu Ala
385                 390                 395                 400
```

-continued

```
Val Lys Glu Leu Phe Cys Ala Lys Glu Trp Leu Val Met Glu Glu Lys
                405                 410                 415
Thr His Arg Gly Leu Tyr Arg Ser Glu Met His Leu Leu Ser Val Pro
            420                 425                 430
Glu Cys Ser Lys Leu Pro Ser Met His Trp Asp Pro Thr Ala Cys Ala
        435                 440                 445
Arg Leu Pro His Leu Asp Tyr Asn Lys Glu Asn Leu Lys Thr Phe Pro
    450                 455                 460
Pro Met Thr Ser Ser Lys Pro Ser Val Asp Ile Pro Asn Leu Pro Ser
465                 470                 475                 480
Ser Ser Ser Ser Ser Phe Ser Val Ser Pro Thr Tyr Ser Met Thr Val
                485                 490                 495
Ile Ile Ser Ile Met Ser Ser Phe Ala Ile Phe Val Leu Leu Thr Ile
            500                 505                 510
Thr Thr Leu Tyr Cys Cys Arg Arg Lys Gln Trp Lys Asn Lys Lys
        515                 520                 525
Arg Glu Ser Ala Ala Val Thr Leu Thr Thr Leu Pro Ser Glu Leu Leu
    530                 535                 540
Leu Asp Arg Leu His Pro Asn Pro Met Tyr Gln Arg Met Pro Leu Leu
545                 550                 555                 560
Leu Asn Pro Lys Leu Leu Ser Leu Glu Tyr Pro Arg Asn Asn Ile Glu
                565                 570                 575
Tyr Val Arg Asp Ile Gly Glu Gly Ala Phe Gly Arg Val Phe Gln Ala
            580                 585                 590
Arg Ala Pro Gly Leu Leu Pro Tyr Glu Pro Phe Thr Met Val Ala Val
        595                 600                 605
Lys Met Leu Lys Glu Glu Ala Ser Ala Asp Met Gln Ala Asp Phe Gln
    610                 615                 620
Arg Glu Ala Ala Leu Met Ala Glu Phe Asp Asn Pro Asn Ile Val Lys
625                 630                 635                 640
Leu Leu Gly Val Cys Ala Val Gly Lys Pro Met Cys Leu Leu Phe Glu
                645                 650                 655
Tyr Met Ala Tyr Gly Asp Leu Asn Glu Phe Leu Arg Ser Met Ser Pro
            660                 665                 670
His Thr Val Cys Ser Leu Ser His Ser Asp Leu Ser Met Arg Ala Gln
        675                 680                 685
Val Ser Ser Pro Gly Pro Pro Leu Ser Cys Ala Glu Gln Leu Cys
    690                 695                 700
Ile Ala Arg Gln Val Ala Ala Gly Met Ala Tyr Leu Ser Glu Arg Lys
705                 710                 715                 720
Phe Val His Arg Asp Leu Ala Thr Arg Asn Cys Leu Val Gly Glu Asn
                725                 730                 735
Met Val Val Lys Ile Ala Asp Phe Gly Leu Ser Arg Asn Ile Tyr Ser
            740                 745                 750
Ala Asp Tyr Tyr Lys Ala Asn Glu Asn Asp Ala Ile Pro Ile Arg Trp
        755                 760                 765
Met Pro Pro Glu Ser Ile Phe Tyr Asn Arg Tyr Thr Thr Glu Ser Asp
    770                 775                 780
Val Trp Ala Tyr Gly Val Leu Trp Glu Ile Phe Ser Tyr Gly Leu
785                 790                 795                 800
Gln Pro Tyr Tyr Gly Met Ala His Glu Glu Val Ile Tyr Tyr Val Arg
                805                 810                 815
Asp Gly Asn Ile Leu Ser Cys Pro Glu Asn Cys Pro Val Glu Leu Tyr
```

```
                    820                 825                 830
Asn Leu Met Arg Leu Cys Trp Ser Lys Leu Pro Ala Asp Arg Pro Ser
                835                 840                 845

Phe Thr Ser Ile His Arg Ile Leu Glu Arg Met Cys Glu Arg Ala Glu
            850                 855                 860

Gly Thr Val Ser Val
865

<210> SEQ ID NO 23
<211> LENGTH: 861
<212> TYPE: PRT
<213> ORGANISM: Homo sapiens

<400> SEQUENCE: 23

Met Arg Glu Leu Val Asn Ile Pro Leu Val His Ile Leu Thr Leu Val
  1               5                  10                  15

Ala Phe Ser Gly Thr Glu Lys Leu Pro Lys Ala Pro Val Ile Thr Thr
                 20                  25                  30

Pro Leu Glu Thr Val Asp Ala Leu Val Glu Glu Val Ala Thr Phe Met
             35                  40                  45

Cys Ala Val Glu Ser Tyr Pro Gln Pro Glu Ile Ser Trp Thr Arg Asn
 50                  55                  60

Lys Ile Leu Ile Lys Leu Phe Asp Thr Arg Tyr Ser Ile Arg Glu Asn
 65                  70                  75                  80

Gly Gln Leu Leu Thr Ile Leu Ser Val Glu Asp Ser Asp Asp Gly Ile
                 85                  90                  95

Tyr Cys Cys Thr Ala Asn Asn Gly Val Gly Gly Ala Val Glu Ser Cys
            100                 105                 110

Gly Ala Leu Gln Val Lys Met Lys Pro Lys Ile Thr Arg Pro Pro Ile
        115                 120                 125

Asn Val Lys Ile Ile Glu Gly Leu Lys Ala Val Leu Pro Cys Thr Thr
130                 135                 140

Met Gly Asn Pro Lys Pro Ser Val Ser Trp Ile Lys Gly Asp Ser Pro
145                 150                 155                 160

Leu Arg Glu Asn Ser Arg Ile Ala Val Leu Glu Ser Gly Ser Leu Arg
                165                 170                 175

Ile His Asn Val Gln Lys Glu Asp Ala Gly Gln Tyr Arg Cys Val Ala
            180                 185                 190

Lys Asn Ser Leu Gly Thr Ala Tyr Ser Lys Val Val Lys Leu Glu Val
        195                 200                 205

Glu Val Phe Ala Arg Ile Leu Arg Ala Pro Glu Ser His Asn Val Thr
210                 215                 220

Phe Gly Ser Phe Val Thr Leu His Cys Thr Ala Thr Gly Ile Pro Val
225                 230                 235                 240

Pro Thr Ile Thr Trp Ile Glu Asn Gly Asn Ala Val Ser Ser Gly Ser
                245                 250                 255

Ile Gln Glu Ser Val Lys Asp Arg Val Ile Asp Ser Arg Leu Gln Leu
            260                 265                 270

Phe Ile Thr Lys Pro Gly Leu Tyr Thr Cys Ile Ala Thr Asn Lys His
        275                 280                 285

Gly Glu Lys Phe Ser Thr Ala Lys Ala Ala Ala Thr Ile Ser Ile Ala
    290                 295                 300

Glu Trp Ser Lys Pro Gln Lys Asp Asn Lys Gly Tyr Cys Ala Gln Tyr
305                 310                 315                 320
```

```
Arg Gly Glu Val Cys Asn Ala Val Leu Ala Lys Asp Ala Leu Val Phe
            325                 330                 335
Leu Asn Thr Ser Tyr Ala Asp Pro Glu Ala Gln Glu Leu Leu Val
        340                 345                 350
His Thr Ala Trp Asn Glu Leu Lys Val Val Ser Pro Val Cys Arg Pro
        355                 360                 365
Ala Ala Glu Ala Leu Leu Cys Asn His Ile Phe Gln Glu Cys Ser Pro
370                 375                 380
Gly Val Val Pro Thr Pro Ile Pro Ile Cys Arg Glu Tyr Cys Leu Ala
385                 390                 395                 400
Val Lys Glu Leu Phe Cys Ala Lys Glu Trp Leu Val Met Glu Glu Lys
            405                 410                 415
Thr His Arg Gly Leu Tyr Arg Ser Glu Met His Leu Leu Ser Val Pro
            420                 425                 430
Glu Cys Ser Lys Leu Pro Ser Met His Trp Asp Pro Thr Ala Cys Ala
        435                 440                 445
Arg Leu Pro His Leu Ala Phe Pro Pro Met Thr Ser Ser Lys Pro Ser
        450                 455                 460
Val Asp Ile Pro Asn Leu Pro Ser Ser Ser Ser Ser Phe Ser Val
465                 470                 475                 480
Ser Pro Thr Tyr Ser Met Thr Val Ile Ile Ser Ile Met Ser Ser Phe
            485                 490                 495
Ala Ile Phe Val Leu Leu Thr Ile Thr Thr Leu Tyr Cys Cys Arg Arg
            500                 505                 510
Arg Lys Gln Trp Lys Asn Lys Lys Arg Glu Ser Ala Ala Val Thr Leu
        515                 520                 525
Thr Thr Leu Pro Ser Glu Leu Leu Leu Asp Arg Leu His Pro Asn Pro
        530                 535                 540
Met Tyr Gln Arg Met Pro Leu Leu Leu Asn Pro Lys Leu Leu Ser Leu
545                 550                 555                 560
Glu Tyr Pro Arg Asn Asn Ile Glu Tyr Val Arg Asp Ile Gly Glu Gly
            565                 570                 575
Ala Phe Gly Arg Val Phe Gln Ala Arg Ala Pro Gly Leu Leu Pro Tyr
            580                 585                 590
Glu Pro Phe Thr Met Val Ala Val Lys Met Leu Lys Glu Glu Ala Ser
        595                 600                 605
Ala Asp Met Gln Ala Asp Phe Gln Arg Glu Ala Ala Leu Met Ala Glu
        610                 615                 620
Phe Asp Asn Pro Asn Ile Val Lys Leu Leu Gly Val Cys Ala Val Gly
625                 630                 635                 640
Lys Pro Met Cys Leu Leu Phe Glu Tyr Met Ala Tyr Gly Asp Leu Asn
            645                 650                 655
Glu Phe Leu Arg Ser Met Ser Pro His Thr Val Cys Ser Leu Ser His
            660                 665                 670
Ser Asp Leu Ser Met Arg Ala Gln Val Ser Ser Pro Gly Pro Pro
        675                 680                 685
Leu Ser Cys Ala Glu Gln Leu Cys Ile Ala Arg Gln Val Ala Ala Gly
        690                 695                 700
Met Ala Tyr Leu Ser Glu Arg Lys Phe Val His Arg Asp Leu Ala Thr
705                 710                 715                 720
Arg Asn Cys Leu Val Gly Glu Asn Met Val Val Lys Ile Ala Asp Phe
            725                 730                 735
Gly Leu Ser Arg Asn Ile Tyr Ser Ala Asp Tyr Tyr Lys Ala Asn Glu
```

```
                    740                 745                 750
Asn Asp Ala Ile Pro Ile Arg Trp Met Pro Pro Glu Ser Ile Phe Tyr
            755                 760                 765

Asn Arg Tyr Thr Thr Glu Ser Asp Val Trp Ala Tyr Gly Val Val Leu
        770                 775                 780

Trp Glu Ile Phe Ser Tyr Gly Leu Gln Pro Tyr Tyr Gly Met Ala His
785                 790                 795                 800

Glu Glu Val Ile Tyr Tyr Val Arg Asp Gly Asn Ile Leu Ser Cys Pro
                805                 810                 815

Glu Asn Cys Pro Val Glu Leu Tyr Asn Leu Met Arg Leu Cys Trp Ser
            820                 825                 830

Lys Leu Pro Ala Asp Arg Pro Ser Phe Thr Ser Ile His Arg Ile Leu
        835                 840                 845

Glu Arg Met Cys Glu Arg Ala Glu Gly Thr Val Ser Val
    850                 855                 860

<210> SEQ ID NO 24
<211> LENGTH: 115
<212> TYPE: PRT
<213> ORGANISM: Homo sapiens

<400> SEQUENCE: 24

Lys Pro Lys Ile Thr Arg Pro Pro Ile Asn Val Lys Ile Ile Glu Gly
1               5                   10                  15

Leu Lys Ala Val Leu Pro Cys Thr Thr Met Gly Asn Pro Lys Pro Ser
            20                  25                  30

Val Ser Trp Ile Lys Gly Asp Ser Pro Leu Arg Glu Asn Ser Arg Ile
        35                  40                  45

Ala Val Leu Glu Ser Gly Ser Leu Arg Ile His Asn Val Gln Lys Glu
    50                  55                  60

Asp Ala Gly Gln Tyr Arg Cys Val Ala Lys Asn Ser Leu Gly Thr Ala
65                  70                  75                  80

Tyr Ser Lys Val Val Lys Leu Glu Val Glu Gly Ala Lys Gly Ile His
                85                  90                  95

Thr Gln Phe Val Ala Ser Ala Leu Gln Leu Arg Ser Phe Leu Ser Cys
            100                 105                 110

Pro Gln Ile
        115

<210> SEQ ID NO 25
<211> LENGTH: 189
<212> TYPE: PRT
<213> ORGANISM: Homo sapiens

<400> SEQUENCE: 25

Met Ala Gly Asn Gly Arg Glu Asp Pro Gln Arg Thr Leu Gln Ile Arg
1               5                   10                  15

Asp Ala Phe Ala Val Arg Ala Arg Met Gln Gln Ala Ser Gln His Ala
            20                  25                  30

Leu Gly Pro His Gly Leu Cys Gln Thr Ala Thr Ser Arg Glu Ser Ala
        35                  40                  45

Ala Val Thr Leu Thr Thr Leu Pro Ser Glu Leu Leu Leu Asp Arg Leu
    50                  55                  60

His Pro Asn Pro Met Tyr Gln Arg Met Pro Leu Leu Leu Asn Pro Lys
65                  70                  75                  80

Leu Leu Ser Leu Glu Tyr Pro Arg Asn Asn Ile Glu Tyr Val Arg Asp
```

-continued

```
                85                  90                  95
Ile Gly Glu Gly Ala Phe Gly Arg Val Phe Gln Ala Arg Ala Pro Gly
            100                 105                 110

Leu Leu Pro Tyr Glu Pro Phe Thr Met Val Ala Val Lys Met Leu Lys
            115                 120                 125

Glu Glu Ala Ser Ala Asp Met Gln Ala Asp Phe Gln Arg Glu Ala Ala
            130                 135                 140

Leu Met Ala Glu Phe Asp Asn Pro Asn Ile Val Lys Leu Leu Gly Met
145                 150                 155                 160

Lys Ile Gln Val Arg Ile Cys Ile Ser Ser Glu Asn Arg Gly Phe Pro
                165                 170                 175

Ser Phe Ser Pro Leu Val Arg Ala Phe Ser Phe Ser Pro
                180                 185

<210> SEQ ID NO 26
<211> LENGTH: 783
<212> TYPE: PRT
<213> ORGANISM: Homo sapiens

<400> SEQUENCE: 26

Met Arg Glu Leu Val Asn Ile Pro Leu Val His Ile Leu Thr Leu Val
1               5                   10                  15

Ala Phe Ser Gly Thr Glu Lys Leu Pro Lys Ala Pro Val Ile Thr Thr
            20                  25                  30

Pro Leu Glu Thr Val Asp Ala Leu Val Glu Glu Val Ala Thr Phe Met
            35                  40                  45

Cys Ala Val Glu Ser Tyr Pro Gln Pro Glu Ile Ser Trp Thr Arg Asn
        50                  55                  60

Lys Ile Leu Ile Lys Leu Phe Asp Thr Arg Tyr Ser Ile Arg Glu Asn
65                  70                  75                  80

Gly Gln Leu Leu Thr Ile Leu Ser Val Glu Asp Ser Asp Asp Gly Ile
                85                  90                  95

Tyr Cys Cys Thr Ala Asn Asn Gly Val Gly Gly Ala Val Glu Ser Cys
            100                 105                 110

Gly Ala Leu Gln Val Lys Met Lys Pro Lys Ile Thr Arg Pro Pro Ile
            115                 120                 125

Asn Val Lys Ile Ile Glu Gly Leu Lys Ala Val Leu Pro Cys Thr Thr
130                 135                 140

Met Gly Asn Pro Lys Pro Ser Val Ser Trp Ile Lys Gly Asp Ser Pro
145                 150                 155                 160

Leu Arg Glu Asn Ser Arg Ile Ala Val Leu Glu Ser Gly Ser Leu Arg
                165                 170                 175

Ile His Asn Val Gln Lys Glu Asp Ala Gly Gln Tyr Arg Cys Val Ala
            180                 185                 190

Lys Asn Ser Leu Gly Thr Ala Tyr Ser Lys Val Val Lys Leu Glu Val
            195                 200                 205

Glu Glu Glu Ser Glu Pro Glu Gln Asp Thr Lys Val Phe Ala Arg Ile
            210                 215                 220

Leu Arg Ala Pro Glu Ser His Asn Val Thr Phe Gly Ser Phe Val Thr
225                 230                 235                 240

Leu His Cys Thr Ala Thr Gly Ile Pro Val Pro Thr Ile Thr Trp Ile
                245                 250                 255

Glu Asn Gly Asn Ala Val Ser Ser Gly Ser Ile Gln Glu Ser Val Lys
            260                 265                 270
```

```
Asp Arg Val Ile Asp Ser Arg Leu Gln Leu Phe Ile Thr Lys Pro Gly
            275                 280                 285
Leu Tyr Thr Cys Ile Ala Thr Asn Lys His Gly Glu Lys Phe Ser Thr
        290                 295                 300
Ala Lys Ala Ala Ala Thr Ile Ser Ile Ala Asp Phe Arg Glu Tyr Cys
305                 310                 315                 320
Leu Ala Val Lys Glu Leu Phe Cys Ala Lys Glu Trp Leu Val Met Glu
                325                 330                 335
Glu Lys Thr His Arg Gly Leu Tyr Arg Ser Glu Met His Leu Leu Ser
            340                 345                 350
Val Pro Glu Cys Ser Lys Leu Pro Ser Met His Trp Asp Pro Thr Ala
        355                 360                 365
Cys Ala Arg Leu Pro His Leu Ala Phe Pro Pro Met Thr Ser Ser Lys
370                 375                 380
Pro Ser Val Asp Ile Pro Asn Leu Pro Ser Ser Ser Ser Ser Ser Phe
385                 390                 395                 400
Ser Val Ser Pro Thr Tyr Ser Met Thr Val Ile Ile Ser Ile Met Ser
                405                 410                 415
Ser Phe Ala Ile Phe Val Leu Leu Thr Ile Thr Thr Leu Tyr Cys Cys
            420                 425                 430
Arg Arg Arg Lys Gln Trp Lys Asn Lys Lys Arg Glu Ser Ala Ala Val
        435                 440                 445
Thr Leu Thr Thr Leu Pro Ser Glu Leu Leu Leu Asp Arg Leu His Pro
450                 455                 460
Asn Pro Met Tyr Gln Arg Met Pro Leu Leu Leu Asn Pro Lys Leu Leu
465                 470                 475                 480
Ser Leu Glu Tyr Pro Arg Asn Asn Ile Glu Tyr Val Arg Asp Ile Gly
                485                 490                 495
Glu Gly Ala Phe Gly Arg Val Phe Gln Ala Arg Ala Pro Gly Leu Leu
            500                 505                 510
Pro Tyr Glu Pro Phe Thr Met Val Ala Val Lys Met Leu Lys Glu Glu
        515                 520                 525
Ala Ser Ala Asp Met Gln Ala Asp Phe Gln Arg Glu Ala Ala Leu Met
530                 535                 540
Ala Glu Phe Asp Asn Pro Asn Ile Val Lys Leu Leu Gly Val Cys Ala
545                 550                 555                 560
Val Gly Lys Pro Met Cys Leu Leu Phe Glu Tyr Met Ala Tyr Gly Asp
                565                 570                 575
Leu Asn Glu Phe Leu Arg Ser Met Ser Pro His Thr Val Cys Ser Leu
            580                 585                 590
Ser His Ser Asp Leu Ser Met Arg Ala Gln Val Ser Ser Pro Gly Pro
        595                 600                 605
Pro Pro Leu Ser Cys Ala Glu Gln Leu Cys Ile Ala Arg Gln Val Ala
610                 615                 620
Ala Gly Met Ala Tyr Leu Ser Glu Arg Lys Phe Val His Arg Asp Leu
625                 630                 635                 640
Ala Thr Arg Asn Cys Leu Val Gly Glu Asn Met Val Val Lys Ile Ala
                645                 650                 655
Asp Phe Gly Leu Ser Arg Asn Ile Tyr Ser Ala Asp Tyr Tyr Lys Ala
            660                 665                 670
Asn Glu Asn Asp Ala Ile Pro Ile Arg Trp Met Pro Pro Glu Ser Ile
        675                 680                 685
Phe Tyr Asn Arg Tyr Thr Thr Glu Ser Asp Val Trp Ala Tyr Gly Val
```

```
                690                 695                 700
Val Leu Trp Glu Ile Phe Ser Tyr Gly Leu Gln Pro Tyr Tyr Gly Met
705                 710                 715                 720

Ala His Glu Glu Val Ile Tyr Tyr Val Arg Asp Gly Asn Ile Leu Ser
                725                 730                 735

Cys Pro Glu Asn Cys Pro Val Glu Leu Tyr Asn Leu Met Arg Leu Cys
                740                 745                 750

Trp Ser Lys Leu Pro Ala Asp Arg Pro Ser Phe Thr Ser Ile His Arg
                755                 760                 765

Ile Leu Glu Arg Met Cys Glu Arg Ala Glu Gly Thr Val Ser Val
                770                 775                 780

<210> SEQ ID NO 27
<211> LENGTH: 783
<212> TYPE: PRT
<213> ORGANISM: Homo sapiens

<400> SEQUENCE: 27

Met Arg Glu Leu Val Asn Ile Pro Leu Val His Ile Leu Thr Leu Val
1               5                   10                  15

Ala Phe Ser Gly Thr Glu Lys Leu Pro Lys Ala Pro Val Ile Thr Thr
                20                  25                  30

Pro Leu Glu Thr Val Asp Ala Leu Val Glu Glu Val Ala Thr Phe Met
                35                  40                  45

Cys Ala Val Glu Ser Tyr Pro Gln Pro Glu Ile Ser Trp Thr Arg Asn
                50                  55                  60

Lys Ile Leu Ile Lys Leu Phe Asp Thr Arg Tyr Ser Ile Arg Glu Asn
65                  70                  75                  80

Gly Gln Leu Leu Thr Ile Leu Ser Val Glu Asp Ser Asp Asp Gly Ile
                85                  90                  95

Tyr Cys Cys Thr Ala Asn Asn Gly Val Gly Gly Ala Val Glu Ser Cys
                100                 105                 110

Gly Ala Leu Gln Val Lys Met Lys Pro Lys Ile Thr Arg Pro Pro Ile
                115                 120                 125

Asn Val Lys Ile Ile Glu Gly Leu Lys Ala Val Leu Pro Cys Thr Thr
                130                 135                 140

Met Gly Asn Pro Lys Pro Ser Val Ser Trp Ile Lys Gly Asp Ser Pro
145                 150                 155                 160

Leu Arg Glu Asn Ser Arg Ile Ala Val Leu Glu Ser Gly Ser Leu Arg
                165                 170                 175

Ile His Asn Val Gln Lys Glu Asp Ala Gly Gln Tyr Arg Cys Val Ala
                180                 185                 190

Lys Asn Ser Leu Gly Thr Ala Tyr Ser Lys Val Val Lys Leu Glu Val
                195                 200                 205

Glu Glu Glu Ser Glu Pro Glu Gln Asp Thr Lys Val Phe Ala Arg Ile
                210                 215                 220

Leu Arg Ala Pro Glu Ser His Asn Val Thr Phe Gly Ser Phe Val Thr
225                 230                 235                 240

Leu His Cys Thr Ala Thr Gly Ile Pro Val Pro Thr Ile Thr Trp Ile
                245                 250                 255

Glu Asn Gly Asn Ala Val Ser Ser Gly Ser Ile Gln Glu Ser Val Lys
                260                 265                 270

Asp Arg Val Ile Asp Ser Arg Leu Gln Leu Phe Ile Thr Lys Pro Gly
                275                 280                 285
```

```
Leu Tyr Thr Cys Ile Ala Thr Asn Lys His Gly Glu Lys Phe Ser Thr
    290                 295                 300
Ala Lys Ala Ala Thr Ile Ser Ile Ala Glu Trp Arg Glu Tyr Cys
305                 310                 315                 320
Leu Ala Val Lys Glu Leu Phe Cys Ala Lys Glu Trp Leu Val Met Glu
                325                 330                 335
Glu Lys Thr His Arg Gly Leu Tyr Arg Ser Glu Met His Leu Leu Ser
            340                 345                 350
Val Pro Glu Cys Ser Lys Leu Pro Ser Met His Trp Asp Pro Thr Ala
        355                 360                 365
Cys Ala Arg Leu Pro His Leu Ala Phe Pro Pro Met Thr Ser Ser Lys
370                 375                 380
Pro Ser Val Asp Ile Pro Asn Leu Pro Ser Ser Ser Ser Ser Phe
385                 390                 395                 400
Ser Val Ser Pro Thr Tyr Ser Met Thr Val Ile Ser Ile Met Ser
                405                 410                 415
Ser Phe Ala Ile Phe Val Leu Leu Thr Ile Thr Thr Leu Tyr Cys Cys
            420                 425                 430
Arg Arg Arg Lys Gln Trp Lys Asn Lys Lys Arg Glu Ser Ala Ala Val
        435                 440                 445
Thr Leu Thr Thr Leu Pro Ser Glu Leu Leu Leu Asp Arg Leu His Pro
    450                 455                 460
Asn Pro Met Tyr Gln Arg Met Pro Leu Leu Leu Asn Pro Lys Leu Leu
465                 470                 475                 480
Ser Leu Glu Tyr Pro Arg Asn Asn Ile Glu Tyr Val Arg Asp Ile Gly
                485                 490                 495
Glu Gly Ala Phe Gly Arg Val Phe Gln Ala Arg Ala Pro Gly Leu Leu
            500                 505                 510
Pro Tyr Glu Pro Phe Thr Met Val Ala Val Lys Met Leu Lys Glu Glu
        515                 520                 525
Ala Ser Ala Asp Met Gln Ala Asp Phe Gln Arg Glu Ala Ala Leu Met
530                 535                 540
Ala Glu Phe Asp Asn Pro Asn Ile Val Lys Leu Leu Gly Val Cys Ala
545                 550                 555                 560
Val Gly Lys Pro Met Cys Leu Leu Phe Glu Tyr Met Ala Tyr Gly Asp
                565                 570                 575
Leu Asn Glu Phe Leu Arg Ser Met Ser Pro His Thr Val Cys Ser Leu
            580                 585                 590
Ser His Ser Asp Leu Ser Met Arg Ala Gln Val Ser Ser Pro Gly Pro
        595                 600                 605
Pro Pro Leu Ser Cys Ala Glu Gln Leu Cys Ile Ala Arg Gln Val Ala
610                 615                 620
Ala Gly Met Ala Tyr Leu Ser Glu Arg Lys Phe Val His Arg Asp Leu
625                 630                 635                 640
Ala Thr Arg Asn Cys Leu Val Gly Glu Asn Met Val Val Lys Ile Ala
                645                 650                 655
Asp Phe Gly Leu Ser Arg Asn Ile Tyr Ser Ala Asp Tyr Tyr Lys Ala
            660                 665                 670
Asn Glu Asn Asp Ala Ile Pro Ile Arg Trp Met Pro Pro Glu Ser Ile
        675                 680                 685
Phe Tyr Asn Arg Tyr Thr Thr Glu Ser Asp Val Trp Ala Tyr Gly Val
    690                 695                 700
Val Leu Trp Glu Ile Phe Ser Tyr Gly Leu Gln Pro Tyr Tyr Gly Met
```

-continued

```
            705                 710                 715                 720
Ala His Glu Glu Val Ile Tyr Tyr Val Arg Asp Gly Asn Ile Leu Ser
                    725                 730                 735

Cys Pro Glu Asn Cys Pro Val Glu Leu Tyr Asn Leu Met Arg Leu Cys
                740                 745                 750

Trp Ser Lys Leu Pro Ala Asp Arg Pro Ser Phe Thr Ser Ile His Arg
            755                 760                 765

Ile Leu Glu Arg Met Cys Glu Arg Ala Glu Gly Thr Val Ser Val
    770                 775                 780
```